(12) United States Patent
Rey et al.

(10) Patent No.: US 10,472,639 B2
(45) Date of Patent: *Nov. 12, 2019

(54) NON-REPLICATIVE TRANSDUCTION PARTICLES AND TRANSDUCTION PARTICLE-BASED REPORTER SYSTEMS

(71) Applicant: GeneWeave Biosciences, Inc., Los Gatos, CA (US)

(72) Inventors: Diego Ariel Rey, San Francisco, CA (US); Marc Rehfuss, Alameda, CA (US); Xiaowen Liu, Cupertino, CA (US)

(73) Assignee: Geneweave Biosciences, Inc., Los Gatos, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 15/434,937

(22) Filed: Feb. 16, 2017

(65) Prior Publication Data
US 2017/0166907 A1    Jun. 15, 2017

Related U.S. Application Data

(63) Continuation of application No. PCT/US2015/046758, filed on Aug. 25, 2015.

(60) Provisional application No. 62/202,653, filed on Aug. 7, 2015, provisional application No. 62/041,539, filed on Aug. 25, 2014.

(51) Int. Cl.
| C12N 15/70 | (2006.01) |
| C12N 7/00 | (2006.01) |
| C12N 15/74 | (2006.01) |
| C12Q 1/6897 | (2018.01) |
| C07K 14/005 | (2006.01) |
| C12N 9/02 | (2006.01) |
| C12N 9/16 | (2006.01) |

(52) U.S. Cl.
CPC ............ *C12N 15/70* (2013.01); *C07K 14/005* (2013.01); *C12N 7/00* (2013.01); *C12N 9/0069* (2013.01); *C12N 9/16* (2013.01); *C12N 15/74* (2013.01); *C12Q 1/6897* (2013.01); *C12Y 113/12007* (2013.01); *C12N 2795/10122* (2013.01); *C12N 2795/10143* (2013.01); *C12N 2795/10152* (2013.01)

(58) Field of Classification Search
None
See application file for complete search history.

(56) References Cited

U.S. PATENT DOCUMENTS

| 5,508,187 A | 4/1996 | Frackman et al. |
| 5,691,185 A | 11/1997 | Dickely et al. |
| 5,888,721 A | 3/1999 | Rothstein et al. |
| 6,248,569 B1 | 6/2001 | Dunn et al. |
| 7,045,338 B2 | 5/2006 | Bramucci |
| 8,192,959 B2 | 6/2012 | Payne et al. |
| 8,619,257 B2 | 12/2013 | Plowman et al. |
| 8,829,473 B1 | 9/2014 | Griswold et al. |
| 9,388,453 B2 | 7/2016 | Rey |
| 2004/0018514 A1 | 1/2004 | Kunst et al. |
| 2005/0118719 A1 | 6/2005 | Schmidt et al. |
| 2011/0300125 A1 | 12/2011 | Reich et al. |
| 2014/0206577 A1 | 7/2014 | Young et al. |
| 2014/0272928 A1 | 9/2014 | Rey et al. |
| 2014/0278136 A1 | 9/2014 | Shamsheyeva et al. |

FOREIGN PATENT DOCUMENTS

| EP | 0712935 A2 | 5/1996 |
| WO | 198909826 A1 | 10/1989 |
| WO | 1996021007 A2 | 7/1996 |
| WO | 199914318 A1 | 3/1999 |
| WO | 200175067 A1 | 10/2001 |
| WO | 2002055732 A1 | 7/2002 |
| WO | 2002081679 A2 | 10/2002 |
| WO | 2003060066 A2 | 7/2003 |
| WO | 2004111251 A2 | 12/2004 |
| WO | 2006075996 A2 | 7/2006 |
| WO | 2008131230 A1 | 10/2008 |
| WO | 2009017821 A1 | 2/2009 |
| WO | 2009045550 | 4/2009 |
| WO | 2014124226 A1 | 8/2014 |
| WO | 2014160418 A2 | 10/2014 |

OTHER PUBLICATIONS

Feiss, M. et al., "Bacteriophage Lambda DNA packaging: Scanning for the terminal cohesive end site during packaging", 1982, Proc. Natl. Acad. Sci. U.S.A., 79, pp. 3498-3502.
Chung, J. et al., "Bacteriophage T7 DNA Packaging", 1990, J. Mol. Bio., 216, pp. 911-926.
Charpentier E et al, Shuttle Vector pNR46124 complete sequence, GenBank Accession No. KM015350.1, 2004, p. 1-4, NCBI.
Chen FJ et al, Complete Genome Sequence of *Staphylococcus aureus* Z172, a Vancomycin-Intermediate and Daptomycin-Nonsusceptible Methicillin-Resistant Strain Isolated in Taiwan, Genome Announcements, Dec. 5, 2013, pp. e01011-13 (1-2), vol. 1, No. 6, American Society for Microbiology.
Christie GE et al, The complete genomes of *Staphylococcus aureus* bacteriophages 80 and 80alpha-Implications for the specificity of SaPI mobilization, Virology, Nov. 25, 2010, pp. 381-390, vol. 407, No. 2, Elsevier Inc.
Holden MTG et al, Genome Sequence of a Recently Emerged, Highly Transmissible, Multi-Antibiotic- and Antiseptic-Resistant Variant of Methicillin-Resistant *Staphylococcus aureus*, Sequence Type 239 (TW), Journal of Bacteriology, Feb. 2010, pp. 888-892, vol. 192, No. 3, American Society for Microbiology.

(Continued)

*Primary Examiner* — Mindy G Brown
(74) *Attorney, Agent, or Firm* — David J. Chang

(57) ABSTRACT

Methods and systems are provided for packaging reporter nucleic acid molecules into non-replicative transduction particles for use as reporter molecules. The non-replicative transduction particles can be constructed from viruses and use viral transduction and replication systems. The reporter nucleic acid molecules include a reporter gene, such as a reporter molecule or selectable marker, for detecting target genes or cells. Methods and systems are provided for detection of cells and target nucleic acid molecules using the non-replicative transduction particles as reporter molecules.

21 Claims, 10 Drawing Sheets

Specification includes a Sequence Listing.

(56) References Cited

OTHER PUBLICATIONS

Kim SW et al, Role of RepB in the replication of plasmid pJB01 isolated from Enterococcus faecium JC1, Plasmid, Mar. 2006, pp. 99-113, vol. 55, Issue 2, Elsevier Inc.

Kyle JL et al, *Escherichia coli* Serotype O55:H7 Diversity Supports Parallel Acquisition of Bacteriophage at Shiga Toxin Phage Insertion Sites during Evolution of the O157:H7 Lineage, Journal of Bacteriology, Feb. 10, 2012, pp. 1885-1896, vol. 194, No. 8, American Society for Microbiology.

Lobocka M B et al, Genome of Bacteriophage P1, Journal of Bacteriology, Nov. 2004, pp. 7032-7068, vol. 186, No. 21, American Society for Microbiology.

Skorupski K et al, Bacteriophage P1 genes involved in the recognition and cleavage of the phage packaging site (pac), Journal of Molecular Biology, Feb. 20, 1992, pp. 977-989, vol. 223, Issue 4, Elsevier.

Stevens RH et al, The annotated complete DNA sequence of Enterococcus faecalis bacteriophage PhiEF11 and its comparison with all available phage and predicted prophage genomes, FEMS Microbiology Letters, Jan. 24, 2011, pp. 9-26, vol. 317, Blackwell Publishing Ltd.

International Search Report, PCT/US15/46758, dated Jan. 13, 2016.

| | 1505 | 1525 |
|---|---|---|
| KanR | 3/12 | 12/12 |
| SpecR | 12/12 | 12/12 |

FIGURE 10

NON-REPLICATIVE TRANSDUCTION PARTICLES AND TRANSDUCTION PARTICLE-BASED REPORTER SYSTEMS

CROSS-REFERENCE TO RELATED APPLICATION

This application is a continuation of International Application No. PCT/US2015/046758 filed Aug. 25, 2015, which claims the benefit of U.S. Provisional Patent Application No. 62/041,539, filed Aug. 25, 2014, and U.S. Provisional Patent Application No. 62/202,653, filed Aug. 7, 2015, the disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jul. 5, 2019, is named 33168_US2_New_SequenceListing.txt and is 37, 930 bytes in size.

BACKGROUND OF THE INVENTION

Field of the Invention

The invention relates to methods and compositions for packaging and delivery of non-replicative transduction reporter molecules into cells for detecting target genes in cells.

Description of the Related Art

A transduction particle refers to a virus capable of delivering a non-viral nucleic acid into a cell. Viral-based reporter systems have been used to detect the presence of cells and rely on the lysogenic phase of the virus to allow expression of a reporter molecule from the cell. These viral-based reporter systems use replication-competent transduction particles that express reporter molecules and cause a target cell to emit a detectable signal.

However, the lytic cycle of the virus has been shown to be deleterious to viral-based reporter assays. Carrière, C. et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239. Carrière et al. developed *M. tuberculosis/bacillus* Calmette-Guérin (BCG) luciferase reporter phages that have their lytic cycles suppressed at 30° C., but active at 37° C. Using this system, Carrière et al. have demonstrated the detection of BCG using phage reporters with a suppressed lytic cycle.

There are disadvantages, however, associated with suppressing but not eliminating the replication functions of the bacteriophage in bacteriophage-based reporter assays. First, controlling replication functions of the bacteriophage imposes limiting assay conditions. For example, the lytic cycle of the reporter phage phAE40 used by Carrière et al. was repressed when the phage was used to infect cells at the non-permissive temperature of 30° C. This temperature requirement imposed limiting conditions on the reporter assay in that the optimum temperature for the target bacteria was 37° C. These limiting conditions hinder optimum assay performance.

Moreover, the replication functions of the virus are difficult to control. The replication of the virus should be suppressed during the use of the transduction particles as a reporter system. For example, the lytic activity of the reporter phage phAE40 reported by Carrière et al. was reduced but was not eliminated, resulting in a drop in luciferase signal in the assay. Carrière et al. highlighted possible causes for the resulting drop in reporter signal, such as intact phage-expressed genes and temperature limitations of the assay, all stemming from the fact that the lytic cycle of the phage reporter was not eliminated.

Reporter assays relying on the natural lysogenic cycle of phages can be expected to exhibit lytic activity sporadically. In addition, assays that rely on the lysogenic cycle of the phage can be prone to superinfection immunity from target cells already lysogenized with a similar phage, as well as naturally occurring host restriction systems that target incoming virus nucleic acid, thus limiting the host range of these reporter phages.

In other examples, transduction particle production systems are designed to package exogenous nucleic acid molecules, but the transduction particle often contains a combination of exogenous nucleic acid molecules and native progeny virus nucleic acid molecules. The native virus can exhibit lytic activity that is a hindrance to assay performance, and the lytic activity of the virus must be eliminated to purify transduction particles. However, this purification is generally not possible. In U.S. 2009/0155768 A, entitled *Reporter Plasmid Packaging System for Detection of Bacteria*, Scholl et al. describes the development of such a transduction particle system. The product of the system is a combination of reporter transduction particles and native bacteriophage (FIG. 8 in the reference). Although the authors indicate that the transduction particle and native bacteriophage can be separated by ultracentrifugation, this separation is only possible in a system where the transduction particle and the native virus exhibit different densities that would allow separation by ultracentrifugation. While this characteristic is exhibited by the bacteriophage T7-based packaging system described in the reference, this is not a characteristic that is generally applicable for other virus systems. It is common for viral packaging machinery to exhibit headful packaging that would result in native virus and transduction particles to exhibit indistinguishable densities that cannot be separated by ultracentrifugation. Virus packaging systems also rely on a minimum amount of packaging as a requirement for proper virus structural assembly that results in native virus and transduction particles with indistinguishable densities.

Thus, there is a need for non-replicative transduction particles that do not suffer from the deleterious effects from lytic functions of the virus and the possibility of being limited by superinfection immunity and host restriction mechanisms that target virus nucleic acid molecules and viral functions, all of which can limit the performance of the reporter assay by increasing limits of detection and resulting in false negative results.

Even where transduction particles have been engineered, methods for using the transduction particles to detect and report the presence of target nucleic acid molecules in cells have limitations. Some methods require disruption of the cell and cumbersome techniques to isolate and detect transcripts in the lysate. Detection methods include using labeled probes such as antibodies, aptamers, or nucleic acid probes. Labeled probes directed to a target gene can result in non-specific binding to unintended targets or generate signals that have a high signal-to-noise ratio. Therefore, there is a need for specific, effective and accurate methods for detection and reporting of endogenous nucleic acid molecules in cells.

Accordingly, methods and systems are needed for generating non-replicative transduction particles that allow packaging and expression of reporter molecules in cells, while eliminating replication-competent progeny virus. Effective and accurate methods for detecting molecules in cells using the expressed reporter molecules are also needed.

SUMMARY OF THE INVENTION

Disclosed herein is a bacterial cell packaging system for packaging a reporter nucleic acid molecule into a non-replicative transduction particle (NRTP) for introduction into a bacterial cell, the packaging system comprising a host cell, comprising (1) a bacteriophage genome comprising a first gene comprising a disruption, wherein in the absence of the disruption the first gene encodes a first essential component of a packaging-related enzymatic activity and comprises a first packaging initiation site sequence, wherein the packaging-related enzymatic activity recognizes the first packaging initiation site, wherein the disruption prevents recognition of the first packaging initiation site sequence by the first essential component of the packaging-related enzymatic activity, and wherein the disruption further reduces the level of the first essential component of the packaging-related enzymatic activity, and (2) a reporter nucleic acid molecule comprising a reporter gene, a second gene encoding the first essential component of the packaging-related enzymatic activity, and a third gene encoding a second essential component of the packaging-related enzymatic activity, wherein the second gene comprises the non-disrupted first packaging initiation site sequence, wherein the first packaging initiation site sequence is configured to facilitate packaging of a replicon of the reporter nucleic acid molecule into the NRTP.

In an embodiment, the bacteriophage genome comprises a plurality of disrupted genes, wherein in the absence of the disruptions, each of the plurality of disrupted genes encodes an essential component of the packaging-related enzymatic activity. In an embodiment, each of the plurality of disrupted genes on the bacteriophage genome is complemented by a functional, non-disrupted gene encoded by the reporter nucleic acid molecule. In another embodiment, the disruption is via deletion, insertion, mutation, or replacement.

In another embodiment, the reporter nucleic acid molecule comprises a small terminase gene and a large terminase gene. In a further embodiment, the terminase genes comprise a pacA gene and a pacB gene of Enterobacteriaceae bacteriophage P1. In some embodiments, at least one of said terminase genes comprises the sequence of SEQ ID NO:1, SEQ ID NO:4, or SEQ ID NO:6. In an embodiment, the terminase genes comprise a terS gene and a terL gene from a S. aureus bacteriophage φ11 or φ80α. In another embodiment, the terminase genes comprise a terA gene and a terB gene from an E. faecalis bacteriophage φEf11.

In some embodiments, the packaging-related enzymatic activity is a terminase activity. In an embodiment, the second gene and the third gene are each terminase genes. In an embodiment, the second gene is a pacA gene and wherein the third gene is a pacB gene. In an embodiment, the reporter nucleic acid molecule comprises the sequence of SEQ ID NO:1. In an embodiment, the second gene is a terA gene and the third gene is a terB gene. In an embodiment, the reporter nucleic acid molecule comprises the sequence of SEQ ID NO:6. In an embodiment, the second gene is a terS gene and wherein the third gene is a terL gene. In an embodiment, the reporter nucleic acid molecule comprises the sequence of SEQ ID NO:4.

In some embodiments, the second gene and the third gene are operably linked to a conditional promoter. In an embodiment, the conditional promoter comprises the sequence of SEQ ID NO: 9. In an embodiment, the conditional promoter is a native promoter of a terminase gene of the bacteriophage genome. In some embodiments, expression of the second gene or the third gene is inhibited in the absence of activation of the lytic cycle of the bacteriophage, and wherein expression of the second gene or the third gene is activated upon activation of the lytic cycle of the bacteriophage. In certain embodiments, the second gene and the third gene are terminase genes native to the bacteriophage genome, and wherein the conditional promoter is a native promoter of the terminase genes.

In some embodiments, the bacteriophage genome comprises a reporter gene. In some embodiments, the bacteriophage genome further comprises an antibiotic resistance gene. In an embodiment, the reporter gene encodes a detectable marker or a selectable marker. In an embodiment, the reporter gene is selected from the group consisting of: enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3×-FLAG), and selectable markers (ampC, tet(M), CAT, erm). In an embodiment, the reporter gene disrupts a terminase gene. In certain embodiments, the antibiotic resistance gene is a kanamycin resistance gene. In some embodiments, the reporter gene is operatively linked to a constitutive promoter. In a further embodiment, the constitutive promoter is Pblast.

In an embodiment, the disruption comprises an insertion into or replacement of the first packaging initiation site sequence with a gene encoding a selectable marker. In certain embodiments, the gene encoding the selectable marker is operatively linked to a constitutive promoter. In an embodiment, the disruption comprises an insertion into or replacement of the first packaging initiation site sequence with a gene encoding a detectable marker. In an embodiment, the gene encoding the detectable marker is selected from the group consisting of: luxA, luxB, and luxAB. In some embodiments, the gene encoding the detectable marker is operatively linked to a constitutive promoter, e.g., Pblast. In certain embodiments, the first gene comprises a pacA gene locus, and wherein the disruption comprises a luxAB gene and a kan gene inserted into the pacA gene locus. In some embodiments, the bacteriophage genome comprises SEQ ID NO: 12.

In some embodiments, the reporter nucleic acid molecule comprises an origin of replication. In an embodiment, the replicon of the reporter nucleic acid molecule comprises a concatamer amenable to packaging into the non-replicative transduction particle. In certain embodiments, the non-disrupted first packaging initiation site sequence comprises a concatamer junction. In some embodiments, the replicon is an Enterobacteriaceae bacteriophage P1 lytic replicon.

In an embodiment, the replicon comprises a C1 repressor-controlled P53 promoter, a promoter P53 antisense, a repL gene, and an in-frame deletion of a kilA gene. In an embodiment, the replicon comprises the sequence of SEQ ID NO:2. In an embodiment, the replicon is a pBHR1 replicon or a derivative of the pBHR1 replicon. In an embodiment, the replicon comprises the sequence of SEQ ID NO:3. In an embodiment, the reporter nucleic acid molecule comprises the sequence of SEQ ID NO:4. In an embodiment, the replicon of the reporter nucleic acid molecule is derived from a S. aureus pT181 plasmid origin of replication. In an embodiment, the replicon of the reporter nucleic acid molecule comprises the sequence of SEQ ID NO:5. In an embodiment, the reporter nucleic acid molecule comprises the sequence comprises the sequence of SEQ ID NO:6. In an embodiment, the replicon of the reporter nucleic acid molecule is derived from an *Enterococcus* repB plasmid origin of replication. In an embodiment, the replicon of the reporter nucleic acid molecule comprises the sequence of SEQ ID NO:7. In an embodiment, the replicon of the reporter nucleic acid molecule is derived from an *Enterococcus* pDL278 plasmid origin of replication. In an embodiment, the replicon of the nucleic acid molecule comprises the sequence of SEQ ID NO:8. In an embodiment, the non-disrupted first packaging initiation site sequence comprises a pac-site. In an embodiment, the non-disrupted first packaging initiation site sequence comprises a cos-site.

In an embodiment, the bacteriophage genome comprises an Enterobacteriaceae bacteriophage P1. In an embodiment, the bacteriophage genome comprises an *S. aureus* bacteriophage φ80α or a bacteriophage φ11. In an embodiment, the bacteriophage genome comprises an *E. faecalis* bacteriophage φEF11.

In an embodiment, the bacterial cell comprises an *E. coli* cell. In an embodiment, the bacterial cell comprises an *S. aureus* cell. In an embodiment, the bacterial cell comprises an *E. faecalis* cell. In an embodiment, the bacterial cell comprises a Gram-negative cell. In an embodiment, the bacterial cell comprises a Gram-positive cell.

In an embodiment, the reporter gene encodes a detectable marker or a selectable marker. In some embodiments, the reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3x-FLAG), and selectable markers (ampC, tet(M), CAT, erm).

In an embodiment, the reporter nucleic acid molecule comprises an aptamer. In an embodiment, the reporter nucleic acid molecule comprises a nucleic acid transcript sequence that is complementary to a second sequence in the reporter nucleic acid molecule.

In an embodiment, the nucleic acid transcript sequence is complementary to a cellular transcript. In a further embodiment, the nucleic acid transcript sequence comprises a cis-repressing sequence. In an embodiment, the reporter nucleic acid molecule is operatively linked to a promoter. In a further embodiment, the promoter is selected for contributing to reactivity of a reporter molecule expressed from the reporter nucleic acid molecule in the bacterial cell. In some embodiments, the replicon of the reporter nucleic acid molecule comprises a nucleic acid transcript sequence that is complementary to a second sequence in the replica of the reporter nucleic acid molecule.

Also provided herein is a method for packaging a reporter nucleic acid molecule into a non-replicative transduction particle, comprising (1) providing conditions to the bacterial cell packaging system as disclosed herein that induce a lytic phase of the bacteriophage genome to produce non-replicative transduction particles packaged with the reporter nucleic acid molecule; and (2) collecting the non-replicative transduction particle comprising the reporter nucleic acid molecule. In some embodiments, the non-replicative transduction particle does not contain a replicated bacteriophage genome. In some embodiments, the non-replicative transduction particle comprises a portion of the bacteriophage genome due to recombination with the reporter nucleic acid molecule, and wherein the portion of the bacteriophage genome comprises the reporter gene.

Also provided herein is a composition comprising the non-replicative transduction particle comprising a replicon of the reporter nucleic acid molecule produced by the method disclosed herein.

Also provided herein is a bacterial cell packaging system for packaging a nucleic acid molecule into a non-replicative transduction particle, the bacterial cell, comprising (1) a bacteriophage genome comprising a first packaging initiation site sequence, wherein the first packaging initiation site sequence is disrupted by a gene encoding a reporter, and (2) a reporter nucleic acid molecule comprising a second packaging initiation site sequence facilitating packaging of a replicon of the reporter nucleic acid molecule into the non-replicative transduction particle, wherein the reporter nucleic acid molecule forms a replicon configured to be packaged into the non-replicative transduction particle.

Also provided herein is a bacterial cell packaging system for packaging a reporter nucleic acid molecule into a non-replicative transduction particle (NRTP) for introduction into a cell, the packaging system comprising a host cell, comprising (1) a bacteriophage genome comprising a first pair of terminase genes, wherein at least one of the first pair of terminase genes is disrupted, rendering the disrupted terminase gene non-functional, and (2) a reporter nucleic acid molecule comprising a reporter gene and a second pair of terminase genes that complement the first pair of terminase genes, wherein each of the second pair of terminase genes are functional, and wherein the second pair of terminase genes facilitate packaging of a replicon of the reporter nucleic acid molecule into the NRTP.

Also provided herein is a bacterial cell packaging system for packaging a reporter nucleic acid molecule into a non-replicative transduction particle (NRTP) for introduction into a cell, the packaging system comprising a host cell, comprising (1) a bacteriophage genome comprising a first pair of terminase genes, wherein at only one of the first pair of terminase genes is disrupted, rendering the disrupted terminase gene non-functional, and (2) a reporter nucleic acid molecule comprising a reporter gene and a second terminase gene that complements the first terminase gene, wherein the second terminase gene is functional, and wherein the second terminase gene facilitates packaging of a replicon of the reporter nucleic acid molecule into the NRTP.

In some non-replicative transduction particle packaging systems, viral DNA recombined with plasmid DNA can be packaged. In such systems, a lysate produced by the packaging system can contain two species of transduction particles, (1) transduction particles carrying plasmid DNA and (2) transduction particles carrying viral DNA. In such systems, the latter species of transduction particles do not contribute to signal production when using the lysate as a reporter system for the detection of target cells. As such, an improved non-replicative transduction particle-based reporter system is disclosed herein where a reporter gene has been incorporated into the viral genome such that both species of transduction particles are capable of producing signal.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 10 shows a table of data obtained from measuring the light production (RLU) from colonies of transduced cells. Cells that were resistant to spectinomycin (SpecR) were transduced with plasmid DNA while cells that were resistant to kanamycin (KanR) were transduced by P1 DNA. Data obtained from employing a lysate produced from a cell containing P1 without luxAB integrated into its genome (1505) resulted in KanR transductants that generally did not produce light while data obtained from employing a lysate produced from a cell containing P1 with luxAB integrated into its genome (1525) resulted in KanR transductants that did produce light.

DETAILED DESCRIPTION OF THE INVENTION

I. Definitions

Figure 1:
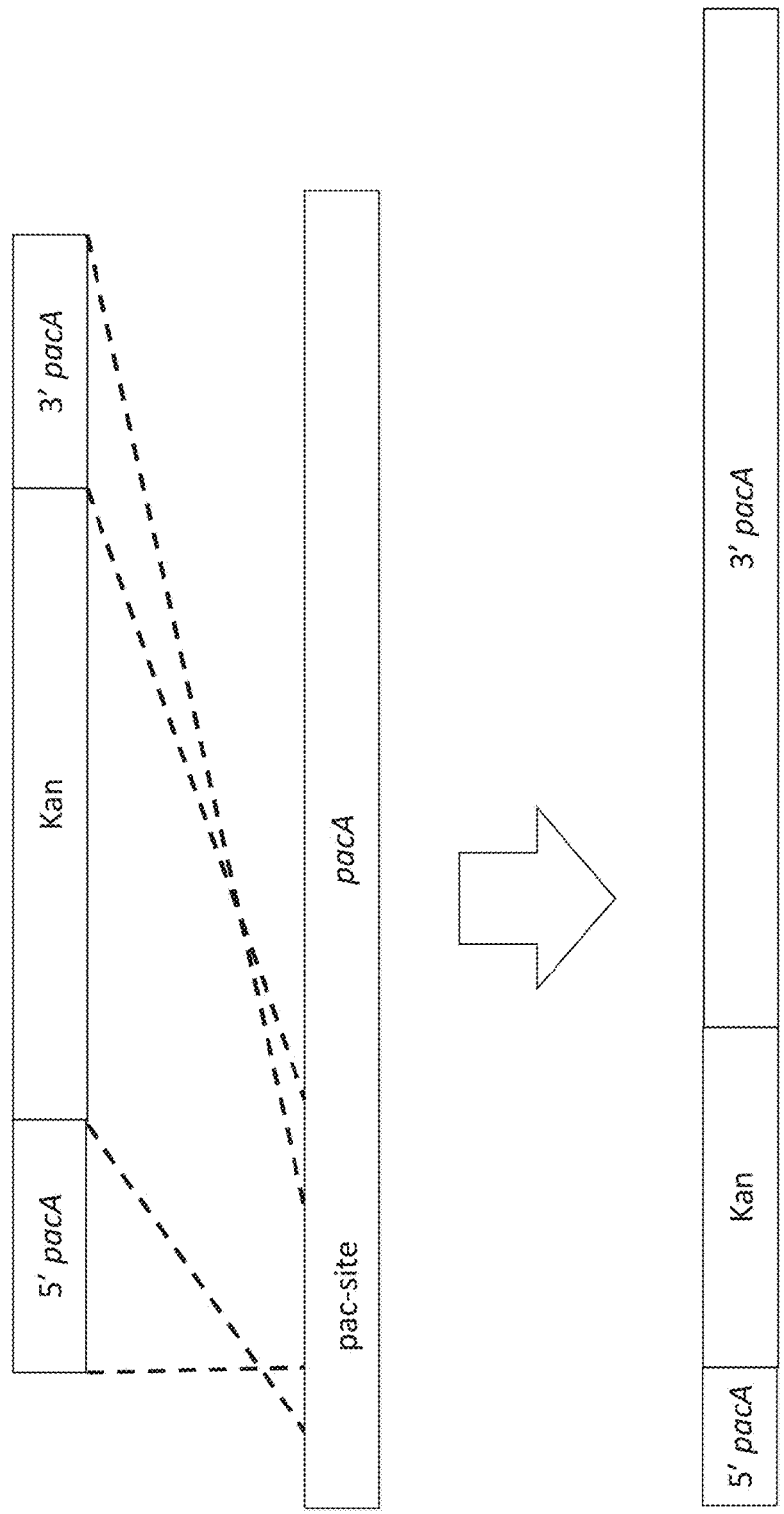
FIG. 1 illustrates an example of pacA gene disruption in the bacteriophage P1 by insertion of a kanamycin resistance gene within the pacA gene via allelic exchange, according to an embodiment.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3×-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "transduction particle" refers to a virus capable of delivering a non-viral nucleic acid molecule into a cell. The virus can be a bacteriophage, adenovirus, etc.

A "non-replicative transduction particle" refers to a virus capable of delivering a non-viral nucleic acid molecule into a cell, but is incapable of packaging its own replicated viral genome into the transduction particle. The virus can be a bacteriophage, adenovirus, etc.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that surrounds the protein coat.

As used herein, the term "complement" refers to a non-disrupted sequence that is in the presence of an identical sequence that has been disrupted, or to the relationship of the non-disrupted sequence to the disrupted sequence. In one embodiment, the complement comprises a gene encoded on a polynucleotide in a cell that is functional and capable of expression, and expresses a protein with the same function as a disrupted gene on a bacteriophage prior to disruption. In some embodiments, the complement gene has greater than 80%, 85%, 90%, 91%, 92%, 93%, 94%, 95%, 96%, 97%, 98%, or 99% sequence identity to the disrupted bacteriophage gene prior to disruption, i.e., the native bacteriophage gene. In some embodiments, the complement gene is identical to the disrupted bacteriophage gene prior to disruption, i.e., the native bacteriophage gene. In some embodiments, the complement gene comprises a polynucleotide sequence that has been deleted from the bacteriophage. In some embodiments, the complement gene refers to a gene encoding packaging machinery of a bacteriophage on a plasmid, where the same gene has been disrupted in a bacteriophage. Thus, the plasmid is required to be in the presence of a bacteriophage with a mutated packaging machinery gene to provide the necessary packaging machinery necessary for packaging a polynucleotide into a transduction particle.

As used herein, the term "packaging-related enzymatic activity" refers to one or more polypeptides crucial for the interaction with a packaging initiation site sequence to package a polynucleotide into a transduction particle. In some embodiments, a pair of terminase genes is required for such an interaction, wherein each terminase encodes a packaging-related enzymatic activity. In some embodiments, the enzymatic activity is encoded by a terS and/or terL gene from a *S. aureus* bacteriophage φ11 or φ80α, a terA and terB gene from an *E. faecalis* bacteriophage φEf11, or a pacA and pacB gene of Enterobacteriaceae bacteriophage P1. In these embodiments, each of the pair of terminase genes express a packaging-related enzymatic activity, and a functional version of both are required for packaging of a polynucleotide with the packaging initiation site. In some embodiments, disruption of one of the genes of a plurality of genes associated with a packaging-related enzymatic activity eliminates the packaging-related enzymatic activity. In some embodiments, both of a pair of terminase genes are disrupted on the bacteriophage, thus disrupting the entire set of packaging-related enzymatic activity encoding genes on the bacteriophage.

"MRSA" refers to Methicillin-resistant *Staphylococcus aureus*.

"MSSA" refers to Methicillin-sensitive *Staphylococcus aureus*.

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, provided the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

II. Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain dormant for long periods of time. If the lysogen is induced, the phage genome is excised from the bacterial chromosome and initiates the lytic cycle, which culminates in lysis of the cell and the release of phage particles. The lytic cycle leads to the production of new phage particles which are released by lysis of the host.

Certain temperate phage can exhibit lytic activity, and the propensity for this may vary with varying host bacteria. To illustrate this phenomenon, the lytic activity of two temperate S. aureus phages on ten MRSA clinical isolates was examined via plaque assay (Table 1). The phage φ11 exhibited lytic activity on 10 out of 10 clinical MRSA isolates and φ80α exhibited lytic activity on six of the 10 clinical MRSA isolates. Thus, reporter assays relying on the natural lysogenic cycle of phages can be expected to exhibit lytic activity sporadically.

TABLE 1

Lytic activity (denoted by the letter "x") of the S. aureus temperate phages φ11 and φ80α on ten clinical MRSA isolates

| MRSA isolate | φ11 | φ80α |
| --- | --- | --- |
| 1 | x | |
| 2 | x | |
| 3 | x | x |
| 4 | x | x |
| 5 | x | x |
| 6 | x | |
| 7 | x | x |
| 8 | x | |
| 9 | x | x |
| 10 | x | x |

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that inhibit phage-derived transcripts.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

III. Methods for Producing Non-Replicative Transduction Particles (NRTP)

Disruption/Complementation-Based Methods for Producing Non-Replicative Transduction Particles.

Disclosed herein are non-replicative transduction particle packaging systems based on disruption of a component of the genome of a virus that is recognized by the viral packaging machinery as the element from which genomic packaging is initiated during viral production. In an embodiment, this disruption disrupts a packaging initiation site from a bacteriophage, and also disrupts a terminase function. Examples of the disrupted elements include the pac-site sequence of pac-type bacteriophages and the cos-site sequence of cos-type bacteriophages. In one embodiment, when the packaging initiation site sequence within the phage is disrupted, the phage cannot produce functional terminases. In an example, the pac-site is encoded within a pacA gene sequence, and terminase functions require both a functional PacA and PacB. In the embodiment, plasmid DNA is packaged into a phage capsid by complementing said disrupted terminases and including a recognizable packaging initiation site on the plasmid DNA. The bacteriophage can be any bacteriophage, such as an Enterobacteriaceae bacteriophage P1 or φEF11, or an *S. aureus* bacteriophage φ80α or a bacteriophage φ11.

Packaging initiation sites are often found within coding regions of genes that are essential to virus production. In some embodiments, a region of the bacteriophage genome is disrupted by an insertion, replacement, deletion, or mutation that disrupts the packaging initiation site. Examples of disruptions that accomplish this include, but are not limited to, an allelic exchange event that replaces a sequence on the bacteriophage genome that contains the packaging initiation site sequence with another sequence such as that of the an antibiotic resistance gene, or the complete deletion of the small and large terminase genes. In an example employing the terminase genes pacA and pacB, pacA can be disrupted in a manner that causes polar effects that also disrupt pacB expression and/or overall terminase function mediated by PacA and PacB. Other examples can include terminase genes can also include terS and terL genes from *S. aureus* bacteriophage φ11 or φ80α, or the terS and terL genes from *E. faecalis* bacteriophage φEf11. In an embodiment, a terminase gene includes SEQ ID NO:10, a P1 pacA gene in which a portion of the gene sequence that contains the pac-site has been replaced by a kanamycin resistance gene. FIG. 1 illustrates an example of the disruption of the pacA gene in the bacteriophage P1 by the insertion of a kanamycin resistance gene within the pacA gene via allelic exchange.

In one example, a cell's genome is lysogenized with a viral genome where the packaging initiation site has been disrupted. In some embodiments, the cell can be an *E. coli* cell, an *S. aureus* cell, or an *E. faecalis* cell. The cell can be Gram-negative or Gram-positive. A complementing plasmid (or reporter nucleic acid molecule) is introduced into the cell, and the plasmid DNA includes at least the gene that has been disrupted in the bacteriophage, as well as the packaging initiation site sequence, and optionally additional bacteriophage genes and a reporter gene, which can encode a detectable and/or a selectable marker. The plasmid can be constructed using methods found in International App. No. PCT US 2014/026536, hereby incorporated by reference in its entirety. In some embodiments, the packaging initiation site sequence includes a pac-site or a cos-site. In an embodiment, the packaging initiation site sequence includes the sequence of SEQ ID NO: 1, SEQ ID NO: 4, or SEQ ID NO: 6. One or more genes of the plasmid can be operatively linked to a promoter, such as an inducible promoter (which can be induced when packaging is initiated by inducing the bacteriophage). In some embodiments, the promoter can be a native promoter of a small terminase gene or a large terminase gene. In an embodiment, the native promoter can be controlled by the bacteriophage, and thus effectively acts as a conditional promoter induced during packaging. In an embodiment, the promoter includes the sequence of SEQ ID NO: 9.

Figure 2:
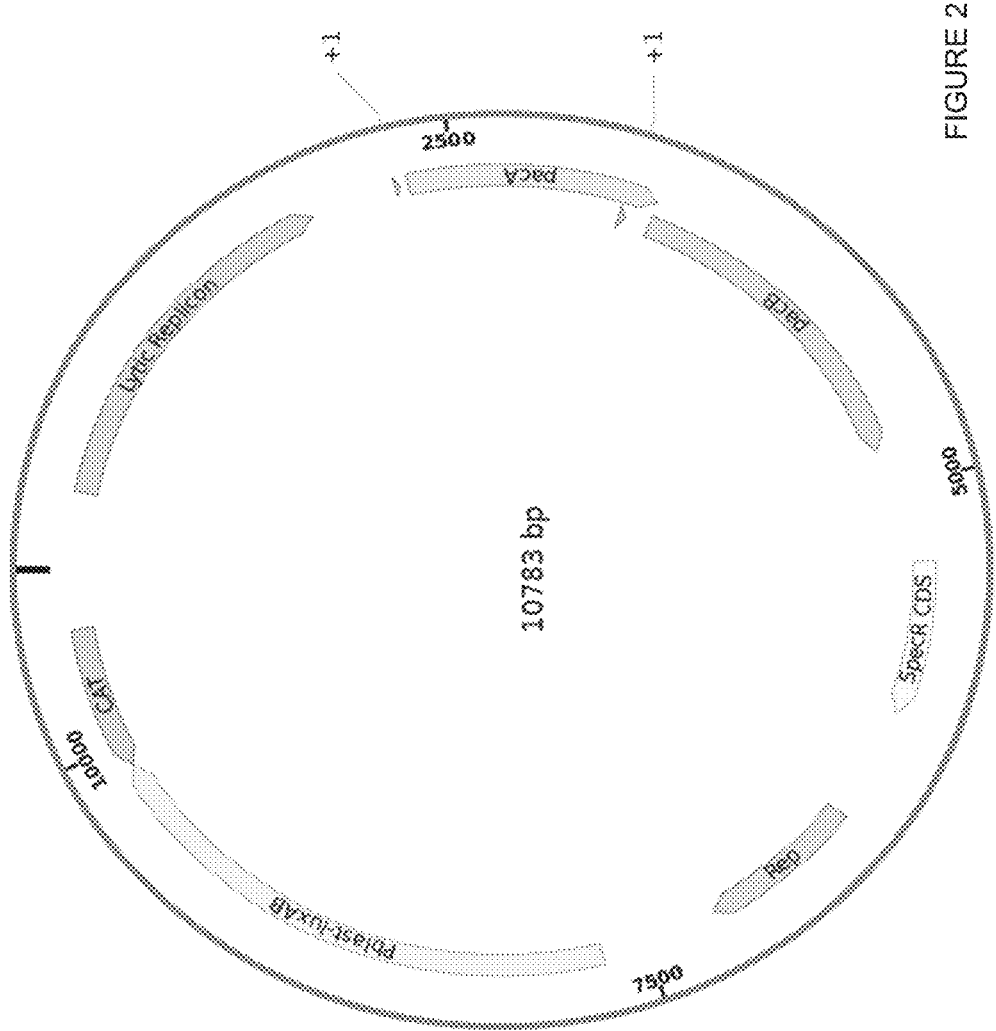
FIG. 2 illustrates a schematic of a complementing reporter plasmid carrying pacA and pacB genes under the control of the native pacA gene promoter, according to an embodiment.
Figure 3:
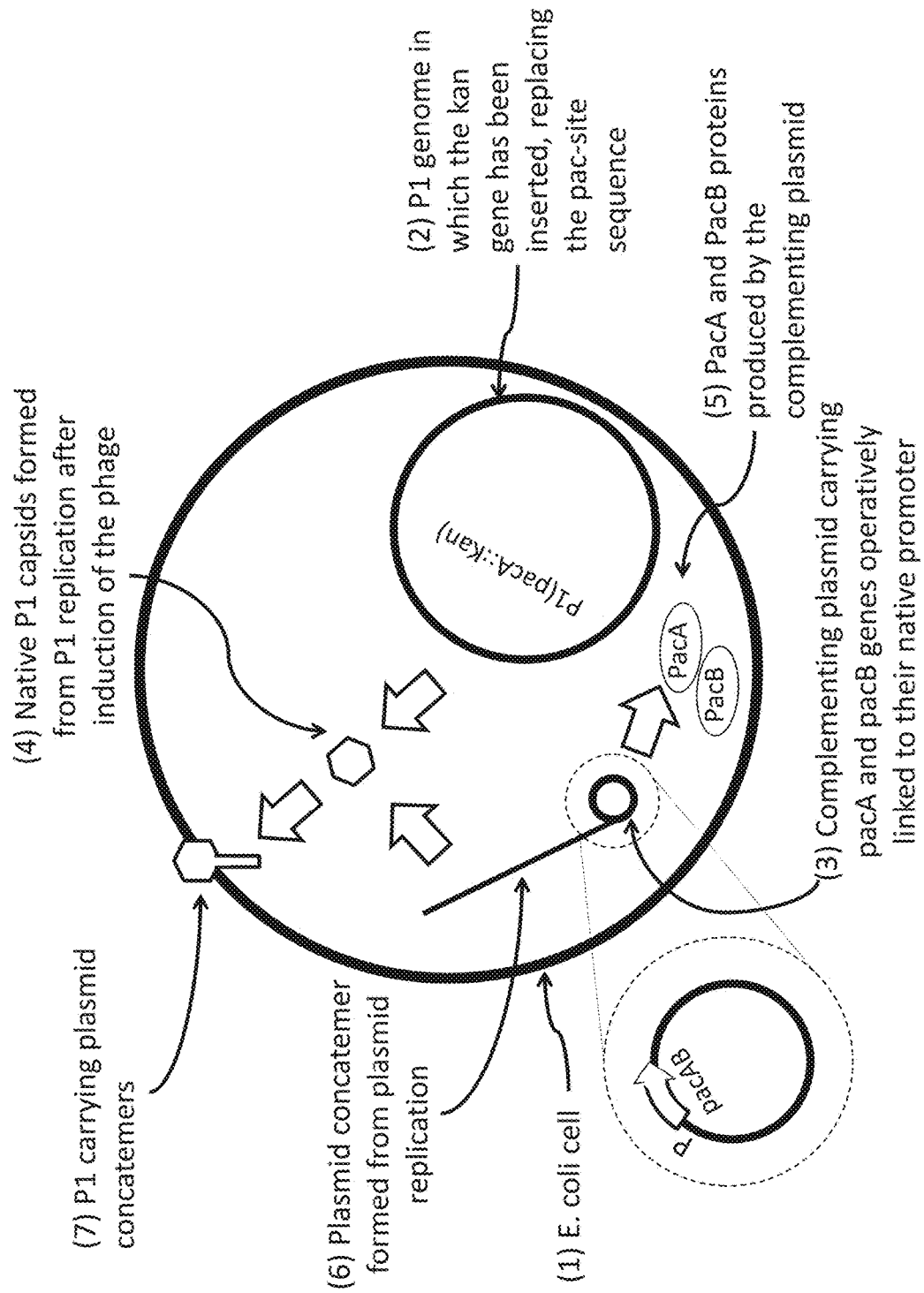
FIG. 3 illustrates an example of the design and function of a packaging system comprising an E. coli cell lysogenized with bacteriophage P1 having a disrupted pacA, the cell also carrying a plasmid containing pacA and pacB, according to an embodiment.

FIG. 2 illustrates a schematic of a plasmid carrying the pacA and pacB genes. FIG. 3 illustrates an example of the design and function of a packaging system composed of an *E. coli* cell lysogenized with the bacteriophage P1 having a disrupted pacA gene. The cell also carries a plasmid that contains the pacA and pacB genes. In an embodiment, the pacA and pacB genes in the plasmid are derived from Enterobacteriaceae bacteriophage P1. When the mutated virus is undergoing a lytic cycle, the viral packaging proteins produced either from the bacteriophage genome or (if disrupted) the complementing plasmid, package a replicon of the plasmid DNA into the packaging unit because of its packaging initiation site, and non-replicative transduction particles are produced carrying the replicated plasmid DNA.

In an embodiment, the replicon is an Enterobacteriaceae bacteriophage P1 lytic replicon. The replicon can also be a pBHR1 replicon or a derivative of the pBHR1 replicon, derived from an *S. aureus* pT181 plasmid origin of replication, derived from an *Enterococcus* repB plasmid origin of replication, or derived from an *Enterococcus* pDL278 plasmid origin of replication. In another embodiment, the replicon includes a C1 repressor-controlled P53 promoter, a promoter P53 antisense, a repL gene, and an in-frame deletion of a kilA gene. One example of a replicon has the sequence of SEQ ID NO: 2, SEQ ID NO: 3, SEQ ID NO: 5, SEQ ID NO: 7, or SEQ ID NO: 8.

In some embodiments, it is preferable that the disruption/complementation is designed such that there is no homology between the mutated virus DNA and the complementing exogenous DNA. This is because lack of homology between the mutated virus DNA and the complementing exogenous DNA avoids the possibility of homologous recombination between the two DNA molecules that can result in re-introduction of a packaging sequence into the virus genome. To accomplish a lack of homology, one strategy is to delete the entire gene (or genes) that contains the packaging initiation site sequence from the virus genome and then complement this gene with an exogenous DNA molecule that preferably contains no more than exactly the DNA sequence that was deleted from virus. In this strategy, the complementing DNA molecule is designed to express the gene that was deleted from the virus. Another example of such a system is provided using the bacteriophage φ80α, a pac-type phage. The phage genome is lysogenized in a host bacterial cell, and the phage genome includes a small terminase gene where the pac-site of a pac-type prophage φ80α has been deleted. A plasmid including a complementary small terminase gene with a native pac-site is transformed into the cell. When the lytic cycle of the lysogenized prophage is induced, the bacteriophage packaging system packages plasmid DNA into progeny bacteriophage structural components, rather than packaging the native bacteriophage DNA. The packaging system thus produces non-replicative transduction particles carrying plasmid DNA.

In another embodiment, a region of the bacteriophage genome is disrupted by an insertion that disrupts the packaging initiation site. In one embodiment, the disruption comprises reporter gene incorporated into the bacteriophage genome. In one embodiment, the disruption comprises a resistance marker and a reporter gene incorporated into the bacteriophage genome. In one embodiment, the disruption is accomplished by an allelic exchange event that replaces or disrupts a sequence on the bacteriophage genome with a reporter gene. In one embodiment, the disruption is accomplished by an allelic exchange event that replaces or disrupts a sequence on the bacteriophage genome with a resistance marker and a reporter gene. In some embodiments, the resistance marker and/or reporter gene are under the control of a constitutive promoter.

Figure 4:
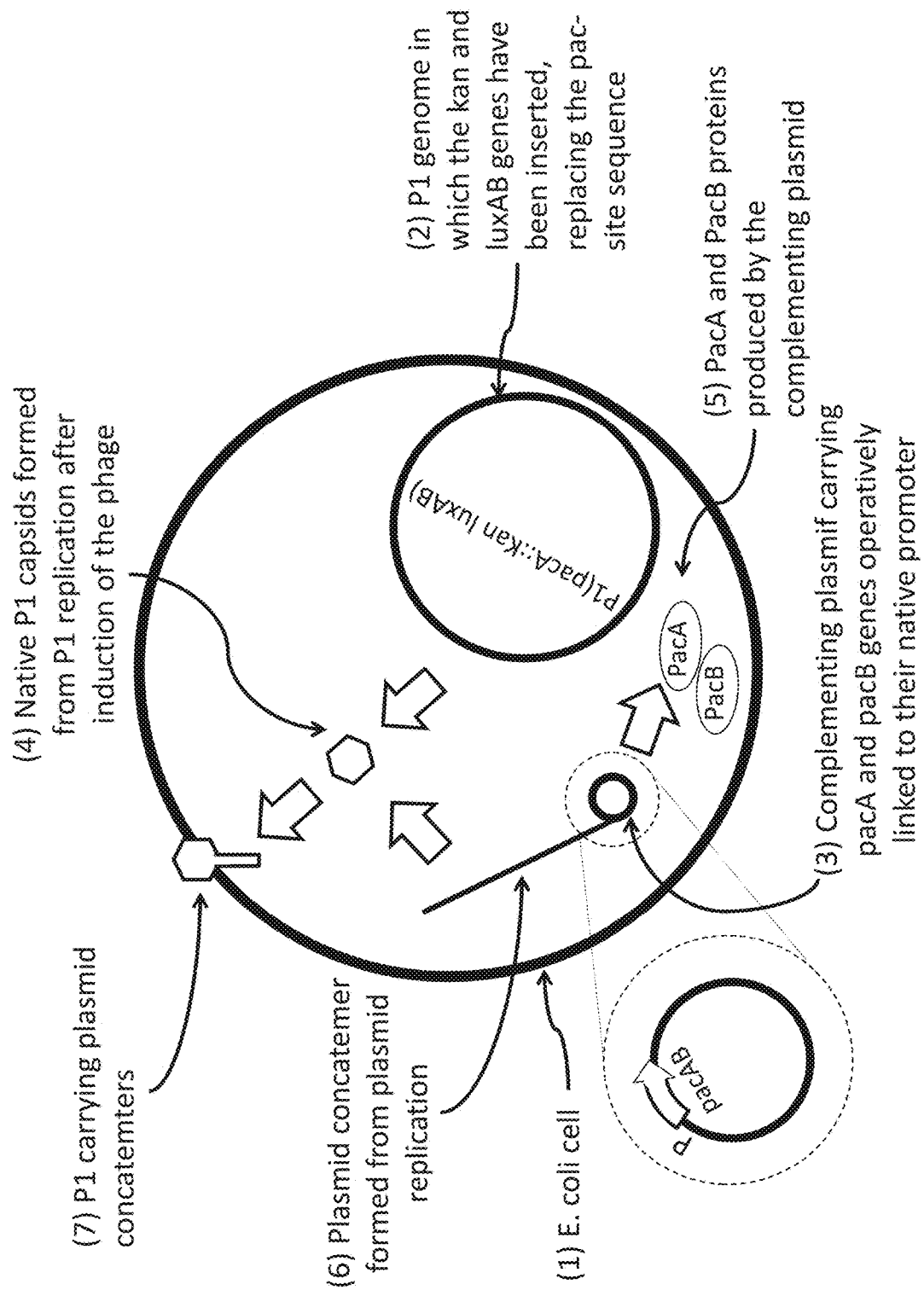
FIG. 4 illustrates an example of the design and function of a packaging system comprising an E. coli cell lysogenized with bacteriophage P1 having a disrupted pacA where the disruption is accomplished via the insertion of a kanamycin resistance gene and the bacterial luciferase luxAB genes, the cell also carrying a plasmid containing pacA and pacB, according to an embodiment.

FIG. 4 illustrates an example of the design and function of a packaging system composed of an *E. coli* cell comprising bacteriophage P1 having a disrupted pacA gene in which the kan and luxAB genes have been inserted into the pac-site sequence. As in FIG. 3, the cell also carries a plasmid that contains the pacA and pacB genes. Therefore, if recombination occurs between the bacteriophage and the plasmid, the replicated plasmid inserted into the P1 capsid to form the NRTP will still comprise a reporter gene.

In an embodiment, the reporter gene encodes a detectable marker or a selectable marker. In a further embodiment, said reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3×-FLAG), and selectable markers (ampC, tet(M), CAT, erm). In an embodiment, the reporter gene is luxA. In some embodiments, the resistance marker comprises an antibiotic resistance gene. In some embodiments, the resistance marker is a kanamycin resistance gene (kan). In some embodiments, the constitutive promoter comprises Pblast. In some embodiments, the bacteriophage genome disruption is accomplished by an allelic exchange event that replaces or disrupts a sequence on the bacteriophage genome that contains the packaging initiation site sequence.

In some embodiments, the bacteriophage genome disruption is accomplished by an allelic exchange event that replaces or disrupts a sequence on the bacteriophage genome that contains the packaging initiation site sequence with a kanamycin resistance gene (kan) and the bacterial luciferase genes (luxAB) under the control of a constitutive promoter (Pblast). In one embodiment, the allelic exchange is accomplished in a manner analogous to that depicted in FIG. 1, wherein a reporter or a reporter and a resistance marker are transferred.

In an embodiment, a pair of terminase genes on a bacteriophage genome, e.g., pacA and pacB, terA and terB, or terS and terL, are disrupted in a manner that causes polar effects that also disrupt expression of one of the terminase genes and/or overall terminase function mediated by the terminase genes. In one embodiment, a construct comprising kan and luxAB inserted into the pacA gene loci is provided in SEQ ID NO: 12. In one embodiment, the disrupted bacteriophage is complemented with a plasmid comprising terminase genes, e.g., pacA and pacB, terA and terB, or terS and terL, of the bacteriophage genome. In one embodiment, the plasmid is introduced into a cell lysogenized with the bacteriophage having the disrupted terminase genes. In one embodiment, the cell is an *E. coli* cell. In one embodiment, the bacteriophage is Enterobacteriaceae bacteriophage P1. In one embodiment, the terminase genes in the plasmid are derived from Enterobacteriaceae bacteriophage P1, i.e., pacA and pacB genes. When the mutated virus is undergoing a lytic cycle, the viral packaging proteins, produced either from the bacteriophage genome or (if disrupted) the complementing plasmid, package a replicon of the plasmid DNA into the packaging unit because it contains a packaging initiation site, and non-replicative transduction particles are produced carrying the replicated plasmid DNA.

In these deletion/complementation systems, two species of transduction particles may be produced including (1) non-replicative transduction particles carrying plasmid DNA and (2) non-replicative transduction particles carrying P1 DNA where the latter may be produced due to recombination between the plasmid DNA and the P1 DNA. In an embodiment where the P1 mutant does not contain luxAB inserted into the P1 genome, the non-replicative transduction particles carrying P1 DNA do not contribute to signal production when these transduction particles deliver DNA into target cells. However, in an embodiment where the P1 mutant does contain luxAB inserted in the P1 genome, the non-replicative transduction particles carrying P1 DNA do contribute to signal production when these transduction particles deliver DNA into target cells.

As such, an embodiment where the luxAB genes are inserted into the P1 genome results in an improved non-replicative transduction particle reporter system.

IV. Reporters

In some embodiments, the NRTPs and constructs of the invention comprise a reporter nucleic acid molecule including a reporter gene. In some embodiments, the bacteriophage of the invention includes a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, ruc, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag, 3×-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Reporters and reporter assays are described further in Section V herein.

NRTPs and Reporter Assays

Inducer Reporter Assay

In some embodiments, the invention comprises methods for the use of NRTPs as reporter molecules for use with endogenous or native inducers that target gene promoters within viable cells. The NRTPs of the invention can be engineered using the methods described in Section III and below in Examples 1-2.

In some embodiments, the method comprises employing a NRTP as a reporter, wherein the NRTP comprises a reporter gene that is operably linked to an inducible promoter that controls the expression of a target gene within a target cell. When the NRTP that includes the reporter gene is introduced into the target cell, expression of the reporter gene is possible via induction of the target gene promoter in the reporter nucleic acid molecule.

Figure 5:
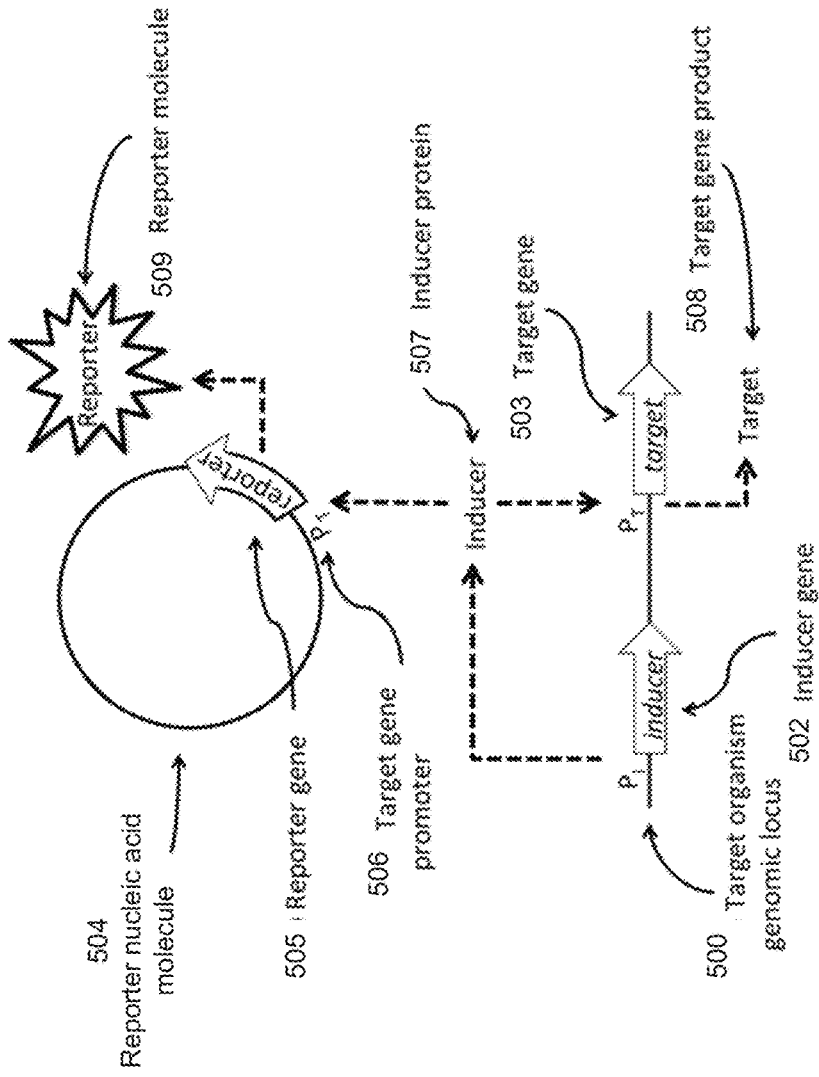
FIG. 5 depicts a system for the use of NRTPs for the detection of inducers to target gene promoters within viable cells, according to an embodiment of the invention.
Figure 6:
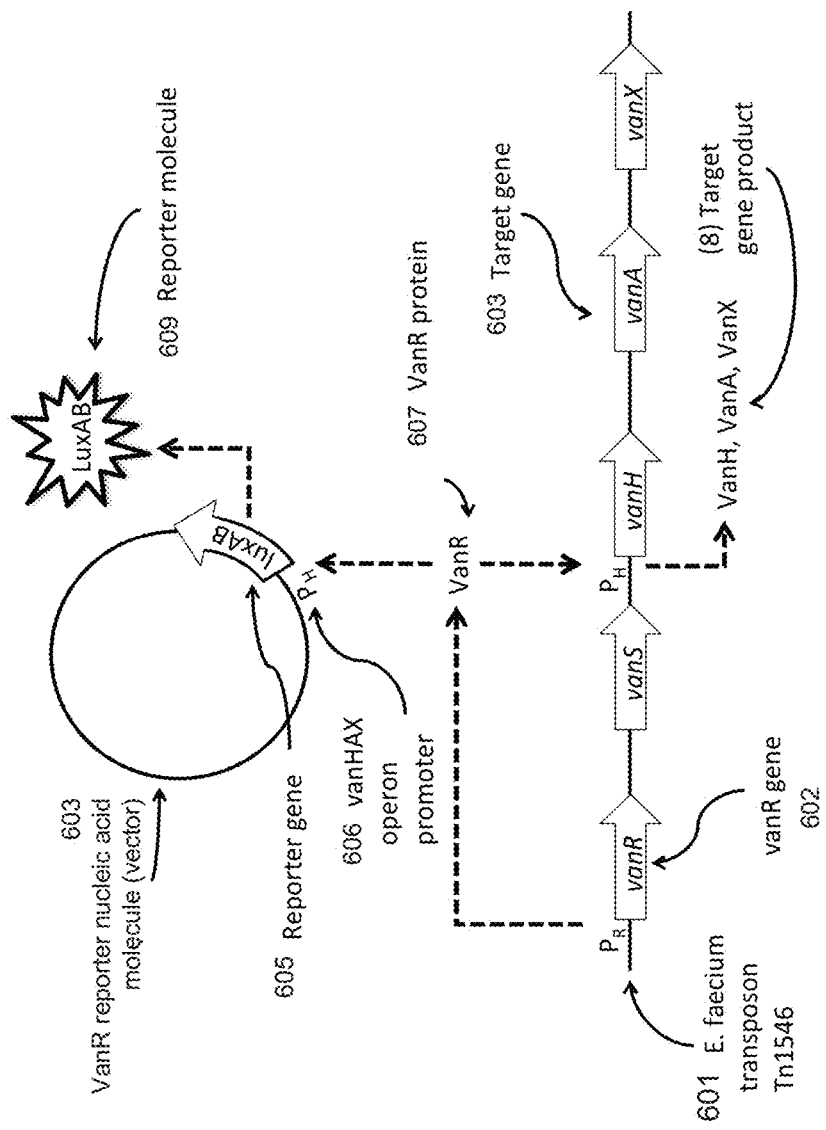
FIG. 6 depicts a reporter system that includes a reporter nucleic acid molecule (e.g., plasmid) that is constructed for detecting VanR, the inducer of the promoter of the vancomycin resistance (vanA) gene in Enterococcus faecium (or E. faecalis), according to an embodiment of the invention. The reporter plasmid carries a reporter gene that is operatively linked to the vanA gene promoter.
Figure 7:
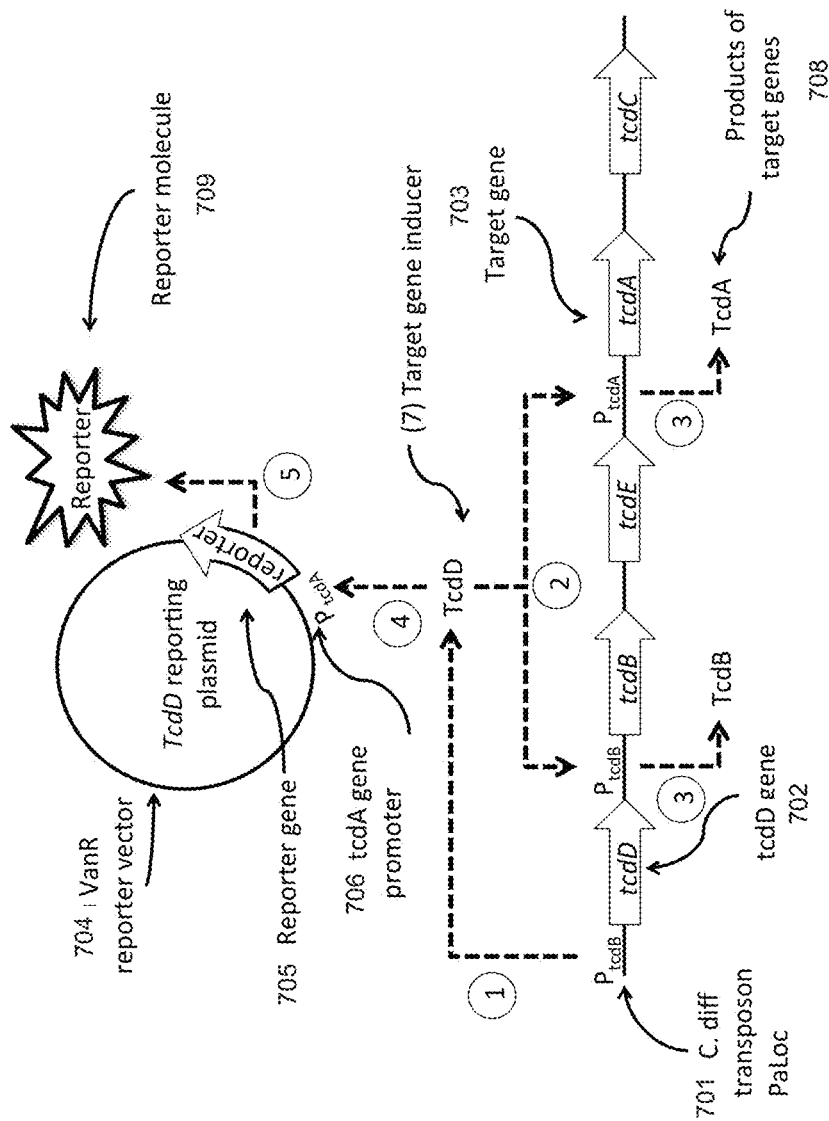
FIG. 7 depicts a reporter system that includes a reporter nucleic acid molecule constructed for detecting TcdD, the inducer of the promoters of the toxins A and B genes (tcdA and tcdB, respectively) of C. difficile, according to an embodiment of the invention. The reporter nucleic acid molecule includes a reporter gene that is operatively linked to the tcdA gene promoter.
Figure 8:
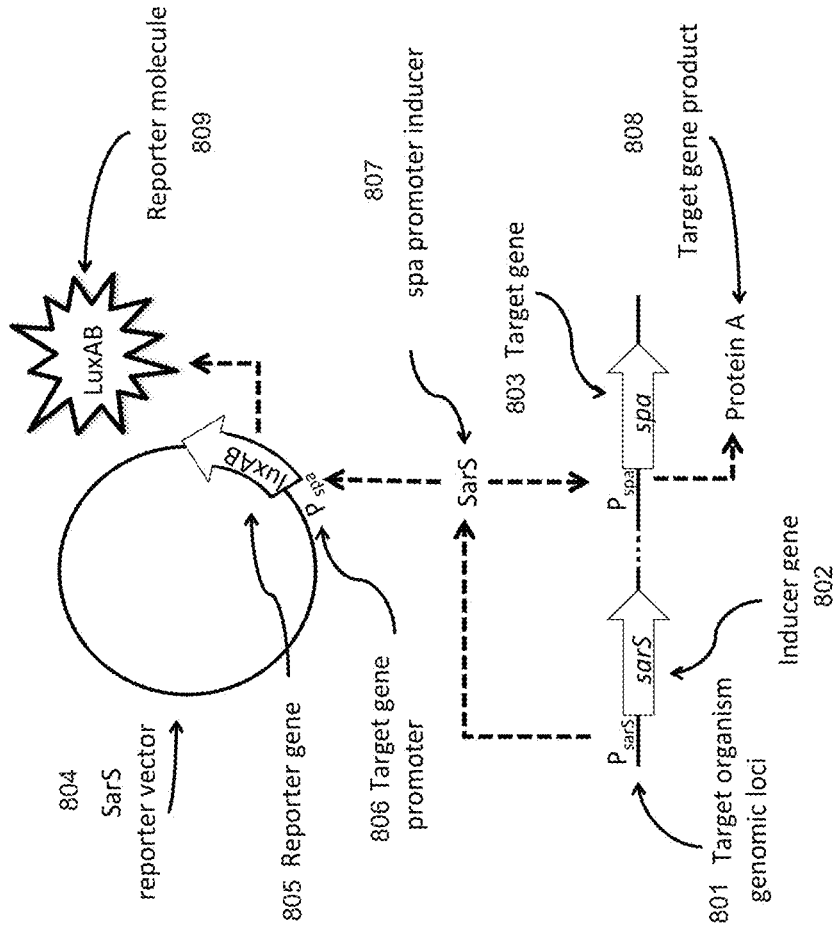
FIG. 8 depicts a reporter system that includes a reporter nucleic acid molecule is constructed for detecting SarS, the inducer of the promoter of the Protein A gene (spa) in S. aureus, according to an embodiment of the invention. The reporter nucleic acid molecule includes the bacterial luciferase genes luxA and luxB operatively linked to the spa gene promoter ($P_{spa}$).

FIG. 5 depicts a genomic locus of a target cell 500 with two genes, a gene encoding an inducer 502 and a target gene 503. Also depicted is a reporter nucleic acid molecule 504 that includes a reporter gene 505 that is operatively linked to the promoter 506 of the target gene of the target cell. The reporter nucleic acid molecule 504 can be introduced into the cell via a NRTP. In the native cell, when the inducer gene 502 is expressed and produces the inducer protein 507, the inducer protein 507 is able to induce the target gene promoter 506 that is operatively linked to the target gene, thus causing the expression of the target gene and the production of the target gene product 508.

When the reporter nucleic acid molecule 504 is present within the target organism, the inducer 507 is also able to induce the target gene promoter 506 present within the reporter nucleic acid molecule 504, thus causing the expression of the reporter gene 505 resulting in the production of a reporter molecule 509 capable of generating a detectable signal.

Thus, the production of a detectable signal from the reporter molecule 509 is indicative of the presence of the cell, based on the presence of the inducer protein 507 within a target cell.

VanR Reporter System

In one embodiment, the reporter system includes NRTP comprising a reporter nucleic acid molecule (e.g., plasmid). The reporter nucleic acid molecule can be constructed for detecting VanR, the inducer of the promoter of the vancomycin resistance (vanA) gene in *Enterococcus faecium* (or *E. faecalis*). The reporter plasmid carries a reporter gene that is operatively linked to the vanA gene promoter.

FIG. 6 outlines the design and function of a VanR reporter system. FIG. 6 depicts a region of the transposon Tn1546 601 that may be present in *E. faecium*. The Tn1546 transposon can include the vanR inducer gene 602 and the vanA target gene 603. Also depicted in the figure is a reporter nucleic acid molecule 604 that can be packaged in a NRTP and introduced into the cell. The reporter nucleic acid molecule 604 includes a reporter gene 605 that is operatively linked to a promoter $P_H$ 606 that controls the expression of the vanHAX operon that includes the vanA gene. In the native cell, when the vanR gene 602 is expressed and produces the VanR protein 607, VanR is able to induce $P_H$ 606 in the Tn1546 transposon, thus causing the expression of the vanA gene and thus producing the VanA protein 608. When the reporter nucleic acid molecule 603 (vector) is present within the target organism, VanR is also able to induce $P_H$ 606 within the reporter nucleic acid molecule 603, thus causing the expression of a reporter molecule 609. Thus, the production of a reporter molecule is indicative of the presence of VanR within a target cell.

Examples of promoters that are suitable for the development of a VRE assay include: the vanA gene promoter and a vanB gene promoter. Arthur, M., et al., *The VanS sensor negatively controls VanR-mediated transcriptional activation of glycopeptide resistance genes of Tn1546 and related elements in the absence of induction*. J. Bacteriol., 1997. 179(1): p. 97-106.

TcdD Reporter System

In another embodiment of this system, a reporter nucleic acid molecule is introduced into a cell using a NRTP. The reporter nucleic acid molecule can be constructed for detecting TcdD, the inducer of the promoters of the toxins A and B genes (tcdA and tcdB, respectively) of *C. difficile*. The reporter nucleic acid molecule includes a reporter gene that is operatively linked to the tcdA gene promoter.

FIG. 7 outlines the design and function of a TcdD reporter system, according to an embodiment of the invention. FIG. 7 depicts a region of the transposon PaLoc 701 that may be present in *C. difficile*. The PaLoc transposon may contain the tcdD gene 702 and the tcdA target gene 703. Also depicted in the figure is a reporter nucleic acid molecule 704 (e.g., vector) that is introduced into the cell using a NRTP. The reporter nucleic acid molecule 704 includes the reporter gene 705 that operatively linked to the tcdA gene promoter ($P_{tcdA}$) 706.

In the native cell, when the tcdD gene is expressed and produces the TcdD protein 707, TcdD is able to induce $P_{tcdA}$ 706 in the PaLoc transposon 701, thus causing the expression of the tcdA gene 703 and thus producing the toxin A protein 708.

When the reporter nucleic acid molecule 704 is present within the target organism, TcdD is also able to induce $P_{tcdA}$ 706 within the reporter vector, thus causing the expression of a reporter molecule 709. Thus, the production of a reporter molecule 709 is indicative of the presence of TcdD within a target cell.

Examples of promoters suitable for the development of a *C. difficile* assay include: the tcdA gene promoter and the tcdB gene promoter. Karlsson, S., et al., *Expression of Clostridium difficile Toxins A and B and Their Sigma Factor TcdD Is Controlled by Temperature*. Infect. Immun., 2003. 71(4): p. 1784-1793.

Target cells and inducers: Target cells can include eukaryotic and prokaryotic cell targets and associated inducers.

Vector delivery systems: The delivery of the vector containing the recombinant DNA can by performed by abiologic or biologic systems. Including but not limited to liposomes, virus-like particles, transduction particles derived from phage or viruses, and conjugation.

Bacteriophage-Based SarS Reporter System

In another embodiment of the invention, a reporter nucleic acid molecule is constructed for detecting SarS, the inducer of the promoter of the Protein A gene (spa) in *S. aureus*. The reporter nucleic acid molecule can be introduced into the cell in a NRTP and includes the bacterial luciferase genes luxA and luxB operatively linked to the spa gene promoter ($P_{spa}$). The reporter nucleic acid molecule is delivered to *S. aureus* via a NRTP, for example. If SarS is present in the cell, it will induce the expression of the luxAB genes, thus producing luciferase enzyme that is capable of generating a luminescent signal.

FIG. 8 outlines the design and function of a SarS reporter system, according to one embodiment of the invention. FIG. 8 depicts a region of the *S. aureus* genome 801 that contain the sarS gene 802 and spa gene 803. Also depicted in the figure is a reporter nucleic acid molecule (e.g., vector) 804 delivered by NRTP to the cell and that includes the luxAB reporter genes 805 that operatively linked to the promoter $P_{spa}$ 806 that controls the expression of the spa gene 803.

In the native cell, when the sarS gene 802 is expressed, producing SarS protein 807, the protein is able to induce $P_{spa}$ 806 in the *S. aureus* genome transposon, thus causing the expression of the spa gene 803 and producing the Protein A 808.

When the reporter nucleic acid molecule 804 is present within the target organism, SarS 807 is also able to induce $P_{spa}$ 806 within the reporter nucleic acid molecule 804, thus causing the expression of luxAB resulting in the production of the luciferase enzyme 809 that can generate a luminescent signal. Thus, the production of luciferase is indicative of the presence of SarS within a target cell.

Other reporter systems for use with the NRTPs described herein are described in International PCT Publication Number: WO 2014/160418, incorporated herein by reference in its entirety.

Mechanism of Conformational Change by Cis-Repression of the Reporter Sequence and by Binding of a Target Transcript The general mechanisms employed in the invention are intermolecular nucleic acid molecule interactions that may result in two subsequent mechanisms: (1) a conformational change in the secondary structure of the nucleic acid molecules, and (2) a cleaving event. Described herein are methods for designing reporter transcripts that can undergo a conformational change between a cis-repressed conformation and a de-repressed conformation, such that the conformational change is induced by binding of a target transcript to the reporter transcript.

As described above, a reporter transcript can comprise a reporter sequence and be designed such that translation of the reporter gene sequence is blocked by cis-repression of the ribosome binding site (RBS) of the reporter gene.

In some embodiments, the following tools can be used for designing the reporter transcripts of the invention.
1) RNA secondary structure is calculated using secondary structure program, such as Mfold available at a server maintained by The RNA Institute College of Arts and Sciences, University at Albany, State University of New York (Mfold web server for nucleic acid folding and hybridization prediction. Nucleic Acids Res. 31 (13), 3406-15, (2003))
2) Intermolecular RNA interactions are calculated using a software program such as RNA-RNA InterACTion prediction using Integer Programming (RactIP) available at a server maintained by the Graduate School of Information Science, Nara Institute of Science and Technology (NAIST), Department of Biosciences and Informatics, Keio University Japan
3) RNA secondary structure is visualized using Visualization Applet for RNA (VARNA), which is a Java lightweight Applet dedicated to drawing the secondary structure of RNA.

A secondary structure of the target transcript can be generated based on the lowest energy conformation calculated by MFold and visualized with VARNA.

ssRNA regions or target regions can be identified within the target transcript that can be ideal for binding to a reporter transcript. In some instances, the secondary structure of the target transcript includes a consensus sequence or loop sequence that can bind to a portion of the reporter sequence. For example, in the mecA transcript of methicillin-resistant *S. aureus*, there is a terminal loop that includes a consensus YUNR sequence ("UUGG") that can be used to bind to a cis-repressing sequence of a reporter transcript. Analysis of the secondary structure of the target transcript can reveal these one or more ssRNA regions that can be suitable for binding to a cis-repressing sequence. The cis-repressing sequence of the reporter transcript can then be designed to bind to these one or more ssRNA regions.

In some embodiments, the cis-repressing sequence can be designed to bind to the RBS of the reporter sequence in the reporter transcript and form a stem-loop structure within the reporter transcript, such that the cis-repressing sequence blocks binding of an RNA polymerase to the RBS of the reporter sequence. Upon binding of the cis-repressing sequence to the ssRNA region of the target transcript, the RBS of the reporter sequence can be exposed and translation of the reporter sequence can be initiated.

Figure 9:
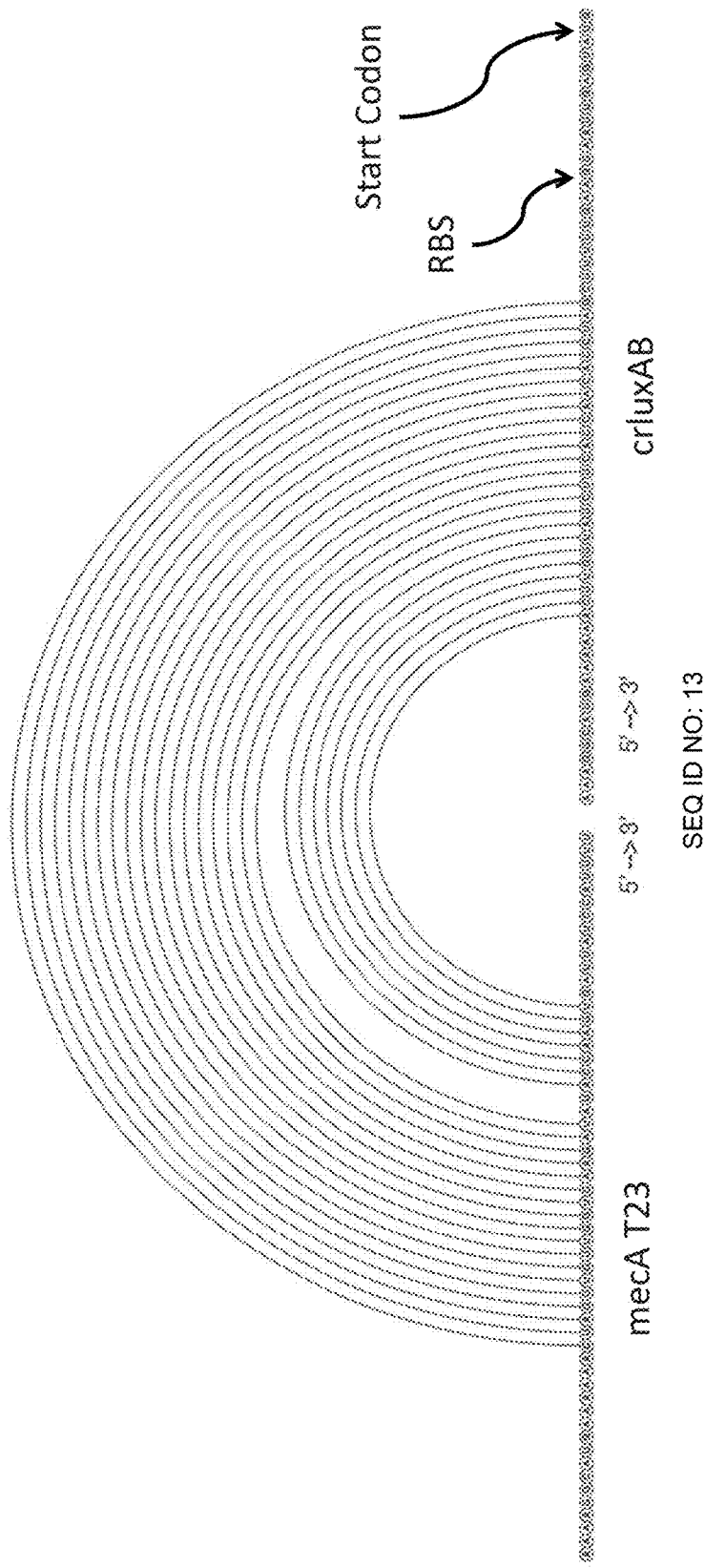
FIG. 9 shows a diagram of base pairing between the target transcript and the cis-repressing sequence of the reporter transcript SEQ ID NO: 13.

In some embodiments, the cis-repressing sequence of the reporter transcript can be designed to be positioned at the 5' terminus of the reporter sequence and designed to generate a stem-loop structure in the reporter sequence, such that the RBS sequence of the reporter sequence is blocked. The cis-repressing stem-loop structure can be designed to block the RBS sequence based on the lowest energy conformation of the reporter transcript, as calculated by MFold and visualized with VARNA. The predicted inter-molecular interactions between the target transcript and the cis-repressing sequence of the reporter transcript can be calculated by RactIP and visualized by VARNA. A diagram can be drawn to visualize the base pairing between the target transcript and the cis-repressing sequence of the reporter transcript (SEQ ID NO: 13), as shown in FIG. 9.

The interaction can include base pairing between 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in the target sequence and cis-repressing sequence. The complementary binding between the two sequences can be fully complementary, substantially complementary or partially complementary. The base pairing can be across contiguous nucleotide sequences or regions within the target and cis-repressing sequences, for example, as shown in FIG. 9.

Transcripts

As described above, a transcript is a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be transcribed from an engineered nucleic acid construct. The transcript can have regions of complementarity within itself, such that the transcript includes two regions that can form an intra-molecular duplex. One region can be referred to as a "cis-repressing sequence" that binds to and blocks translation of a reporter sequence. A second region of the transcript is called a "reporter sequence" that encodes a reporter molecule, such as a detectable or selectable marker.

The transcripts of the invention can be a transcript sequence that can be 5, 6, 7, 8, 9, 10, 11, 12, 13, 14, 15, 16, 17, 18, 19, 20, 21, 22, 23, 24, or 25 nucleotides in length. In other embodiments, the transcript can be at least 25, 30, 40, 50, 60, 70, 80, 90, 100, 500, 1000, 1500, 2000, 3000, 4000, 5000 or more nucleotides in length. The cis-repressing sequence and the reporter sequence can be the same length or of different lengths.

In some embodiments, the cis-repressing sequence is separated from the reporter sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, or more spacer nucleotides.

Vectors

In another aspect, the transcripts (including antisense and sense sequences) of the invention are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These sequences can be introduced as a linear construct, a circular plasmid, or a viral vector, including bacteriophage-based vectors, which can be incorporated and inherited as a transgene integrated into the host genome. The transcript can also be constructed to permit it to be inherited as an extrachromosomal plasmid (Gassmann, et al., *Proc. Natl. Acad. Sci. USA* (1995) 92:1292).

The transcript sequences can be transcribed by a promoter located on the expression plasmid. In one embodiment, the cis-repressing and reporter sequences are expressed as an inverted repeat joined by a linker polynucleotide sequence such that the transcript has a stem and loop structure.

Recombinant expression vectors can be used to express the transcripts of the invention. Recombinant expression vectors are generally DNA plasmids or viral vectors. Viral vectors expressing the transcripts can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the transcript(s) to be expressed can be used, for example, vectors derived from adenovirus (AV); adeno-associated virus (AAV); retroviruses (e.g., lentiviruses (LV); Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the transcripts into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. A suitable AV vector for expressing the transcripts featured in the invention, a method for constructing the recombinant AV vector, and a method for delivering the vector into target cells, are described in Xia H et al. (2002), *Nat. Biotech.* 20: 1006-1010. Suitable AAV vectors for expressing the transcripts featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving transcript expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transcript can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D-1-thiogalactopyranoside (IPTG). A person skilled in the art would be able to choose the appropriate regulatory/promoter sequence based on the intended use of the dsRNA transgene.

Generally, recombinant vectors capable of expressing transcript molecules are delivered as described below, and persist in target cells. Alternatively, viral vectors can be used that provide for transient expression of transcript molecules. Such vectors can be repeatedly administered as necessary. Once expressed, the transcript binds to target RNA and modulates its function or expression. Delivery of transcript expressing vectors can be systemic, such as by intravenous or intramuscular administration, by administration to target cells ex-planted from the patient followed by reintroduction into the patient, or by any other means that allows for introduction into a desired target cell.

Transcript expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single PROC gene or multiple PROC genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The delivery of the vector containing the recombinant DNA can by performed by abiologic or biologic systems. Including but not limited to liposomes, virus-like particles, transduction particles derived from phage or viruses, and conjugation.

Reporters for Transcript Assay

In some embodiments, the nucleic acid construct comprises a reporter sequence (e.g., a reporter gene sequence). The reporter gene encodes a reporter molecule that produces a signal when expressed in a cell. In some embodiments, the reporter molecule can be a detectable or selectable marker. In certain embodiments, the reporter molecule can be a fluorescent reporter molecule, such as a green fluorescent protein (GFP), yellow fluorescent protein (YFP), cyan fluorescent protein (CFP), blue fluorescent protein (BFP), or red fluorescent protein (RFP). In other embodiments, the reporter molecule can be a chemiluminescent protein.

Reporter molecules can be a bacterial luciferase, an eukaryotic luciferase, a fluorescent protein, an enzyme suitable for colorimetric detection, a protein suitable for immunodetection, a peptide suitable for immunodetection or a nucleic acid that function as an aptamer or that exhibits enzymatic activity.

Selectable markers can also be used as a reporter. The selectable marker can be an antibiotic resistance gene, for example.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Allelic Exchange-Based Disruption/Complementation Packaging System

The following is an example of the design and construction of an allelic exchange-based disruption/complementation-based packaging system for producing non-replicative transduction particles.

The materials used for developing the packaging system are listed below:

Bacterial Strains:
N1706, an *E. coli* K-12 P1 c1-100 Tn9 lysogen
Vectors:
Y14439 (pBHR1 backbone)
The following GenBank accession numbers (N.B., the sequences referred to by accession number are those listed in the database as of the priority date of this application) or SEQ ID NOs. can be used for the vector backbone and cassette sequences:
X06758 (bacterial luciferase genes luxAB)
SEQ ID NO:1 (Native P1 pacA and pacB genes including the native pacA gene promoter)
SEQ ID NO:2 (P1 lytic replicon containing the C1 repressor-controlled P53 promoter, the promoter P53 antisense, the repL genes, and an in-frame deletion of the kilA gene)
SEQ ID NO:11 (Pblast promoter driving luxAB expression)

Construction of N1706(pacA::Kan): pacA Mutated Strain Aka Strain 1505:

An exemplary sequence of a pacA mutated sequence is shown in SEQ ID NO: 10. The mutation was accomplished by constructing an allelic exchange substrate comprised of the kanamycin resistance gene flanked by pacA gene sequences that themselves flank the sequence of the pacA gene that is desired to be replaced. The allelic exchange substrate was produced via gene synthesis and by replacing the native sequence in N1706 and inserting the Kan gene via an allelic exchange. It was determined that the disruption also disrupted the ability of the mutated P1 phage to package DNA. Induction of the mutated phage resulted in elimination of the progeny phage as determined from comparing P1 phage titers via plaque assay from cell lysates produced by inducing the native phage versus the mutated phage. Furthermore, when complementing plasmid expressing the pacA gene was introduced into the P1 mutant lysogen and the mutant phage was induced from the transformant, transduction particles were not recovered in the lysate indicating that the phage was not able to package the complementing plasmid despite it complementing the pacA gene and pac-site.

Construction of the Complementing Plasmid:

The complementing plasmid contained the pBHR1 origin of replication exhibiting broad Gram-negative activity, a selectable marker for spectinomycin, the native bacteriophage P1 pacA and pacB genes operatively linked to the native pacA gene promoter sequence. Also contained were the luxA and luxB genes from *Aliivibrio fischeri* operatively linked to the constitutive blasticillin promoter (Pblast), and the P1 lytic replicon containing the C1 repressor-controlled P53 promoter, the promoter P53 antisense, the repL genes, and an in-frame deletion of the kilA gene.

The plasmid can be constructed in a variety of manners that are known to one of skill in the art including obtaining the cassettes via PCR from their native sources or via gene synthesis and assembly of the vector via traditional restriction enzyme-based cloning or alternative techniques such as Gibson assembly.

Complementation-Based Packaging System:

The packaging system included the pacA mutant strain 1505 complemented with the complementing plasmid. As known to one of skill in the art, the manner of constructing this system can be accomplished by transformation of 1505 with the complementing plasmid. The complementing plasmid was maintained in cultures of the transformed 1505 by growing the transformant in the presence of 10 ug/mL of spectinomycin.

Production of Transduction Particles Carrying Plasmid DNA:

Non-replicative transduction particles carrying the complementing plasmid were produced from 1505 transformants via thermal induction at 42° C. Incubation at 42° C. resulted in induction of the P1 lytic cycle in which the prophage produced phage structural elements, and packaged the complementing plasmid concatameric DNA formed by the lytic replicon in progeny phage particles. Unlike complementation using a complementing plasmid that only expressed the pacA gene that did not result in the production of transduction particles, when both the pacA and pacB genes were disrupted in the bacteriophage genome, the complementing plasmid expressing both the pacA and pacB genes resulted in cell lysate containing non-replicative transduction particles, each consisting of bacteriophage P1 particles carrying a linear concatemer of the complementing plasmid and thus demonstrating that this complementing plasmid successfully complemented the disruption of packaging.

Example 2: Improved Allelic Exchange-Based Disruption/Complementation Packaging System In an example employing an Enterobacteriaceae bacteriophage P1 comprising terminase genes pacA and pacB, pacA was disrupted in a manner that causes polar effects that also disrupt pacB expression and/or overall terminase function mediated by PacA and PacB. The construct sequence in which kan and luxAB were inserted into the pacA gene loci is shown in SEQ ID NO:12.

The pacAB disrupted bacteriophage genome was then complemented with the plasmid depicted in FIG. 2. FIG. 4 illustrates the design and function of a packaging system composed of an *E. coli* cell lysogenized with the bacteriophage P1 having a disrupted pacA gene. The cell also contained a plasmid that comprised the pacA and pacB genes. In this example, the pacA and pacB genes in the plasmid were derived from Enterobacteriaceae bacteriophage P1. When the mutated virus was in the lytic cycle, the viral packaging proteins were produced from the complementing plasmid, which packaged a replicon of the plasmid DNA into the packaging unit because of its packaging initiation site, and non-replicative transduction particles were produced carrying the replicated plasmid DNA.

In these deletion complementation systems, two species of transduction particles were produced including (1) non-replicative transduction particles carrying plasmid DNA and (2) non-replicative transduction particles carrying P1 DNA where the latter may be produced due to recombination between the plasmid DNA and the P1 DNA. When the P1 mutant did not contain luxAB inserted in the pacA gene, the non-replicative transduction particles carrying P1 DNA did not contribute to signal production when these transduction particles deliver DNA into target cells. However, when the P1 mutant did contain luxAB inserted in the pacA gene, the non-replicative transduction particles carrying P1 DNA did contribute to signal production when these transduction particles deliver DNA into target cells (see FIG. 10).

Therefore, when the luxAB genes were inserted into the P1 genome and integrated with the NRTP generating system described herein, an improved non-replicative transduction particle reporter system was generated.

The following provides further details of the design and construction of the allelic exchange-based disruption/complementation-based packaging system for producing non-replicative transduction particles described in this example.

The materials used for developing the packaging system are listed below:

Bacterial Strains:
N1706, an *E. coli* K-12 P1 c1-100 Tn9 lysogen
Vectors:
Y14439 (pBHR1 backbone)
The following GenBank accession numbers (N.B., the sequences referred to by accession number are those listed in the database as of the priority date of this application) or SEQ ID NOs. can be used for the vector backbone and cassette sequences:

X06758 (bacterial luciferase genes luxAB)
SEQ ID NO:1 (Native P1 pacA and pacB genes including the native pacA gene promoter)
SEQ ID NO:2 (P1 lytic replicon containing the C1 repressor-controlled P53 promoter, the promoter P53 antisense, the repL genes, and an in-frame deletion of the kilA gene)
SEQ ID NO:11 (Pblast promoter driving luxAB expression)

Construction of N1706(pacA::Kan luxAB): pacA Mutated Strain Aka Strain 1525: was Performed as Follows:

An exemplary sequence of a mutated pacA sequence is shown in SEQ ID NO: 12. A pacA mutated sequence as provided in SEQ ID NO: 12 was generated by constructing an allelic exchange substrate comprised of the kanamycin resistance gene (Kan) and luxAB genes under the control of the Pblast promoter and flanked by pacA gene sequences that themselves flank the sequence of the pacA gene. The allelic exchange substrate was produced via gene synthesis. Then, the native pacA sequence in N1706 was replaced via insertion of the Kan and luxAB genes via an allelic exchange. It was determined that the disruption also disrupted the ability of the mutated P1 phage to package DNA. Induction of the mutated phage resulted in elimination of the progeny phage as determined from comparing P1 phage titers via plaque assay from cell lysates produced by inducing the native phage vs. the mutated phage.

Construction of the Complementing Plasmid:

The complementing plasmid contained the pBHR1 origin of replication exhibiting broad Gram-negative activity, a selectable marker for spectinomycin, the native bacteriophage P1 pacA and pacB genes operatively linked to the native pacA gene promoter sequence, the luxA and luxB genes from *Aliivibrio fischeri* operatively linked to the constitutive blasticillin promoter (Pblast), the P1 lytic replicon containing the C1 repressor-controlled P53 promoter, the promoter P53 antisense, the repL genes, and an in-frame deletion of the kilA gene.

The plasmid can be constructed in a variety of manners that are known to one of skill in the art including obtaining the cassettes via PCR from their native sources or via gene synthesis and assembly of the vector via traditional restriction enzyme-based cloning or alternative techniques such as Gibson assembly.

Complementation-Based Packaging System:

The packaging system included the pacA mutant strain 1525 complemented with the complementing plasmid. As known to one of skill in the art, the manner of constructing this system can be accomplished by transforming strain 1525 with the complementing plasmid. The complementing plasmid can be maintained in cultures of the transformed 1525 by growing the transformant in the presence of 10 ug/mL of spectinomycin.

Production of Transduction Particles Carrying Plasmid DNA:

Non-replicative transduction particles carrying the complementing plasmid were produced from 1525 transformants via thermal induction at 42° C. Incubation at 42° C. resulted in induction of the P1 lytic cycle in which the prophage produced phage structural elements, and packaged the complementing plasmid concatameric DNA formed by the lytic replicon in progeny phage particles. The complementing plasmid expressing both the pacA and pacB genes resulted in cell lysate containing non-replicative transduction particles, each consisting of bacteriophage P1 particles carrying a linear concatemer of the complementing plasmid and thus demonstrating that this complementing plasmid successfully complemented the disruption of packaging.

In addition to transduction particles carrying plasmid DNA, the system produced transduction particles carrying P1 DNA. Transduction particles carrying P1 DNA can arise via recombination between the plasmid DNA and P1 DNA. The presence of transduction particles carrying P1 DNA was assessed by exposing target cells to lysate from this system and screening for the presence of transduced cells that propagate on selective media that incorporates kanamycin while transduction particles carrying plasmid DNA was assessed in a similar manner based on spectinomycin resistance. FIG. 10 shows a table of data obtained from measuring the light production (RLU) from colonies of transduced cells. Cells that were resistant to spectinomycin (SpecR) were transduced with plasmid DNA while cells that were resistant to kanamycin (KanR) were transduced by P1 DNA. Data from 1505 was obtained from packaging lines that do not have luxAB inserted into the P1 genome while that from 1525 was obtained from packaging lines that do have luxAB inserted into the P1 genome. As can be seen from the data, all SpecR transductants produced light while all of the KanR transductants produced light only for those transduced from 1525.

As such, 1525 represents an improved non-replicative transduction particle-based reporter system where transduction particles carrying both plasmid DNA and virus DNA are capable of producing light.

REFERENCES CITED

1. Michael G. Schmidt, D. A. S., Caroline Westwater, Joseph W. Dolan, Brian D. Hoel, Philip A. Werner, James S. Norris, Laura M. Kasman, Nucleic Acid Delivery and Expression, 2005.
2. Kreiswirth, B. N. et al., The toxic shock syndrome exotoxin structural gene is not detectably transmitted by a prophage. Nature, 1983. 305(5936): p. 709-712.
3. Ubeda, C. et al., Specificity of staphylococcal phage and SaPI DNA packaging as revealed by integrase and terminase mutations. Molecular Microbiology, 2009. 72(1): p. 98-108.
4. Otsuji, N. et al., Induction of Phage Formation in the Lysogenic *Escherichia coli* K-12 by Mitomycin C. Nature, 1959. 184(4692): p. 1079-1080.
5. Brantl, S. (2007) Regulatory mechanisms employed by cis-encoded antisense RNAs. Curr. Opin. Microbiol. 10, 102-109.
6. Isaacs, F. J. et al. (2004) Engineered riboregulators enable post-transcriptional control of gene expression. Nat. Biotechnol. 22, 841-847.
7. Pfeiffer, V. et al. (2009) Coding sequence targeting by MicC RNA reveals bacterial mRNA silencing downstream of translational initiation. Nat. Struct. Mol. Biol. 16, 840-846.
8. Opdyke, J. A. et al. (2004) GadY, a small-RNA regulator of acid response genes in *Escherichia coli*. J. Bacteriol. 186, 6698-6705.
9. Carriere, C., et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239.
10. Merten, O.-W. and M. Al-Rubeai, *Viral Vectors for Gene Therapy: Methods and Protocols*. Methods in Molecular Biology. Vol. 737. 2011.
11. Lofdahl, S., J. E. Sjostrom, and L. Philipson, CLONING OF RESTRICTION FRAGMENTS OF DNA FROM STAPHYLOCOCCAL BACTERIOPHAGE-PHI-11. Journal of Virology, 1981. 37(2): p. 795-801.
12. Charpentier, E., et al., *Novel Cassette-Based Shuttle Vector System for Gram-Positive Bacteria*. Appl. Environ. Microbiol., 2004. 70(10): p. 6076-6085.
13. Novick, R. P., I. Edelman, and S. Lofdahl, *Small staphylococcus-auerus plasmids are transduced as linear multimers that are formed and resolved by replicative processes*. Journal of Molecular Biology, 1986. 192(2): p. 209-220.
14. Westwater, C., et al., Development of a P1 phagemid system for the delivery of DNA into Gram-negative bacteria. Microbiology, 2002. 148(4): p. 943-950.
15. Norris, J. U., et al., Tissue-Specific and Pathogen-Specific Toxic Agents and Ribozymes. 1999.
16. Maiques, E., et al., Role of Staphylococcal Phage and SaPI Integrase in Intra- and Interspecies SaPI Transfer. J. Bacteriol., 2007. 189(15): p. 5608-5616.
17. Frees, D., et al., Clp ATPases are required for stress tolerance, intracellular replication and biofilm formation in *Staphylococcus aureus*. Molecular Microbiology, 2004. 54(5): p. 1445-1462.
18. Arnaud, M., A. Chastanet, and M. Debarbouille, New Vector for Efficient Allelic Replacement in Naturally Nontransformable, Low-GC-Content, Gram-Positive Bacteria. Appl. Environ. Microbiol., 2004. 70(11): p. 6887-6891.
19. Tormo, M. A., et al., *Staphylococcus aureus* Pathogenicity Island DNA Is Packaged in Particles Composed of Phage Proteins. J. Bacteriol., 2008. 190(7): p. 2434-2440.
20. Arthur, M., et al., The VanS sensor negatively controls VanR-mediated transcriptional activation of glycopeptide resistance genes of Tn1546 and related elements in the absence of induction. J. Bacteriol., 1997. 179(1): p. 97-106.
21. Karlsson, S., et al., Expression of *Clostridium difficile* Toxins A and B and Their Sigma Factor TcdD Is Controlled by Temperature. Infect. Immun., 2003. 71(4): p. 1784-1793.
22. Daniel Sobek, J. R., Enzyme detection system with caged substrates, 2007, Zymera, Inc.
23. Samie Jaffrey, J. P., Coupled recognition/detection system for in vivo and in vitro use, 2010, Cornell University.
24. Good, L., Translation repression by antisense sequences. Cellular and Molecular Life Sciences, 2003. 60(5): p. 854-861.
25. Sabine, B., Antisense-RNA regulation and RNA interference. Biochimica et Biophysica Acta (BBA)—Gene Structure and Expression, 2002. 1575(1-3): p. 15-25.

Informal Sequence Listing

```
>SEQ ID NO: 1 pacA and pacB (bold: promoter, underlined:
pacA, unformatted: pacB)
ATGTGACTTTCGTTACCCTCGCGTCAAAAAGAGTTTTTACGAAAGGAA

GCATAAGTGACCTGGGACGATCACAAGAAGAATTTTGCTCGCCTGGCGCGAGAT
```

-continued

GGTGGTTACACCATCGCACAGTATGCCGCCGAGTTTAATCTTAACCCTAATACCG

CACGTCGTTATCTCCGTGCCTTCAAAGAAGACACCAGGACTACGGACAGCCGCA

AGCCAAATAAGCCAGTCAGGAAGCCACTAAAAAGCATGATCATTGATCACTCTA

ATGATCAACATGCAGGTGATCACATTGCGGCTGAAATAGCGGAAAAACAAAGAG

TTAATGCCGTTGTCAGTGCCGCAGTCGAGAATGCGAAGCGCCAAAATAAGCGCA

TAAATGATCGTTCAGATGATCATGACGTGATCACCCGCGCCCACCGGACCTTACG

TGATCGCCTGGAACGCGACACCCTGGATGATGATGGTGAACGCTTTGAATTCGAA

GTTGGCGATTACCTGATAGATAACGTTGAAGCGCGGAAGGCCGCGCGCGCTATG

TTGCGTCGGTCCGGGGCCGATGTTCTGGAAACCACTCTTCTGGAAAAGTCTCTTT

CTCATCTCCTTATGCTGGAGAACGCCAGGGATACGTGTATTCGCCTGGTGCAGGA

AATGCGCGATCAGCAAAAAGACGATGATGAAGGTACTCCGCCTGAATACCGTAT

CGCGAGCATGCTAAACAGCTGTTCCGCGCAGATAAGCAGCCTGATCAACACCAT

TTACAGCATCCGGAATAACTATCGAAAAGAAAGCCGGGAGGCGGAAAAGCACG

CTTTATCTATGGGGCAAGCTGGCATTGTTAAGCTGGCATACGAACGAAAGCGTGA

AAATAACTGGTCAGTGCTGGAAGCGGCTGAATTCATCGAGGCGCATGGAGGAAA

AGTGCCGCCCCTGATGCTGGAGCAAATCAAAGCCGATCTGCGTGCTCCTAAGACC

AATACCGATGATGAGGAAAACCAAACAGCATCTGGCGCTCCATCACTTGAAGAT

CTGGATAAAATCGCGCGAGAACGGGCCGCCAGCCGCCGCGCTGATGCCGCATTG

TGGATTGAGCATCGTAGAGAAGAAATTGCCGATATCGTCGATACAGGTGGTTAT

GGTGATGTCGATGCGGAAGGCATATCAAACGAAGCATGGCTTGAACAGGATCTG

GACGAAGACGAGGAGGAAGACGAAGAAGTTACCCGCAAACTGTACGGGGATGA

TGATTAAATGGCCAGAAGTTGCGTAACGGACCCACGTTGGCGCGAGCTTGTGGC

GCTATATCGTTATGACTGGATTGCGGCCGCTGATGTGTTGTTTGGGAAGACACCA

ACCTGGCAGCAGGATGAGATCATTGAGTCCACGCAGCAGGACGGCAGTTGGACA

AGTGTGACCTCCGGCCATGGTACTGGTAAATCGGATATGACGAGTATCATTGCAA

TACTCTTCATCATGTTTTTCCCCGGCGCTCGCGTCATTCTGGTCGCTAACAAAAGA

CAGCAAGTCCTTGATGGTATTTTCAAATACATAAAGAGCAATTGGGCTACTGCTG

TTAGCAGATTCCCGTGGTTGTCGAAGTATTTCATTCTTACAGAAACGTCTTTTTTT

GAGGTGACTGGCAAGGGTGTTTGGACAATATTGATAAAGTCCTGTCGTCCCGGA

AATGAGGAGGCGTTGGCTGGTGAACACGCCGATCATCTCTTGTATATCATCGACG

AAGCGTCGGGTGTGAGTGATAAAGCATTCAGTGTGATAACAGGTGCGCTGACCG

GTAAGGATAACCGTATTCTGCTTCTTTCCCAGCCTACGCGACCTTCAGGCTATTTC

TACGATTCACACCACAGACTAGCTATTCGCCCGGGAAATCCTGATGGATTGTTTA

CTGCGATAATACTGAATAGTGAAGAATCTCCGCTTGTAGATGCAAAATTTATACG

AGCAAAACTTGCGGAGTATGGCGGTCGTGATAACCCCATGTACATGATCAAAGT

ACGTGGTGAATTTCCCAAATCTCAAGATGGCTTTCTTCTTGGTCGTGATGAGGTT

GAGCGGGCGACGCGGCGAAAGGTCAAGATTGCCAAAGGATGGGGCTGGGTTGC

ATGTGTTGACGTTGCTGGTGGCACAGGACGAGATAAGTCCGTTATTAATATCATG

ATGGTGTCCGGCCAGCGAAATAAACGCCGTGTAATCAACTATCGTATGCTGGAAT

ACACAGACGTTACAGAAACGCAGTTAGCCGCCAAGATTTTCGCAGAATGTAACC

-continued
CAGAACGGTTCCCGAACATAACCATAGCTATTGATGGCGATGGCTTGGGGAAAT

CGACGGCTGATCTAATGTACGAACGCTATGGCATTACCGTCCAGCGTATCCGCTG

GGGTAAAAAGATGCACAGCCGTGAAGATAAAAGCCTTTATTTCGATATGCGCGC

TTTCGCGAATATTCAGGCGGCAGAAGCTGTAAAATCAGGGCGTATGAGGCTTGA

TAAGGGGCTGCGACTATAGAGGAAGCATCAAAGATACCGGTAGGGATAAATTC

CGCAGGTCAATGGAAGGTGATGTCAAAGGAAGATATGAAGAAAAAACTCAACCT

GCACTCACCGGACCATTGGGATACATATTGTTTCGCTATGTTGGCGAACTATGTT

CCCCAAGATGAAGTGCTTAGCGTCGAAGACGAAGCGCAGGTTGATGAAGCTCTG

GCATGGCTTAATGAATAA

> SEQ ID NO: 2 P1 lytic replicon containing the C1 repressor-
controlled P53 promoter, the promoter P53 antisense, the repL genes,
and an in-frame deletion of the kilA gene
CACTATAGGGCGAATTGGCGGAAGGCCGTCAAGGCCGCATTTGGGCCCGG

CGCGCCGGATCCGCTAGCTCTAGACTGGCAGGTTTCTGAGCAGATCGTCCAACCC

GATCTGGATCGGGTCAGAAAAATTTGCTCTAATAAATTTCGTTTTCTAAGTGCAA

AGAATCACCATTTCGAGCTGGTGATTGAAGGTTGATGCAAATTTGGAGAAAAAA

TGCAACAAACATTCAATGCGGATATGAATATATCAAACCTTCATCAAAATGTCGA

TCCTTCAACCACTCTGCCCGTTATTTGTGGTGTTGAAATTACGACCGACCGCGCTG

GCCGTTACAACCTTAATGCTCTACACAGAGCGAGCGGACTCGGTGCCCATAAAG

CGCCAGCTCAATGGCTAAGAACGCTGTCAGCTAAACAGCTCATCGAAGAGCTTG

AAAAAGAAACTATGCAGAATTGCATAGTTTCGTTCACAAGCAATGGAAGCAGGA

TTTCTTTCACGACTCGTATAACCGGCAAAGGTCAGCAGTGGCTGATGAAGCGATT

GCTTGATGCTGGTGTGCTGGTACCTGTCGCGGCAACGCGCTAACAGACGTAGTAA

GAACCACCAGCATTGTAATGCTGGCTAAAGTCACTTTCCTGAGCTGTATAACGAT

GAGCGATTTTACTTTTTCTGGCTATGAATTGGCCTGCTTTGTAACACACTCCGGTC

TATCCCGTAGCGCCGGGCATATCCTGTCGCAATGTGCAAATCTCGCGGCAACAAC

CAGTGAATACTTCATTCACAAGCCTCACCGCCTGATCGCGGCAGAAACTGGTTAT

AGCCAATCAACCGTCGTTCGTGCATTCCGTGAAGCTGTAAACAAAGGAATTCTGT

CTGTAGAGATTGTTATCGGCGATCACCGTGAACGTCGCGCTAACCTGTACCGGTT

TACACCATCCTTTTTGGCCTTCGCACAACAAGCCAAAAATGCGCTGATAGAAAGC

AAATTAAAGATCTCTTCAGCGGCAACCAAGGTTAAAGCTGTTCTCGCTAAGACAT

TGGCTTTATTTAATTTTTTATCCACACCCCCATGTCAAAATGATACCCCCTCCCCC

TGTCAGGATGACGTGGCAATAAAGAATAAGAAGTCACAAGTTAAAAAAACAAA

AAGATCAGTTTCCGGCGGTGCCGGAACAACCAGCCTCAAAAAATTGACTTCATG

GATCGCTAAGGCAAAAGCAAAGGCTGACAATCTGCGGTTATCCAAAAAACGCAC

TCAAAAACATGAGTTCAAGCAGAAAGTAGAGGCGGCTGCGCGGAAATATGCTTA

CCTGAAGAACAAGCGTTCGCCTGATATTGGCGGGATATCAAACTTCGATAACCTA

CCGCATTGCATGACGGTAAACGAAGCTCTTAATGCGGTTTTAGCCAAAAATAAA

GATAACGAACAATGGGTATACCGGCAGGATTCAGAGGGTAATGAATTGCTCTA

ATTATAACCATGCATACTTTCAACACCTCTAGTTTGCCATGAGGCAAACTCATAG

GTGTCCTGGTAAGAGGACACTGTTGCCAAAACTGGACGCCCCATTATTGCAATTA

ATAAACAACTAACGGACAATTCTACCTAACAATAAGTGGCTTAAAAAAACCCGC

-continued
CCCGGCGGGTTTTTTTATCTAGAGCTAGCGGATCCGGCGCGCCGGGCCCTTCTGG

GCCTCATGGGCCTTCCGCTCACTGCCCGCTTTCCAG

> SEQ ID NO: 3 pBHR1 rep (bold: ORF)
TTGACTGCCACTTTTACGCAACGCATAATTGTTGTCGCGCTGCCGAAAAGT

TGCAGCTGATTGCGCATGGTGCCGCAACCGTGCGGCACCCCTACCGCATGGAGA

TAAGCATGGCCACGCAGTCCAGAGAAATCGGCATTCAAGCCAAGAACAAGC

CCGGTCACTGGGTGCAAACGGAACGCAAAGCGCATGAGGCGTGGGCCGGG

CTTATTGCGAGGAAACCCACGGCGGCAATGCTGCTGCATCACCTCGTGGCG

CAGATGGGCCACCAGAACGCCGTGGTGGTCAGCCAGAAGACACTTTCCAAG

CTCATCGGACGTTCTTTGCGGACGGTCCAATACGCAGTCAAGGACTTGGTG

GCCGAGCGCTGGATCTCCGTCGTGAAGCTCAACGGCCCCGGCACCGTGTCG

GCCTACGTGGTCAATGACCGCGTGGCGTGGGCCAGCCCCGCGACCAGTTG

CGCCTGTCGGTGTTCAGTGCCGCCGTGGTGGTTGATCACGACGACCAGGAC

GAATCGCTGTTGGGGCATGGCGACCTGCGCCGCATCCCGACCCTGTATCCG

GGCGAGCAGCAACTACCGACCGGCCCCGGCGAGGAGCCGCCCAGCCAGCC

CGGCATTCCGGGCATGGAACCAGACCTGCCAGCCTTGACCGAAACGGAGGA

ATGGGAACGGCGCGGGCAGCAGCGCCTGCCGATGCCCGATGAGCCGTGTTT

TCTGGACGATGGCGAGCCGTTGGAGCCGCCGACACGGGTCACGCTGCCGCG

CCGGTAG

> SEQ ID NO: 4 phi80alpha terS and terL genes (bold: terS
ORF, underline: terL ORF)
TTTTAAAAAGCGTATAGCGCGAGAGTTGGTGGTAAATGAAATGAACGAA

AAACAAAAGAGATTCGCAGATGAATATATAATGAATGGATGTAATGGTAAAA

AAGCAGCAATTTCAGCAGGTTATAGTAAGAAAACAGCAGAGTCTTTAGCAAG

TCGATTGTTAAGAAATGTTAATGTTTCGGAATATATTAAAGAACGATTAGAA

CAGATACAAGAAGAGCGTTTAATGAGCATTACAGAAGCTTTAGCGTTATCTG

CTTCTATTGCTAGAGGAGAACCTCAAGAGGCTTACAGTAAGAAATATGACCA

TTTAAACGATGAAGTGGAAAAAGAGGTTACTTACACAATCACACCAACTTTT

GAAGAGCGTCAGAGATCTATTGACCACATACTAAAAGTTCATGGTGCGTATA

TCGACAAAAAAGAAATTACTCAGAAGAATATTGAGATTAATATTGGTGAGTA

CGATGACGAAAGTTAA<u>ATTAAACTTTAACAAACCATCTAATGTTTTCAACAGAA</u>

<u>ACATATTCGAAATACTAACCAATTACGATAACTTCACTGAAGTACATTACGGTGG</u>

<u>AGGTTCGAGTGGTAAGTCTCACGGCGTTATACAAAAAGTTGTACTTAAAGCATTG</u>

<u>CAAGACTGGAAATATCCTAGGCGTATACTATGGCTTAGAAAAGTCCAATCAACA</u>

<u>ATTAAAGATAGTTTATTCGAAGATGTCAAAGATTGTTTGATAAACTTCGGTATTT</u>

<u>GGGACATGTGCCTTTGGAATAAGACTGATAACAAAGTTGAATTGCCAAACGGCG</u>

<u>CAGTTTTTTGTTTAAAGGATTAGATAACCCAGAGAAAATAAAGTCGATAAAAG</u>

<u>GCATATCAGACATAGTCATGGAAGAAGCGTCTGAATTCACACTAAATGATTACA</u>

<u>CGCAATTAACGTTGCGTTTGAGGGAGCGTAAACACGTGAATAAGCAAATATTTTT</u>

<u>GATGTTTAACCCAGTATCTAAACTGAATTGGGTTTATAAGTATTTCTTTGAACATG</u>

<u>GTGAACCAATGGAAAATGTCATGATTAGACAATCTAGTTATCGAGATAATAAGTT</u>

<u>TCTTGATGAAATGACACGACAAAACTTAGAGTTGTTAGCAAATCGTAATCCAGCA</u>

-continued
TATTACAAAATTTATGCGTTAGGTGAATTTTCTACACTAGACAAATTGGTTTTCCC

TAAGTATGAAAAACGTTTAATAAATAAAGATGAGTTAAGACATTTACCTTCTTAT

TTTGGATTGGACTTTGGCTACGTTAATGATCCTAGTGCTTTTATACATTCTAAAAT

AGATGTAAAGAAAAAGAAGTTATACATCATTGAAGAGTATGTTAAACAAGGTAT

GCTGAATGATGAAATAGCTAATGTCATAAAGCAACTTGGTTATGCTAAAGAAGA

AATTACAGCAGATAGTGCAGAACAAAAAAGTATAGCTGAATTAAGGAATCTAGG

GCTTAAAAGGATTTTACCAACCAAAAAAGGGAAGGGCTCGGTTGTACAAGGGTT

ACAATTCTTAATGCAATTTGAAATCATTGTTGATGAACGTTGTTTCAAGACTATTG

AAGAGTTTGACAACTACACATGGCAAAAGGACAAAGATACAGGTGAATATACCA

ATGAACCAGTAGATACATACAATCATTGTATCGATTCGTTGCGTTATTCAGTGGA

ACGATTCTACAGACCGGTTAGAAAACGCACAAATGTCAGTTCGAAAGTTGACAC

AATAAAATCTCTAGGATTATAGGAGGGAACAAATGTTAAAAGTAAACGAATTTG

AAACAGAT

>SEQ ID NO: 5 pT181
TTTGCGGAAAGAGTTAGTAAGTTAACAGAAGACGAGCCAAACCTAAATGG

TTTAGCAGGAAACTTAGATAAAAAAATGAATCCAGAATTATATTCAGAACAGGA

ACAGCAACAAGAGCAACAAAAGAATCAAAAACGAGATAGAGGTATGCACTTAT

AGAACATGCATTTATGCCGAGAAAACTTATTGGTTGGAATGGGCTATGTGTTAGC

TAACTTGTTAGCGAGTTGGTTGGACTTGAATTGGGATTAATCCCAAGAAAGTACC

GGCTCAACAACCCATAAAGCCCTGTAGGTTCCGNCCAATAAGGAAATTGGAATA

AAGCAATAAAAGGAGTTGAAGAAATGAAATTCAGAGAAGCCTTTGAGAATTTTA

TAACAAGTAAGTATGTACTTGGTGTTTTAGTAGTCTTAACTGTTTACCAGATAAT

ACAAATGCTTAAATAAAAAAAGACTTGATCTGATTAGACCAAATCTTTTGATAGT

GTTATATTAATAACAAAATAAAAAGGAGTCGCTCACGCCCTACCAAAGTTTGTGA

ACGACATCATTCAAAGAAAAAAACACTGAGTTGTTTTTATAATCTTGTATATTTA

GATATTAAACGATATTTAAATATACATCAAGATATATATTTGGGTGAGCGATTAC

TTAAACGAAATTGAGATTAAGGAGTCGATTTTTTATGTATAAAAACAATCATGCA

AATCATTCAAATCATTTGGAAAATCACGATTTAGACAATTTTTCTAAAACCGGCT

ACTCTAATAGCCGGTTGGACGCACATACTGTGTGCATATCTGATCCAAAATTAAG

TTTTGATGCAATGACGATCGTTGGAAATCTCAACCGAGACAACGCTCAGGCCCTT

TCTAAATTTATGAGTGTAGAGCCCCAAATAAGACTTTGGGATATTCTTCAAACAA

AGTTTAAAGCTAAAGCACTTCAAGAAAAAGTTTATATTGAATATGACAAAGTGA

AAGCAGATAGTTGGGATAGACGTAATATGCGTATTGAATTTAATCCAAACAAAC

TTACACGAGATGAAATGATTTGGTTAAAACAAAATATAATAAGCTACATGGAAG

ATGACGGTTTTACAAGATTAGATTTAGCCTTTGATTTTGAAGATGATTTGAGTGA

CTACTATGCAATGTCTGATAAAGCAGTTAAGAAAACTATTTTTTATGGTCGTAAT

GGTAAGCCAGAAACAAAATATTTTGGCGTGAGAGATAGTAATAGATTTATTAGA

ATTTATAATAAAAAGCAAGAACGTAAAGATAATGCAGATGCTGAAGTTATGTCT

GAACATTTATGGCGTGTAGAAATCGAACTTAAAAGAGATATGGTGGATTACTGG

AATGATTGCTTTAGTGATTTACATATCTTGCAACCAGATTGGAAAACTATCCAAC

GCACTGCGGATAGAGCAATAGTTTTTATGTTATTGAGTGATGAAGAAGAATGGG

-continued

```
GAAAGCTTCACAGAAATTCTAGAACAAAATATAAGAATTTGATAAAAGAAATTT
CGCCAGTCGATTTAACGGACTTAATGAAATCGACTTTAAAAGCGAACGAAAAAC
AATTGCAAAAACAAATCGATTTTTGGCAACATGAATTTAAATTTTGGAAATAGTG
TACATATTAATATTACTGAACAAAAATGATATATTTAAACTATTCTAATTTAGGA
GGATTTTTTATGAAGTGTCTATTTAAAAATTTGGGGAATTTATATGAGGTGAAA
GAATAATTTACCCCTATAAACTTTAGCCACCTCAAGTAAAGAGGTAAAATTGTTT
AGTTTATATAAAAAATTTAAAGGTTTGTTTTATAGCGTTTTATTTTGGCTTTGTAT
TCTTTCATTTTTTAGTGTATTAAATGAAATGGTTTTAAATGTTTCTTTACCTGATAT
TGCAAATCATTTTAATACTACTCCTGGAATTACAAACTGGGTAAACACTGCATAT
ATGTTAACTTTTTCGATAGGAACAGCAGTATATGGAAAATTATCTGATTATATAA
ATATAAAAAATTGTTAATTATTGGTATTAGTTTGAGCTGTCTTGGTTCATTGATT
GCTTTTATTGGGCCCACCTAGGCAAATATGCTCTTACGTGCTATTATTTAAGTGAC
TATTTAAAAGGAGTTAATAAATATGCGGCAAGGTATTCTTAAATAAACTGTCAAT
TTGATAGCGGGAACAAATAATTAGATGTCCTTTTTTAGGAGGGCTTAGTTTTTTGT
ACCCAGTTTAAGAATACCTTTATCATGTGATTCTAAAGTATCCAGAGAATATCTG
TATGCTTTGTATACCTATGGTTATGCATAAAAATCCCAGTGATAAAAGTATTTAT
CACTGGGATTTTTATGCCCTTTTGGGTTTTTGAATGGAGGAAAATCACATGAAAA
TTATTAATATTGGAGTTTTAGCTCATGTTGATGCAGGAAAAACTACCTTAACAGA
AAGCTTATTATATAACAGTGGAGCGATTACAGAATTAGGAAGCGTGGACAAAGG
TACAACGAGGACGGATAATACGCTTTTAGAACGTCAGAGAGGAATTACAATTCA
GACAGGAATAACCTCTTTTCAGTGGGAAAATACGAAGGTGAACATCATAGACAC
GCCAGGACATATGGATTTCTTAGCAGAAGTATATCGTTCATTATCAGTTTTAGAT
GGGGCAATTCTACTGATTTCTGCAAAAGATGGCGTACAAGCACAAACTCGTATAT
TATTTCATGCACTTAGGAAAATGGGGATTCCCACAATCTTTTTTATCAATAAGATT
GACCAAAATGGAATTGATTTATCAACGGTTTATCAGGATATTAAAGAGAAACTTT
CTGCCGAAATTGTAATCAAACAGAAGGTAGAACTGTATCCTAATATGTGTGTGAC
GAACTTTACCGAATCTGAACAATGGGATACGGTAATAGAGGGAAACGATAACCT
TTTAGAGAAATATATGTCCGGTAAATCATTAGAAGCATTGGAACTCGAACAAGA
GGAAAGCATAAGATTTCAGAATTGTTCTCTGTTCCCTCTTTATCATGGAAGTGCA
AAAAGTAATATAGGGATTGATAACCTTATAGAAGTTATTACTAATAAATTTTATT
CATCAACACATCGAGGTCCGTCTGAACTTTGCGGAAATGTTTTCAAAATTGAATA
TACAAAAAAAGACAACGTCTTGCATATATACGCCTTTATAGTGGAGTACTACAT
TTACGAGATTCGGTTAGAGTATCAGAAAAAGAAAAAATAAAAGTTACAGAAATG
TATACTTCAATAAATGGTGAATTATGTAAGATTGATAGAGCTTATTCTGGAGAAA
TTGTTATTTTGCAAAATGAGTTTTTGAAGTTAAATAGTGTTCTTGGAGATACAAA
ACTATTGCCACAGAGAAAAAGATTGAAAATCCGCACCCTCTACTACAAACAAC
TGTTGAACCGAGTAAACCTGAACAGAGAGAAATGTTGCTTGATGCCCTTTTGGAA
ATCTCAGATAGTGATCCGCTTCTACGATATTACGTGGATTCTACGACACATGAAA
TTATACTTTCTTTCTTAGGGAAAGTACAAATGGAAGTGATTAGTGCACTGTTGCA
AGAAAAGTATCATGTGGAGATAGAACTAAAAGAGCCTACAGTCATTTATATGGA
GAGACCGTTAAAAAATGCAGAATATACCATTCACATCGAAGTGCCGCCAAATCC
```

-continued

```
TTTCTGGGCTTCCATTGGTTTATCTGTATCACCGCTTCCGTTGGGAAGTGGAATGC
AGTATGAGAGCTCGGTTTCTCTTGGATACTTAAATCAATCATTTCAAAATGCAGT
TATGGAAGGGGTACGCTATGGTTGCGAACAAGGATTATATGGTTGGAATGTGAC
GGATTGTAAAATCTGTTTTAAGTACGGTTTATACTATAGCCCTGTTAGTACTCCAG
CAGATTTTCGGATGCTTACTCCTATTGTACTGGAGCAAGCCTTTAGAAAAGCTGG
AACAGAATTGTTAGAGCCATATCTTAGTTTTAAAGTTTATGCACCACAGGAATAT
CTTTCNCGGGCATATAACGATGCTCCCAAATATTGTGCAAATATCGTAAATACTC
AACTGAAAATAATGAGGTCATTATTATTGGAGAAATTCCTGCTCGATGTATTCA
AGATTATCGCAATGATTTAACTTTTTTTACAAATGGGCTTAGTGTTTGTTTAGCAG
AGCTAAAAGGATATCAGGTTACCACTGGCGAACCTGTTTGCCAGACCCGTCGTCT
AAATAGTCGGATAGATAAAGTAAGATATATGTTCAATAAAATAACTTAGTGCGTT
TTATGTTGTTATATAAATATGGTTTCTTATTAAATAAGATGAAATATTCTTTAATA
TAGATTTGAATTAAAGTGGAAAGGAGGAGATTGTTATTATAAACTACAAGTGGA
TATTGTGTCCTATTTGTGGAAATAAAACAAGACTACGAATACGAGTGGATACTAT
ACTTAAAAATTTCCCTTTATACAGCCCCAAATGTAAGAACGAAACTTTAATTAAT
GTTCAAAAAATGAATATAATAACAATCAAAGAGCCAGACGCCAAGACGCAGAGC
CGATAATTTGAGAAATGAAACTCTCATCTTATCGGCTCTTTTTGTTTATCTGAATT
TTACTGACTAGCCTTCAATATTTCC

> SEQ ID NO: 6 Ef11 terA and terB (bold: terA ORF, underline: terB ORF)
CTCAATTCAACAAGTATTGTGAGGTGGTGTTATATGTCAGATGGATAAAA
AGGAACAAGCAAAGAAATATTATGAAAAAGGTTGGAAATACAAGGATATTTC
CGAAAAGCTTTCTGTACCTCTCAACACATTGAAGTCATGGAGAAAACGTGAT
AAATGGGAAAGAGGGGGTGCAACCAAAGAGGTGCAACCTACAAATAGGGGT
GCACCTAAAGGTAATCAAAATGCTATAGGCAATAAAGGTAATAGTCGAGCCT
CGCCACCAAAAAGAAATAAGAATGCTGTTAAAACTGGCGAATACGAAACAAT
ATTTGCCGATATGTTATCTGACGAAGAAAAGGACATCTATTCTACTATGAAT
GATGATCCTTTTTTTATTTTGGATGAAGAAATAAGAATCCTGAAAATTCGCC
AATATAGAATGCTTAAACGCATAAAAGATGCAGAGGCTGGCTTAAATGATGA
AGAAGTTGAACGTTTGCAGCAGCTTCGCAAAGTTAAAGAGCCATCGGTAATT
GATGGGAAAATGGTTACTGTTAAGAGAGAAGTTTTAAAAGATGTACAAGTCA
CTCGTAAAACATTTAGAAAGTTAGATGACATCCTGGCTATTGAAGATGCGTT
GACTCGCGTTAGCAATCAATTAATAAAGGCGATTAAGCAACAAAAAGAATTA
TTGTCGACAGATAAAAAATCTCTTTTAATGGAGGCTCAAATTGAGAAGATAA
AGCTTGAGACAGACAAATTAAGTGGCGGATCATCTAACGATGAAGCTGACT
CTTGGAAACAAGCAGTTATAAATGCAGCAAATAAGCGGGCGGTGGAAGAAA
ATGAATAAGAGTTTATTCCGTTTGCCGATATTGGTGCAGCAATTGATTACTACTA
CGATAAACCAGTTGCTTTTTGTCAGGATATTTTGCATCTTGATCCAGATGAATGG
CAGGATAAGGTCTTGGATGATTTGGCTAAATTCCCAAAAGTCTCAGTTAGATCAG
GGCAGGGTGTTGGAAAAACGGCGTTGGAGGCTGGTGCTATTCTTTGGTTTCTAAC
ATGCCGGCCATATGCAAAAGTAATAGCAACTGCTCCGACGATGAAACAATTATA
CGATGTTCTATGGGCAGAAGTGGCTAAGTGGCTGAATAACAGCTTGATTAAAGA
```

-continued

CTTACTTAAATGGACCAAGACGAAAATTTATATGGTTGGCGATTCAGAACGATGG

TTTGCTACAGCTCGAACAGCAACTAAACCAGAAAATATGCAAGGATTTCACGAA

GACCATATGTTAATAGTGGTTGATGAAGCATCAGGTGTTGCTGATCCCATTATGG

AAGCAATATTAGGTACTCTTTCAGGATTTGACAATAAATTACTAATGTGTGGGAA

CCCCAACAATATTGAAGGGGTTTTTTATGATTCGCATAATACAGATAGAGACAAG

TATAGAACGCACAAAGTTTCTAGTTACGATAGCAAACGTACTAACAAAGAAAAT

ATTCAAATGCTCATCGATAAGTATGGTGAGAATAGCGATGTAGCTCGTGTTCGTA

TTTATGGTGAATTTCCCAAAGGCGCACTTGATTCATTTATCAGCCTTGAAATTGTT

GAGTTTGCCAAAGATATTAATATTTCTGATTCAGAATTAAAACATGTTAGAGAAG

GACACATAGGTGTCGATGTGGCTCGTTTTGGTGATGATTCAACGATAGTATTTCC

TAGAATCGGAGCTAAAGCATTGCCATTTGAAAAATATAGTAAGCAAGATACCAT

GCAGACCACTGGTCGAGTTTTAAAAGCGGCGAAAAGGATGATGGATGACTATCC

TACAATAAAAAAAGTGTTCATCAAAGTAGATGATACAGGTGTTGGTGGAGGTGT

TACTGATAGACTTAAAGAAGTAATTAGCGATGAAAAACTTCCCTATGAAGTAATT

CCGGTAAATAATGGAGAATCTTCTACAGACGATTATTATGCAAATAAAGGAACA

CAAATATGGGGAGATGTTAAAGAACTGTTAGAACAAAACATTTCCAATTCGATT

AATGGTCAAGGGCCGACGATAGAACTTCCTGATAATGCAAATCTAATCAAAGAA

TTGAGCACACGTAAATTTAAAATGACTAGCAATGGAAAAATCCGTTTAGAAAGT

AAAGAAGATATGAAAAAGCGTAATGTTGGCAGTCCAGATATTGCTGATGCGTTA

ACGTTAGCGTTTTACGAGCCATTTAGACCAGAACCTATAAACGTTAAAAAAGCTA

TTAATACGTTCAAAAAATTAGGATTAAGTAGGTGATAGAGTGAATAATAAATTAT

TGAACGGTTCTAGATTTGAT

> SEQ ID NO: 7 repB
GATCTTTTGCCCATTTTATTTTTATAAAATGGGCAGGTGGCGTTTGTGTAA

AGCAAATCGACACAATCCAAAGGGGATAAAAGGGGAAAGTGAAACTTCCCCCTT

TTCAAGCCACATTGTAATACAAGAACGAAGTGTTTTGTATTACAATGTGATAGCT

TGCAGTATTTATGGTTTTATATGGTCTATTTTGTTGTGAGGATTGTAACCGAATAG

GGCGCAATGCTTATTACAAAATCAATGACAAAGGGCGATTGAGGAATGAGCGCT

GAGGCATTTTATCTTTGAGTAAGTTATTGATGGATCAGAAAAATGTATCACAAAT

TGAAACAAAGACTCACTCATTTAAGAGAAGCTACTATCATGAAATTTTGTTGTTG

TGATAAGCAACTTCTAATACACGATTTTTAGCCATTACATCACTCGTTTTTAGAGT

GATGTGTAAGTGCGCATTGCACTCTTTTTTTACGAAACAAGCCGACCAGCGTTTG

AAACTTTTTAGTTTTTCATCATTCTATTTTAAAACGTTCTAAAACTCGATTTAAGC

GACTTTAATTCGAAACTGTCTATTTGTTCAAAGGGAGCATTAAGAATGCTTAAAC

GAGCTTTTAAGGGGGTTTAAATTGATTTTGAATTGAATAGCTTGTTGTAAGTTGT

AAAAAAAACAAGTTAAACAAAGTATCAGTTTTCCATTTAAGGGTTGTTAGGGCTT

GCCCTGACCGTCTGTAAGACGCTTGATTGCATGATATGAGTATTTAGCTAGTCAA

ACAGTTAAAACAGCTTATATGAGCAATTAGAGGGAATCCAATAAATTCCTAAAA

GCGGTTTTGATCTTTTCTTTTAGCGAGTGAACGCTGCAAGTAAAATGTGAGCGTT

CACTCGCTCACTCCTTTTTTTGATGACTTTGACCTTTGGTTTTAAATTTTTGAAAA

AAATAAAAAATAGGCGAAGCCTATTATATATTTATCTTATATATTTTAATCTTTTA

```
TTCTTTTGCGTCAAAAAAAAATCAATATTTTCAAGGCTTTATAGAATTATATACC

AACAAAAAACTGTGTATATACCAACAAAAAACTGTGCATACACCAACAAAAAAC

TGTGCATATACCAACTTCTTTGTTTGTTTCGTTGGTATATAATGATATAATAAAAG

CATGAAGAATCTCTCTACGAAAAGTGTTTCTTCATGCTTATCTAAACTCACTCAC

AAAGGAGCAGTTTTCTatgtctagtatatcaaaaaatgaacctaatcaaaagcaggtgcaaaccttgaacgaattgtcaa aacgaaaagtagtggaacataattctttaattaccagtattgcgaaaatggataaaacgccactgaaaatgtttgaattagccgtgtcttgt attaataccgaagaaccacccaaagatcatacggtttatctctcaaaagaagaattgtttgccttttttaaggtatctgataatgacaaacat agtcgttttaaacaagcagtagagaatatgcaaaaacaagcattttcaaattaaagaagaagtaggtaaaggatttaaatttaggagtat tgttcccattccatatgtcgagtggacagattatcatgatgacgtaaaaattgaatttcatcgtgaaatcatgccctacttaattaatctaaaa caaaatttcacgcaacatgctttgtctgatattgcagagctgaatagcaaatactctattatcttgtaccgttggttatccatgaattataacc aatacgagcattatagttataagggcggacggagagaagaacaagtggaagcctaccgcaatcctaccatttcaatgcgagaattacg agaaatgacggatacagttgatgaataccccgctttgatagattagaacatagagttttaaaagaaccaatagaagaaattaacgaaaa cacctcttttaacgtgacgtatgacaagataaaaaaaggacgaagcattgattctattgtctttcatatcacgaaaaaacgtcgagcagat gataacagctacaagttagaagataaagattatcaatccgacaaagaggaaaaatcaagaaatgaagctgacttattaaaacaggcaat ggaaagcaagtacacacgattattgattgaaaactttctcttatcccctcttgaaatgacggacacggcacttatggcaggtttgcaaaag aacgtctatccgttgtatgacgagttaaaggaattaagaggattgaatgggggtcaaagaccacttgtcttatatatctagcaaaaaagaag cctattctaaacgcaatgtagcgaagtatctgaaaaaagcaatcgagcaatatctacctacggttaaaaggcaggacttaaaccatgagt gaGAACTT > SEQ ID NO: 8 pDL278
TGGCGATTCTGAGACCTCTGAGAGGCTCTCAGAGCTATCTAAAGCTGAGG

GATATATAAATACCTTAGAAAATTATTCGAAGAGCTTAGAAGCGAAAATAGAGC

GTTTAGAGCGCGAGGGGCTGAAATTAGAAAAACTAAAAACACAAATAGCTGACC

TAAAAATCATGTCTGAGAAAGAACTAGCGGCTATTACCCCTAAAAAAGGCGTGT

TCGGTAAAGAATATGTGGAATTGACTAAAGAGCAGTTTGAAGAATTTAAAGGGC

TGATATACCGAAGCAGAAACCTTGTTCATCAAAAAGAGCTAGAGAATGAGCAAT

TAAGGCGGATAGTGCCTCTGAGACGCTCTAAACGGTTTGAAGCGAGTTGGAACG

AGCTAAAGAAAAAGTAAGGGAGAGAGCATAGAGCGTCTTAGGAACGAAAATA

GAGCGCTTAGAAGTGAAAACTCAGTTTTGAGACAGCAAAATGACAAAATGCTAG

GAAAACTGAAAGAGTTTATGCCAGATAAAGCCTTAAAAAATTTTATATCAGAGTT

AAGAGCTATTCAGCCAATCGTAAGGGTAGTTAAACGAGTGATTGAAAAAGGGCT

AGGCCTTTGAGCGATTTATGCCGTGAAAGCTAATTGACAATAAGCAAGGGCAAA

GTACGCTAGGACGTGACGAGCCGAAAGGCTTTAGCGTTTCGAGCCGACACGGAC

AAAGGACGTCCGCCCTTGGTTACTTGTTGTCAATTAGACCATGGAATAAAGTAAG

CGGACATGGTATAATAGCTAGGTCGCAACGTTCTTTCGCTAAGTTACGAACTTAG

ATTGGAGGTGAGCGCTGTGAAGACTTTCCTAGAACTTGTTTTGATACCTTTTGTG

GTTGGCGTTGCTGCAGAGGTAAGTGCTGATTGGTTGATTCGGTATGTTCGAAACA

AACGCGACAAAAATTAACCTGAGTTCTTTTTGAGGACAAAAAAGAAAGACAGTA

GTTCCAGCTACTGTTTTTTTGCGTTGTGCTATTCGTTTCCTAGAACTTCTAGCGTT

AAAATTATTATACCACGTTTGGATTTAGAAAGTCAAAATTTGAGGTTTTAGGGGT

GAATTTTTCGTGAAACGAAAAAGAGGGCTGAAAAGCCCTTAAAAACCCAATTGC

GTAGCAAGGGTTTTTTCTTATCTTGATACATATAGAAATAATGAGTTTTTTTATTT
```

-continued

TCTTGTTTTAAAGCACCTCAAACCCTTGATATTGCTGGGTTTTTAGGTAACAAAA

AAGCCCTTGCAATTTAATAAAATAAAGTTTATAATTTAAGTGTCCAATTTAAAAT

AATAAACTTAGGAGAATTGCAGGAACTTTTTTATATACTCAAAAAAATTTTTTTG

CAAGAAAATTATAACATGACAGGTACTGAAAATCAAGTCTTTAAGGACTATTCTA

AGAATGGCAAAGATAGAAAGTGGCGAGAACGCAAGTTAAAAAATATTGAGCTTG

CTGGTCGTTTAGAGCGTTTAGGATATCGTTCGTTTGAACGGGTCTATCAATGTGC

CGAAGTGTTGAAGTTTATCGAACAACAAGACGGCACGAAAAAACTCTATCAGTC

TTATTTTTGCAAAAATAAGCTCTGCCCAATTTGTAACTGGAGACGGTCAatgaagtatg cttatcaagctgaattagtggtaaatgaagcaatgaaacgctatccaaaaggtcgctttctcttttttgaccttgacgattaagaacattagtg gtgaaaaattaaataaatcaatttcagaaatagggcgagcttttaatcgtcttatgaaatacaagaaagtcgataaaaatgttattggctatt tgcgagccactgaggtaacttattcaactgagcatgagaattatcaccctcatttgcatgtattgttatttgtgaaatctagctattttactgga aataatacaaattacattagccaagaagaatggacgaaactatgggctaaggcgatgaaattggattatacacctgtagttgatattcga accgtcaaagctcataaacgtaaaaacttgaagtcagctattatcgaaacagctaaatatcctgttaagccttttgatgtagatacagaag atgtgacattattctctgaaatggtcaaagaacggataacagaagatttaacgaatggtagcaccgaaaaaggcagattggttttggaa agttgttcaagaaaatcaaggcggagttagctcttgatgatgtcgaagaagggaatcttgttcagaccggagcagaagaatctgcaga aagtactggtcgtgaaattgttgccttttggaattgggatagaaagaattattttgtgaggtagCTGATGAGTAAAACAGT

ATCAGAATTAGCTCAAGAATTGGGAGTTAGTAGGCAGTATCTTAATCGGATTTTA

TCGCAAAATAATCTCGGTCGAAAAAAAGGGAATAAAAAAGTAGTTTCCGATATG

GACGAGAAAGTTATGCAAGGGTTTATTGTTTTCTAAAATCTGATTACCAATTAGA

ATGAATATTTCCCAAATATTAAATAATAAAACAAAAAAATTGAAAAAAGTGTTT

CCACCATTTTTTCAATTTTTT

> SEQ ID NO: 9 nisin promoter
AAACAGTCTTAATTCTATCTTGAGAAAGTATTGGTAATAATATTATTGTCG
ATAACGCGAGCATAATAAACGGCTCTGATTAAATTCTGAAGTTTGTTAGATACAA
TGATTTCGTTCGAAGGAACTACAAAATAAATTATAAGGAGGCACTCAAA > SEQ ID NO: 10 pac-site and pacA gene disruption with kanR (unformatted: pacA
gene seqeuence, underlined: pacA gene seqeucne included in the allelic exchange substrate,
bold: Kan gene promoter, italicized: Kan gene)
ACGATCACAAGAAGAATTTTGCTCGCCTGGCGCGAGATGGTGGTTACACC

ATCGCACAGTATGCCGCCGAGTTTAATCTTAACCCTAATACCGCACGTCGTTATC

TCCGTGCCTTCAAAGAAGACACCAGGACTACGGACAGCCGCAAGCCAAATAAGC

CAGTCAGGAAGCCGGAATTGCCAGCTGGGGCGCCCTCTGGTAAGGTTGGGA

AGCCCTGCAAAGTAAACTGGATGGCTTTCTCGCCGCCAAGGATCTGATGGC

GCAGGGGATCAAGCTCTGATCAAGAGACAGGATGAGGATCGTTTCGCATGAT

TGAACAAGATGGATTGCACGCAGGTTCTCCGGCCGCTTGGGTGGAGAGGCTATTCGG

CTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAA

CTGCAAGACGAGGCAGCGCGGCTATCGTGGCTGGCCACGACGGGCGTTCCTTGCGC

AGCTGTGCTCGACGTTGTCACTGAAGCGGGAAGGGACTGGCTGCTATTGGGCGAAGT

GCCGGGGCAGGATCTCCTGTCATCTCACCTTGCTCCTGCCGAGAAAGTATCCATCATG

GCTGATGCAATGCGGCGGCTGCATACGCTTGATCCGGCTACCTGCCCATTCGACCAC

CAAGCGAAACATCGCATCGAGCGAGCACGTACTCGGATGAAGCCGGTCTTGTCGAT

CAGGATGATCTGGACGAAGAGCATCAGGGGCTCGCGCCAGCCGAACTGTTCGCCAGG

```
CTCAAGGCGAGCATGCCCGACGGCGAGGATCTCGTCGTGACCCATGGCGATGCCTGC

TTGCCGAATATCATGGTGGAAAATGGCCGCTTTTCTGGATTCATCGACTGTGGCCGGC

TGGGTGTGGCGGACCGCTATCAGGACATAGCGTTGGCTACCCGTGATATTGCTGAAGA

GCTTGGCGGCGAATGGGCTGACCGCTTCCTCGTGCTTTACGGTATCGCCGCTCCCGA

TTCGCAGCGCATCGCCTTCTATCGCCTTCTTGACGAGTTCTTCTGAGCCCACCGGACC

TTACGTGATCGCCTGGAACGCGACACCCTGGATGATGATGGTGAACGCTTTGAAT

TCGAAGTTGGCGATTACCTGATAGATAACGTTGAAGCGCGGAAGGCCGCGCGCG

CTATGTTGCGTCGGTCCGGGGCCGATGTTCTGGAAACCACTCTTCTGGAAAAGTC

TCTTTCTCATCTCCTTATGCTGGAGAAC

> SEQ ID NO: 11 Pblast promoter
CGTCAGGTGGCACTTTTCGGGAAATGTGCGCGGAACCCCTATTTGTTTATT
TTCTAAATACATTCAAATATGTATCCGCTCATGAGACAATAACCCTGATAAATGC
TTCAATAATATTGAAAAGGAAGAGT >SEQ ID NO: 12 P1 pacA gene loci with kan gene and luxAB genes inserted (lower case is
native sequence, upper case is insert sequence)
atgtgactttcgttaccctcgcgtcaaaaagagtttttacgaaaggaagcataagtg acctgggacgatcacaagaagaatttgctcgcctggcgcgagatggtggttacaccatcgc acagtatgccgccgagtttaatcttaaccctaataccgcacgtcgttatctccgtgccttca aagaagacaccaggactacggacagccgcaagccaaataagccagtcaggaagAAGAGAAAG

CAGGTAGCTTGCAGTGGGCTTACATGGCGATAGCTAGACTGGGCGGTTTTATGGACAGCAAG

CGAACCGGAATTGCCAGCTGGGGCGCCCTCTGGTAAGGTTGGGAAGCCCTGCAAAGTAAACT

GGATGGCTTTCTTGCCGCCAAGGATCTGATGGCGCAGGGGATCAAGATCTGATCAAGAGACA

GGATGAGGATCGTTTCGCATGATTGAACAAGATGGATTGCACGCAGGTTCTCCGGCCGCTTG

GGTGGAGAGGCTATTCGGCTATGACTGGGCACAACAGACAATCGGCTGCTCTGATGCCGCCG

TGTTCCGGCTGTCAGCGCAGGGGCGCCCGGTTCTTTTTGTCAAGACCGACCTGTCCGGTGCC

CTGAATGAACTGCAGGACGAGGCAGCGCGGCTATCGTGGCTGGCCACGACGGGCGTTCCTTG

CGCAGCTGTGCTCGACGTTGTCACTGAAGCGGGAAGGGACTGGCTGCTATTGGGCGAAGTGC

CGGGGCAGGATCTCCTGTCATCCCACCTTGCTCCTGCCGAGAAAGTATCCATCATGGCTGAT

GCAATGCGGCGGCTGCATACGCTTGATCCGGCTACCTGCCCATTCGACCACCAAGCGAAACA

TCGCATCGAGCGAGCACGTACTCGGATGGAAGCCGGTCTTGTCGATCAGGATGATCTGGACG

AAGAGCATCAGGGGCTCGCGCCAGCCGAACTGTTCGCCAGGCTCAAGGCGCGCATGCCCGAC

GGCGAGGATCTCGTCGTGACCCATGGCGATGCCTGCTTGCCGAATATCATGGTGGAAAATGG

CCGCTTTTCTGGATTCATCGACTGTGGCCGGCTGGGTGTGGCGGACCGCTATCAGGACATAG

CGTTGGCTACCCGTGATATTGCTGAAGAGCTTGGCGGCGAATGGGCTGACCGCTTCCTCGTG

CTTTACGGTATCGCCGCTCCCGATTCGCAGCGCATCGCCTTCTATCGCCTTCTTGACGAGTT

CTTCTGAATTGAAAAAGGAAGAGTATGAGTATTCAACATTTCCGTGTCGCCCTTATTCCCTT

TTTTGCGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGTAAGATC

CTTGAGAGTTTTCGCCCCGAAGAACGTTTTCCAATGATGAGCACTTTTAAAGTTCTGCTATG

TGGCGCGGTATTATCCCGTATTGACGCCGGGCAAGAGCAACTCGGTCGCCGCATACACTATT

CTCAGAATGACTTGGTTGAGTACTCGTCAGGTGGCACTTTTCGGGGAAATGTGCGCGGAACC

CCTATTTGTTTATTTTTCTAAATACATTCAAATATGTATCCGCTCATGAGACAATAACCCTG

ATAAATGCTTCAATAATATTGAAAAGGAAGAGTATGAAGTTTGGAAATATTTGTTTTTCGT
```

-continued

```
ATCAACCACCAGGTGAAACTCATAAGCAAGTAATGGATCGCTTTGTTCGGCTTGGTATCGCC

TCAGAAGAGGTAGGGTTTGATACATATTGGACCTTAGAACATCATTTTACAGAGTTTGGTCT

TACGGGAAATTTATTTGTTGCTGCGGCTAACCTGTTAGGAAGAACTAAAACATTAAATGTTG

GCACTATGGGGGTTGTTATTCCGACAGCACACCCAGTTCGACAGTTAGAAGACGTTTTATTA

TTAGATCAAATGTCGAAAGGTCGTTTTAATTTTGGAACCGTTCGAGGGCTATACCATAAAGA

TTTTCGAGTATTTGGTGTTGATATGGAAGAGTCTCGAGCAATTACTCAAAATTTCTACCAGA

TGATAATGGAAAGCTTACAGACAGGAACCATTAGCTCTGATAGTGATTACATTCAATTTCCT

AAGGTTGATGTATATCCCAAAGTGTACTCAAAAAATGTACCAACCTGTATGACTGCTGAGTC

CGCAAGTACGACAGAATGGCTAGCAATACAAGGGCTACCAATGGTTCTTAGTTGGATTATTG

GTACTAATGAAAAAAAAGCACAGATGGAACTCTATAATGAAATTGCGACAGAATATGGTCAT

GATATATCTAAAATAGATCATTGTATGACTTATATTTGTTCTGTTGATGATGATGCACAAAA

GGCGCAAGATGTTTGTCGGGAGTTTCTGAAAAATTGGTATGACTCATATGTAAATGCGACCA

ATATCTTTAATGATAGCAATCAAACTCGTGGTTATGATTATCATAAAGGTCAATGGCGTGAT

TTTGTTTTACAAGGACATACAAACACCAATCGACGTGTTGATTATAGCAATGGTATTAACCC

TGTAGGCACTCCTGAGCAGTGTATTGAAATCATTCAACGTGATATTGATGCAACGGGTATTA

CAAACATTACATGCGGATTTGAAGCTAATGGAACTGAAGATGAAATAATTGCTTCCATGCGA

CGCTTTATGACACAAGTCGCTCCTTTCTTAAAAGAACCTAAATAAATTACTTATTTGATACT

AGAGATAATAAGGAACAAGTTATGAAATTTGGATTATTTTTTCTAAACTTTCAGAAAGATGG

AATAACATCTGANGAAACGTTGGATAATATGGTAAAGACTGTCACGTTAATTGATTCAACTA

AATATCATTTTAATACTGCCTTTGTTAATGAACATCACTTTTCAAAAAATGGTATTGTTGGA

GCACCTATTACCGCAGCTGGTTTTTTATTAGGGTTAACAAATAAATTACATATTGGTTCATT

AAATCAAGTAATTACCACCCATCACCCTGTACGTGTAGCAGAAGAAGCCAGTTTATTAGATC

AAATGTCAGAGGGACGCTTCATTCTTGGTTTTAGTGACTGCGAAAGTGATTTCGAAATGGAA

TTTTTTAGACGTCATATCTCATCAAGGCAACAACAATTTGAAGCATGCTATGAAATAATTAA

TGACGCATTAACTACAGGTTATTGTCATCCCCAAAACGACTTTTATGATTTTCCAAAGGTTT

CAATTAATCCACACTGTTACAGTGAGAATGGACCTAAGCAATATGTATCCGCTACATCAAAA

GAAGTCGTCATGTGGGCAGCGAAAAAGGCACTGCCTTTAACATTTAAGTGGGAGGATAATTT

AGAAACCAAAGAACGCTATGCAATTCTATATAATAAAACAGCACAACAATATGGTATTGATA

TTTCGGATGTTGATCATCAATTAACTGTAATTGCGAACTTAAATGCTGATAGAAGTACGGCT

CAAGAAGAAGTGAGAGAATACTTAAAAGACTATATCACTGAAACTTACCCTCAAATGGACAG

AGATGAAAAAATTAACTGCATTATTGAAGAGAATGCAGTTGGGTCTCATGATGACTATTATG

AATCGACAAAATTAGCAGTGGAAAAAACAGGGTCTAAAAATATTTTATTATCCTTTGAATCA

ATGTCCGATATTAAAGATGTAAAAGATATTATTGATATGTTGAACCAAAAAATCGAAATGAA

TTTACCATAAAGTACTCACCAGTCACAGAAAAGCATCTTACGGATGGgcccaccggaccttA cgtgatcgcctggaacgcgacaccctggatgatgatggtgaacgctttgaattcgaagttgg cgattacctgatagataacgttgaagcgcggaaggccgcgcgcgctatgttgcgtcggtccg gggccgatgttctggaaaccactcttctggaaaagtctctttctcatctccttatgctggag aacgccagggatacgtgtattcgcctggtgcaggaaatgcgcgatcagcaaaaagacgatga tgaaggtactccgcctgaataccgtatcgcgagcatgctaaacagctgttccgcgcagataa gcagcctgatcaacaccatttacagcatccggaataactatcgaaaagaaagccgggaggcg gaaaagcacgctttatctatggggcaagctggcattgttaagctggcatacgaacgaaagcg
```

```
tgaaaataactggtcagtgctggaagcggctgaattcatcgaggcgcatggaggaaaagtgc cgccectgatgctggagcaaatcaaagccgatctgcgtgctcctaagaccaataccgatgat gaggaaaaccaaacagcatctggcgctccatcacttgaagatctggataaaatcgcgcgaga acgggccgccagccgccgcgctgatgccgcattgtggattgagcatcgtagagaagaaattg ccgatatcgtcgatacaggtggttatggtgatgtcgatgcggaaggcatatcaaacgaagca tggcttgaacaggatctggacgaagacgaggaggaagacgaagaagttacccgcaaactgta cggggatgatgattaatggccagaagttgcgtaacggacccacgttggcgcgagcttgtggc gctatatcgttatgactggattgcggccgctgatgtgttgtttgggaagacaccaacctggc agcaggatgagatcattgagtccacgcagcaggacggcagttggacaagtgtgacctccggc catggtactggtaaatcggatatgacgagtatcattgcaatactcttcatcatgttttccc cggcgctcgcgtcattctggtcgctaacaaaagacagcaagtccttgatggtattttcaaat acataaagagcaattgggctactgctgttagcagattcccgtggttgtcgaagtatttcatt cttacagaaacgtctttttttgaggtgactggcaagggtgtttggacaatattgataaagtc ctgtcgtcccggaaatgaggaggcgttggctggtgaacacgccgatcatctcttgtatatca tcgacgaagcgtcgggtgtgagtgataaagcattcagtgtgataacaggtgcgctgaccggt aaggataaccgtattctgcttctttcccagcctacgcgaccttcaggctatttctacgattc acaccacagactagctattcgcccgggaaatcctgatggattgtttactgcgataatactga atagtgaagaatctccgcttgtagatgcaaaatttatacgagcaaaacttgcggagtatggc ggtcgtgataaccccatgtacatgatcaaagtacgtggtgaatttcccaaatctcaagatgg ctttcttcttggtcgtgatgaggttgagcgggcgacgcggcgaaaggtcaagattgccaaag gatgggctgggttgcatgtgttgacgttgctggtggcacaggacgagataagtccgttatt aatatcatgatggtgtccggccagcgaaataaacgccgtgtaatcaactatcgtatgctgga atacacagacgttacagaaacgcagttagccgccaagattttcgcagaatgtaacccagaac ggttcccgaacataaccatagctattgatggcgatggcttggggaaatcgacggctgatcta atgtacgaacgctatggcattaccgtccagcgtatccgctggggtaaaaagatgcacagccg tgaagataaaagccttttatttcgatatgcgcgctttcgcgaatattcaggcggcagaagctg taaaatcagggcgtatgaggcttgataaggggctgcgactatagaggaagcatcaaagata ccggtagggataaattccgcaggtcaatggaaggtgatgtcaaaggaagatatgaagaaaaa actcaacctgcactcaccggaccattgggatacatattgtttcgctatgttggcgaactatg ttccccaagatgaagtgcttagcgtcgaagacgaagcgcaggttgatgaagctctggcatgg cttaatgaataa
```

The invention claimed is:

1. A bacterial cell packaging system for packaging a reporter nucleic acid molecule into a non-replicative transduction particle (NRTP) for introduction into a bacterial cell, the bacterial cell packaging system comprising a host cell, comprising:

a bacteriophage genome comprising a first terminase gene comprising a disrupted packaging initiation site sequence, wherein in the absence of the disruption the first terminase gene encodes a first terminase protein and wherein the first terminase protein recognizes the first-packaging initiation site sequence, wherein the disruption prevents recognition of the packaging initiation site sequence by the first terminase protein, and wherein the disruption further renders non-functional the first terminase protein; and a reporter nucleic acid molecule comprising a reporter gene, a first terminase gene comprising a non-disrupted packaging initiation site sequence and encoding a functional first terminase protein, and a second terminase gene encoding a second terminase protein, wherein the non-disrupted packaging initiation site sequence is configured to facilitate packaging of a replicon of the reporter nucleic acid molecule into the NRTP.

2. The bacterial cell packaging system of claim 1, wherein the bacteriophage genome comprises a plurality of disrupted terminase genes, wherein in the absence of the disruptions, each of the plurality of disrupted terminase genes encodes a terminase protein.

3. The bacterial cell packaging system of claim 2, wherein each of the plurality of disrupted genes on the bacteriophage genome is complemented by a functional, non-disrupted gene encoded by the reporter nucleic acid molecule.

4. The bacterial cell packaging system of claim 1, wherein the reporter nucleic acid molecule comprises a sequence selected from SEQ ID NO:1, SEQ ID NO:4, and SEQ ID NO:6.

5. The bacterial cell packaging system of claim 1 wherein the disruption of the first terminase gene is by an insertion, replacement, deletion, or mutation that disrupts the packaging initiation site.

6. The bacterial cell packaging system of claim 5 wherein the disruption of the first terminase gene is by an insertion of a gene encoding a detectable marker, a gene encoding a selectable marker or both a gene encoding a detectable marker and a gene encoding a selectable marker.

7. The bacterial cell packaging system of claim 1, wherein both the non-disrupted first terminase gene and the second terminase gene on the reporter nucleic acid molecule are operably linked to a conditional promoter.

8. The bacterial cell packaging system of claim 7, wherein the conditional promoter comprises the sequence of SEQ ID NO: 9.

9. The bacterial cell packaging system of claim 7, wherein the conditional promoter is a native promoter of a terminase gene of the bacteriophage genome.

10. The bacterial cell packaging system of claim 7, wherein expression of the non-disrupted first terminase gene or the second terminase gene is inhibited in the absence of activation of the lytic cycle of the bacteriophage, and wherein expression of the non-disrupted first terminase gene or the second terminase gene is activated upon activation of the lytic cycle of the bacteriophage.

11. The bacterial cell packaging system of claim 1, wherein the reporter gene encodes a detectable marker or a selectable marker.

12. The bacterial cell packaging system of claim 1, wherein the bacteriophage genome comprises SEQ ID NO: 12.

13. The bacterial cell packaging system of claim 1, wherein the reporter nucleic acid molecule comprises an origin of replication.

14. The bacterial cell packaging system of claim 1, wherein the replicon of the reporter nucleic acid molecule comprises a concatamer that is packaged into the non-replicative transduction particle.

15. The bacterial cell packaging system of claim 1, wherein the replicon comprises the sequence of SEQ ID NO:2.

16. The bacterial cell packaging system of claim 1, wherein the reporter nucleic acid molecule is operatively linked to a promoter.

17. The bacterial cell packaging system of claim 16, wherein the promoter is selected for contributing to reactivity of a reporter molecule expressed from the reporter nucleic acid molecule in the bacterial cell.

18. A method for packaging a reporter nucleic acid molecule into a non-replicative transduction particle, comprising:

incubating the bacterial cell packaging system of claim 1 at a temperature that induces a lytic phase of the bacteriophage genome to produce non-replicative transduction particles packaged with the reporter nucleic acid molecule; and collecting the non-replicative transduction particle comprising the reporter nucleic acid molecule.

19. The method of claim 18, wherein the non-replicative transduction particle does not contain a replicated bacteriophage genome.

20. The method of claim 18, wherein the non-replicative transduction particle comprises a portion of the bacteriophage genome due to recombination with the reporter nucleic acid molecule, and wherein the portion of the bacteriophage genome comprises the reporter gene.

21. The bacterial cell packaging system of claim 1, wherein the first terminase gene is selected from group consisting of a pacA gene of bacteriophage P1, a terS gene of bacteriophage φ11 or φ80a, and a terA gene of bacteriophage φEfl1; and the second terminase gene is selected from the group consisting of a pacB gene of bacteriophage P1, a terL gene of bacteriophage φ11 or φ80a, and a terB gene of bacteriophage φEfl1.

* * * * *

SEQUENCE LISTING

<160> NUMBER OF SEQ ID NOS: 13

<210> SEQ ID NO 1
<211> LENGTH: 2733
<212> TYPE: DNA
<213> ORGANISM: Unknown
<220> FEATURE:
<223> OTHER INFORMATION: Description of Unknown: Enterobacteriaceae
      bacteriophage P1 sequence

<400> SEQUENCE: 1

```
atgtgacttt cgttaccctc gcgtcaaaaa gagtttttac gaaaggaagc ataagtgacc        60
tgggacgatc acaagaagaa ttttgctcgc ctggcgcgag atggtggtta caccatcgca       120
cagtatgccg ccgagtttaa tcttaaccct aataccgcac gtcgttatct ccgtgccttc       180
aaagaagaca ccaggactac ggacagccgc aagccaaata agccagtcag gaagccacta       240
aaaagcatga tcattgatca ctctaatgat caacatgcag gtgatcacat tgcggctgaa       300
atagcggaaa aacaaagagt taatgccgtt gtcagtgccg cagtcgagaa tgcgaagcgc       360
caaaataagc gcataaatga tcgttcagat gatcatgacg tgatcacccg cgcccaccgg       420
accttacgtg atcgcctgga acgcgacacc ctggatgatg atggtgaacg ctttgaattc       480
gaagttggcg attacctgat agataacgtt gaagcgcgga aggccgcgcg cgctatgttg       540
cgtcggtccg gggccgatgt tctgaaaacc actcttctgg aaaagtctct ttctcatctc       600
cttatgctgg agaacgccag ggatacgtgt attcgcctgg tgcaggaaat gcgcgatcag       660
caaaaagacg atgatgaagg tactccgcct gaataccgta tcgcgagcat gctaaacagc       720
tgttccgcgc agataagcag cctgatcaac accatttaca gcatccggaa taactatcga       780
aaagaaagcc gggaggcgga aaagcacgct ttatctatgg ggcaagctgg cattgttaag       840
ctggcatacg aacgaaagcg tgaaaataac tggtcagtgc tggaagcggc tgaattcatc       900
gaggcgcatg gaggaaaagt gccgcccctg atgctggagc aaatcaaagc cgatctgcgt       960
gctcctaaga ccaataccga tgatgaggaa accaaacag catctggcgc tccatcactt      1020
gaagatctgg ataaaatcgc gcgagaacgg gccgccagcc gccgcgctga tgccgcattg      1080
tggattgagc atcgtagaga agaaattgcc gatatcgtcg atacaggtgg ttatggtgat      1140
gtcgatgcgg aaggcatatc aaacgaagca tggcttgaac aggatctgga cgaagacgag      1200
gaggaagacg aagaagttac ccgcaaactg tacggggatg atgattaaat ggccagaagt      1260
tgcgtaacgg acccacgttg gcgcgagctt gtggcgctat atcgttatga ctggattgcg      1320
gccgctgatg tgttgtttgg gaagacacca acctggcagc aggatgagat cattgagtcc      1380
acgcagcagg acggcagttg gacaagtgtg acctccggcc atggtactgg taaatcggat      1440
atgacgagta tcattgcaat actcttcatc atgttttttcc ccggcgctcg cgtcattctg      1500
gtcgctaaca aaagacagca agtccttgat ggtatttttca aatacataaa gagcaattgg      1560
gctactgctg ttagcagatt cccgtggttg tcgaagtatt tcattcttac agaaacgtct      1620
tttttttgagg tgactggcaa gggtgtttgg acaatattga taaagtcctg tcgtcccgga      1680
aatgaggagg cgttggctgg tgaacacgcc gatcatctct tgtatatcat cgacgaagcg      1740
tcgggtgtga gtgataaagc attcagtgtg ataacaggtg cgctgaccgg taaggataac      1800
cgtattctgc ttctttccca gcctacgcga ccttcaggct atttctacga ttcacaccac      1860
agactagcta ttcgcccggg aaatcctgat ggattgttta ctgcgataat actgaatagt      1920
gaagaatctc cgcttgtaga tgcaaaattt atacgagcaa acttgcgga gtatggcggt      1980
cgtgataacc ccatgtacat gatcaaagta cgtggtgaat ttcccaaatc tcaagatggc      2040
tttcttcttg gtcgtgatga ggttgagcgg gcgacgcggc gaaaggtcaa gattgccaaa      2100
ggatggggct gggttgcatg tgttgacgtt gctggtggca caggacgaga taagtccgtt      2160
attaatatca tgatggtgtc cggccagcga aataaacgcc gtgtaatcaa ctatcgtatg      2220
ctggaataca cagacgttac agaaacgcag ttagccgcca agattttcgc agaatgtaac      2280
ccagaacggt tcccgaacat aaccatagct attgatggcg atggcttggg gaaatcgacg      2340
gctgatctaa tgtacgaacg ctatggcatt accgtccagc gtatccgctg gggtaaaaag      2400
```

| | | | | |
|---|---|---|---|---|
| atgcacagcc | gtgaagataa | aagcctttat | ttcgatatgc | gcgctttcgc | gaatattcag | 2460 |
| gcggcagaag | ctgtaaaatc | agggcgtatg | aggcttgata | aggggggctgc | gactatagag | 2520 |
| gaagcatcaa | agataccggt | agggataaat | tccgcaggtc | aatggaaggt | gatgtcaaag | 2580 |
| gaagatatga | agaaaaaact | caacctgcac | tcaccggacc | attgggatac | atattgtttc | 2640 |
| gctatgttgg | cgaactatgt | tccccaagat | gaagtgctta | gcgtcgaaga | cgaagcgcag | 2700 |
| gttgatgaag | ctctggcatg | gcttaatgaa | taa | | | 2733 |

<210> SEQ ID NO 2
<211> LENGTH: 1727
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 2

| | | | | | | |
|---|---|---|---|---|---|---|
| cactataggg | cgaattggcg | gaaggccgtc | aaggccgcat | tgggcccgg | cgcgccggat | 60 |
| ccgctagctc | tagactggca | ggtttctgag | cagatcgtcc | aacccgatct | ggatcgggtc | 120 |
| agaaaaattt | gctctaataa | atttcgtttt | ctaagtgcaa | agaatcacca | tttcgagctg | 180 |
| gtgattgaag | gttgatgcaa | atttggagaa | aaaatgcaac | aaacattcaa | tgcggatatg | 240 |
| aatatatcaa | accttcatca | aaatgtcgat | ccttcaacca | ctctgcccgt | tatttgtggt | 300 |
| gttgaaatta | cgaccgaccg | cgctggccgt | tacaacctta | atgctctaca | cagagcgagc | 360 |
| ggactcggtg | cccataaagc | gccagctcaa | tggctaagaa | cgctgtcagc | taaacagctc | 420 |
| atcgaagagc | ttgaaaaaga | aactatgcag | aattgcatag | tttcgttcac | aagcaatgga | 480 |
| agcaggattt | ctttcacgac | tcgtataacc | ggcaaaggtc | agcagtggct | gatgaagcga | 540 |
| ttgcttgatg | ctggtgtgct | ggtacctgtc | gcggcaacgc | gctaacagac | gtagtaagaa | 600 |
| ccaccagcat | tgtaatgctg | gctaaagtca | ctttcctgag | ctgtataacg | atgagcgatt | 660 |
| ttactttttc | tggctatgaa | ttggcctgct | ttgtaacaca | ctccggtcta | tcccgtagcg | 720 |
| ccgggcatat | cctgtcgcaa | tgtgcaaatc | tcgcggcaac | aaccagtgaa | tacttcattc | 780 |
| acaagcctca | ccgcctgatc | gcggcagaaa | ctggttatag | ccaatcaacc | gtcgttcgtg | 840 |
| cattccgtga | agctgtaaac | aaaggaattc | tgtctgtaga | gattgttatc | ggcgatcacc | 900 |
| gtgaacgtcg | cgctaacctg | taccggttta | caccatcctt | tttggccttc | gcacaacaag | 960 |
| ccaaaaatgc | gctgatagaa | agcaaattaa | agatctcttc | agcggcaacc | aaggttaaag | 1020 |
| ctgttctcgc | taagacattg | gctttattta | atttttttatc | cacacccca | tgtcaaaatg | 1080 |
| ataccccctc | ccctgtcag | gatgacgtgg | caataaagaa | taagaagtca | caagttaaaa | 1140 |
| aaacaaaaag | atcagtttcc | ggcggtgccg | gaacaaccag | cctcaaaaaa | ttgacttcat | 1200 |
| ggatcgctaa | ggcaaaagca | aaggctgaca | atctgcggtt | atccaaaaaa | cgcactcaaa | 1260 |
| aacatgagtt | caagcagaaa | gtagaggcgg | ctgcgcggaa | atatgcttac | ctgaagaaca | 1320 |
| agcgttcgcc | tgatattggc | gggatatcaa | acttcgataa | cctaccgcat | tgcatgacgg | 1380 |
| taaacgaagc | tcttaatgcg | gttttagcca | aaaataaaga | taacgaacaa | tggggtatac | 1440 |
| cggcaggatt | cagagggtaa | tgaattgctc | taattataac | catgcatact | ttcaacaccct | 1500 |
| ctagtttgcc | atgaggcaaa | ctcataggtg | tcctggtaag | aggacactgt | tgccaaaact | 1560 |
| ggacgccca | ttattgcaat | taataaacaa | ctaacggaca | attctaccta | acaataagtg | 1620 |
| gcttaaaaaa | acccgccccg | gcgggttttt | ttatctagag | ctagcggatc | cggcgcgccg | 1680 |

```
ggcccttctg ggcctcatgg gccttccgct cactgcccgc tttccag         1727
```

<210> SEQ ID NO 3
<211> LENGTH: 773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ttgactgcca cttttacgca acgcataatt gttgtcgcgc tgccgaaaag ttgcagctga    60
ttgcgcatgg tgccgcaacc gtgcggcacc cctaccgcat ggagataagc atggccacgc   120
agtccagaga atcggcatt caagccaaga acaagcccgg tcactgggtg caaacggaac    180
gcaaagcgca tgaggcgtgg gccgggctta ttgcgaggaa acccacggcg gcaatgctgc   240
tgcatcacct cgtggcgcag atgggccacc agaacgccgt ggtggtcagc cagaagacac   300
tttccaagct catcggacgt tctttgcgga cggtccaata cgcagtcaag gacttggtgg   360
ccgagcgctg gatctccgtc gtgaagctca acggccccgg caccgtgtcg gcctacgtgg   420
tcaatgaccg cgtggcgtgg ggccagcccc gcgaccagtt cgcctgtcg gtgttcagtg    480
ccgccgtggt ggttgatcac gacgaccagg acgaatcgct gttggggcat ggcgacctgc   540
gccgcatccc gaccctgtat ccgggcgagc agcaactacc gaccggcccc ggcgaggagc   600
cgcccagcca gcccggcatt ccgggcatgg aaccagacct gccagccttg accgaaacgg   660
aggaatggga acggcgcggg cagcagcgcc tgccgatgcc cgatgagccg tgttttctgg   720
acgatggcga gccgttggag ccgccgacac gggtcacgct gccgcgccgg tag          773
```

<210> SEQ ID NO 4
<211> LENGTH: 1785
<212> TYPE: DNA
<213> ORGANISM: Unknown
<220> FEATURE:
<223> OTHER INFORMATION: Description of Unknown: Enterobacteriaceae
      bacteriophage P1 sequence

<400> SEQUENCE: 4

```
ttttaaaaag cgtatagcgc gagagttggt ggtaaatgaa atgaacgaaa acaaaagag     60
attcgcagat gaatatataa tgaatggatg taatggtaaa aaagcagcaa tttcagcagg   120
ttatagtaag aaaacagcag agtctttagc aagtcgattg ttaagaaatg ttaatgtttc   180
ggaatatatt aaagaacgat tagaacagat acaagaagag cgtttaatga gcattacaga   240
agctttagcg ttatctgctt ctattgctag aggagaacct caagaggctt acagtaagaa   300
atatgaccat ttaaacgatg aagtggaaaa agaggttact tacacaatca caccaacttt   360
tgaagagcgt cagagatcta ttgaccacat actaaaagtt catggtgcgt atatcgacaa   420
aaaagaaatt actcagaaga atattgagat taatattggt gagtacgatg acgaaagtta   480
aattaaactt taacaaacca tctaatgttt tcaacagaaa catattcgaa atactaacca   540
attacgataa cttcactgaa gtacattacg gtggaggttc gagtggtaag tctcacggcg   600
ttatacaaaa agttgtactt aaagcattgc aagactggaa atatcctagg cgtatactat   660
ggcttagaaa agtccaatca acaattaaag atagtttatt cgaagatgtc aaagattgtt   720
tgataaactt cggtatttgg gacatgtgcc tttggaataa gactgataac aaagttgaat   780
tgccaaacgg cgcagttttt ttgtttaaag gattagataa cccagagaaa ataaagtcga   840
```

```
taaaaggcat atcagacata gtcatggaag aagcgtctga attcacacta aatgattaca      900
cgcaattaac gttgcgtttg agggagcgta aacacgtgaa taagcaaata tttttgatgt      960
ttaacccagt atctaaactg aattgggttt ataagtattt ctttgaacat ggtgaaccaa     1020
tggaaaatgt catgattaga caatctagtt atcgagataa taagtttctt gatgaaatga     1080
cacgacaaaa cttagagttg ttagcaaatc gtaatccagc atattacaaa atttatgcgt     1140
taggtgaatt ttctacacta gacaaattgg ttttccctaa gtatgaaaaa cgtttaataa     1200
ataaagatga gttaagacat ttaccttctt attttggatt ggactttggc tacgttaatg     1260
atcctagtgc ttttatacat tctaaaatag atgtaaagaa aaagaagtta tacatcattg     1320
aagagtatgt taaacaaggt atgctgaatg atgaaatagc taatgtcata aagcaacttg     1380
gttatgctaa agaagaaatt acagcagata gtgcagaaca aaaaagtata gctgaattaa     1440
ggaatctagg gcttaaaagg attttaccaa ccaaaaaagg gaagggctcg gttgtacaag     1500
ggttacaatt cttaatgcaa tttgaaatca ttgttgatga acgttgtttc aagactattg     1560
aagagtttga caactacaca tggcaaaagg acaaagatac aggtgaatat accaatgaac     1620
cagtagatac atacaatcat tgtatcgatt cgttgcgtta ttcagtggaa cgattctaca     1680
gaccggttag aaaacgcaca aatgtcagtt cgaagtt ga cacaataaaa tctctaggat     1740
tataggaggg aacaaatgtt aaaagtaaac gaatttgaaa cagat                     1785
```

<210> SEQ ID NO 5
<211> LENGTH: 4681
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (301)..(301)
<223> OTHER INFORMATION: a, c, t, g, unknown or other
<220> FEATURE:
<221> NAME/KEY: modified_base
<222> LOCATION: (4056)..(4056)
<223> OTHER INFORMATION: a, c, t, g, unknown or other

<400> SEQUENCE: 5

```
tttgcggaaa gagttagtaa gttaacagaa gacgagccaa acctaaatgg tttagcagga      60
aacttagata aaaaaatgaa tccagaatta tattcagaac aggaacagca acaagagcaa     120
caaaagaatc aaaaacgaga tagaggtatg cacttataga acatgcattt atgccgagaa     180
aacttattgg ttggaatggg ctatgtgtta gctaacttgt tagcgagttg gttggacttg     240
aattgggatt aatcccaaga aagtaccggc tcaacaaccc ataaagccct gtaggttccg     300
nccaataagg aaattggaat aaagcaataa aaggagttga agaaatgaaa ttcagagaag     360
cctttgagaa ttttataaca agtaagtatg tacttggtgt tttagtagtc ttaactgttt     420
accagataat acaatgcatt aaataaaaaa agacttgatc tgattagacc aaatcttttg     480
atagtgttat attaataaca aaataaaaag gagtcgctca cgccctacca aagtttgtga     540
acgacatcat tcaagaaaaa aaacactgag ttgttttat aatcttgtat atttagatat      600
taaacgatat ttaaatatac atcaagatat atatttgggt gagcgattac ttaaacgaaa     660
ttgagattaa ggagtcgatt ttttatgtat aaaaacaatc atgcaaatca ttcaaatcat     720
ttggaaaatc acgatttaga caattttct aaaaccggct actctaatag ccggttggac      780
gcacatactg tgtgcatatc tgatccaaaa ttaagttttg atgcaatgac gatcgttgga     840
```

```
aatctcaacc gagacaacgc tcaggcccTT tctaaattta tgagtgtaga gccccaaata    900
agactttggg atattcttca aacaaagttt aaagctaaag cacttcaaga aaagtttat    960
attgaatatg acaaagtgaa agcagatagt tgggatagac gtaatatgcg tattgaattt   1020
aatccaaaca aacttacacg agatgaaatg atttggttaa aacaaaatat aataagctac   1080
atggaagatg acggttttac aagattagat ttagcctttg attttgaaga tgatttgagt   1140
gactactatg caatgtctga taaagcagtt aagaaaacta ttttttatgg tcgtaatggt   1200
aagccagaaa caaaatattt tggcgtgaga gatagtaata gatttattag aatttataat   1260
aaaaagcaag aacgtaaaga taatgcagat gctgaagtta tgtctgaaca tttatggcgt   1320
gtagaaatcg aacttaaaag agatatggtg gattactgga atgattgctt tagtgattta   1380
catatcttgc aaccagattg gaaaactatc caacgcactg cggatagagc aatagttttt   1440
atgttattga gtgatgaaga agaatgggga aagcttcaca gaaattctag aacaaaatat   1500
aagaatttga taaagaaat ttcgccagtc gatttaacgg acttaatgaa atcgacttta   1560
aaagcgaacg aaaaacaatt gcaaaaacaa atcgattttt ggcaacatga atttaaattt   1620
tggaaatagt gtacatatta atattactga acaaaaatga tatatttaaa ctattctaat   1680
ttaggaggat ttttttatga agtgtctatt taaaaatttg gggaatttat atgaggtgaa   1740
agataatttt accctataa actttagcca cctcaagtaa agaggtaaaa ttgtttagtt   1800
tatataaaaa atttaaaggt ttgttttata gcgttttatt ttggctttgt attctttcat   1860
tttttagtgt attaaatgaa atggttttaa atgtttcttt acctgatatt gcaaatcatt   1920
ttaatactac tcctggaatt acaaactggg taaacactgc atatatgtta acttttccga   1980
taggaacagc agtatatgga aaattatctg attatataaa tataaaaaa ttgttaatta   2040
ttggtattag tttgagctgt cttggttcat tgattgcttt tattgggccc acctaggcaa   2100
atatgctctt acgtgctatt atttaagtga ctatttaaaa ggagttaata aatatgcggc   2160
aaggtattct taaataaact gtcaatttga tagcgggaac aaataattag atgtcctttt   2220
ttaggagggc ttagtttttt gtacccagtt taagaatacc tttatcatgt gattctaaag   2280
tatccagaga atatctgtat gctttgtata cctatggtta tgcataaaaa tcccagtgat   2340
aaaagtattt atcactggga ttttatgcc cttttgggtt tttgaatgga ggaaaatcac   2400
atgaaaatta ttaatattgg agttttagct catgttgatg caggaaaaac taccttaaca   2460
gaaagcttat tatataacag tggagcgatt acagaattag gaagcgtgga caaaggtaca   2520
acgaggacgg ataatacgct tttagaacgt cagagaggaa ttacaattca gacaggaata   2580
acctcttttc agtgggaaaa tacgaaggtg aacatcatag acacgccagg acatatggat   2640
ttcttagcag aagtatatcg ttcattatca gttttagatg gggcaattct actgattct    2700
gcaaaagatg gcgtacaagc acaaactcgt atattatttc atgcacttag gaaaatgggg   2760
attcccacaa tcttttttat caataagatt gaccaaaatg gaattgattt atcaacggtt   2820
tatcaggata ttaaagagaa actttctgcc gaaattgtaa tcaaacagaa ggtagaactg   2880
tatcctaata tgtgtgtgac gaactttacc gaatctgaac aatgggatac ggtaatagag   2940
ggaaacgata acctttttaga gaaatatatg tccggtaaat cattagaagc attggaactc   3000
gaacaagagg aaagcataag atttcagaat tgttctctgt tccctctta tcatggaagt   3060
gcaaaaagta atataggga tgataacctt atagaagtta ttactaataa attttattca   3120
tcaacacatc gaggtccgtc tgaactttgc ggaaatgttt tcaaaattga atatacaaaa   3180
aaaagacaac gtcttgcata tatacgcctt tatagtggag tactacattt acgagattcg   3240
```

```
gttagagtat cagaaaaaga aaaaataaaa gttacagaaa tgtatacttc aataaatggt    3300
gaattatgta agattgatag agcttattct ggagaaattg ttattttgca aaatgagttt    3360
ttgaagttaa atagtgttct tggagataca aaactattgc cacagagaaa aagattgaa     3420 aatccgcacc ctctactaca aacaactgtt gaaccgagta aacctgaaca gagagaaatg    3480
ttgcttgatg cccttttgga aatctcagat agtgatccgc ttctacgata ttacgtggat    3540
tctacgacac atgaaattat actttctttc ttagggaaag tacaaatgga agtgattagt    3600
gcactgttgc aagaaaagta tcatgtggag atagaactaa agagcctac agtcatttat     3660 atggagagac cgttaaaaaa tgcagaatat accattcaca tcgaagtgcc gccaaatcct    3720
ttctgggctt ccattggttt atctgtatca ccgcttccgt tgggaagtgg aatgcagtat    3780
gagagctcgg tttctcttgg atacttaaat caatcatttc aaaatgcagt tatggaaggg    3840
gtacgctatg gttgcgaaca aggattatat ggttggaatg tgacggattg taaaatctgt    3900
tttaagtacg gttatacta tagccctgtt agtactccag cagattttcg gatgcttact     3960
cctattgtac tggagcaagc ctttagaaaa gctggaacag aattgttaga gccatatctt    4020
agttttaaag tttatgcacc acaggaatat ctttcncggg catataacga tgctcccaaa    4080
tattgtgcaa atatcgtaaa tactcaactg aaaaataatg aggtcattat tattggagaa    4140
attcctgctc gatgtattca agattatcgc aatgatttaa cttttttac aaatgggctt     4200 agtgtttgtt tagcagagct aaaaggatat caggttacca ctggcgaacc tgtttgccag    4260
acccgtcgtc taaatagtcg gatagataaa gtaagatata tgttcaataa aataacttag    4320
tgcgttttat gttgttatat aaatatggtt tcttattaaa taagatgaaa tattctttaa    4380
tatagatttg aattaaagtg gaaggagga gattgttatt ataaactaca agtggatatt     4440
gtgtcctatt tgtggaaata aaacaagact acgaatacga gtggatacta tacttaaaaa    4500
tttcccttta tacagcccca aatgtaagaa cgaaacttta attaatgttc aaaaaatgaa    4560
tataataaca atcaaagagc cagacgccaa gacgcagagc cgataatttg agaaatgaaa    4620
ctctcatctt atcggctctt tttgtttatc tgaattttac tgactagcct tcaatatttc    4680
c                                                                     4681
```

<210> SEQ ID NO 6
<211> LENGTH: 2321
<212> TYPE: DNA
<213> ORGANISM: Unknown
<220> FEATURE:
<223> OTHER INFORMATION: Description of Unknown: Enterobacteriaceae
      bacteriophage P1 sequence

<400> SEQUENCE: 6

```
ctcaattcaa caagtattgt gaggtggtgt tatatgtcag atggataaaa aggaacaagc      60
aaagaaatat tatgaaaaag gttggaaata caaggatatt ccgaaaagc tttctgtacc     120 tctcaacaca ttgaagtcat ggagaaaacg tgataaatgg aaagagggg gtgcaaccaa     180 agaggtgcaa cctacaaata ggggtgcacc taaaggtaat caaaatgcta taggcaataa    240
aggtaatagt cgagcctcgc caccaaaaag aaataagaat gctgttaaaa ctggcgaata    300
cgaaacaata tttgccgata tgttatctga cgaagaaaag gacatctatt ctactatgaa    360
tgatgatcct ttttttattt tggatgaaga aataagaatc ctgaaaattc gccaatatag    420
aatgcttaaa cgcataaaag atgcagaggc tggcttaaat gatgaagaag ttgaacgttt    480
gcagcagctt cgcaaagtta aagagccatc ggtaattgat gggaaaatgg ttactgttaa    540
```

```
gagagaagtt ttaaaagatg tacaagtcac tcgtaaaaca tttagaaagt tagatgacat    600
cctggctatt gaagatgcgt tgactcgcgt tagcaatcaa ttaataaagg cgattaagca    660
acaaaaagaa ttattgtcga cagataaaaa atctcttttta atggaggctc aaattgagaa    720
gataaagctt gagacagaca aattaagtgg cggatcatct aacgatgaag ctgactcttg    780
gaaacaagca gttataaatg cagcaaataa gcgggcggtg aagaaaatg aataagagtt     840 tattccgttt gccgatattg gtgcagcaat tgattactac tacgataaac cagttgcttt    900
ttgtcaggat attttgcatc ttgatccaga tgaatggcag gataaggtct ggatgatttt    960
ggctaaattc ccaaaagtct cagttagatc agggcagggt gttggaaaaa cggcgttgga   1020
ggctggtgct attctttggt ttctaacatg ccggccatat gcaaaagtaa tagcaactgc   1080
tccgacgatg aaacaattat acgatgttct atgggcagaa gtggctaagt ggctgaataa   1140
cagcttgatt aaagacttac ttaaatggac caagacgaaa atttatatgg ttggcgattc   1200
agaacgatgg tttgctacag ctcgaacagc aactaaacca gaaaatatgc aaggatttca   1260
cgaagaccat atgttaatag tggttgatga agcatcaggt gttgctgatc ccattatgga   1320
agcaatatta ggtactcttt caggatttga caataaatta ctaatgtgtg gaaccccaa    1380 caatattgaa gggttttttt atgattcgca taatacagat agagacaagt atagaacgca   1440
caaagtttct agttacgata gcaaacgtac taacaaagaa atattcaaa tgctcatcga    1500 taagtatggt gagaatagcg atgtagctcg tgttcgtatt tatggtgaat tcccaaagg    1560 cgcacttgat tcatttatca gccttgaaat tgttgagttt gccaaagata ttaatatttc   1620
tgattcagaa ttaaaacatg ttagagaagg acacataggt gtcgatgtgg ctcgttttgg   1680
tgatgattca acgatagtat ttcctagaat cggagctaaa gcattgccat ttgaaaaata   1740
tagtaagcaa gataccatgc agaccactgg tcgagtttta aaagcggcga aaggatgat    1800 ggatgactat cctacaataa aaaagtgtt catcaaagta gatgatacag gtgttggtgg    1860
aggtgttact gatagactta agaagtaat tagcgatgaa aaacttccct atgaagtaat    1920
tccggtaaat aatggagaat cttctacaga cgattattat gcaaataaag gaacacaaat   1980
atggggagat gttaaagaac tgttagaaca aaacatttcc aattcgatta atggtcaagg   2040
gccgacgata gaacttcctg ataatgcaaa tctaatcaaa gaattgagca cacgtaaatt   2100
taaaatgact agcaatggaa aaatccgttt agaaagtaaa gaagatatga aaaagcgtaa   2160
tgttggcagt ccagatattg ctgatgcgtt aacgttagcg ttttacgagc catttagacc   2220
agaacctata aacgttaaaa aagctattaa tacgttcaaa aaattaggat taagtaggtg   2280
atagagtgaa taataaatta ttgaacggtt ctagatttga t                       2321
```

<210> SEQ ID NO 7
<211> LENGTH: 2391
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gatcttttgc ccatttttatt tttataaaat gggcaggtgg cgtttgtgta aagcaaatcg     60
acacaatcca aagggataa aaggggaaag tgaaacttcc ccctttttcaa gccacattgt    120 aatacaagaa cgaagtgttt tgtattacaa tgtgatagct tgcagtattt atggtttttat    180 atggtctatt ttgttgtgag gattgtaacc gaatagggcg caatgcttat tacaaaatca    240
```

```
atgacaaagg gcgattgagg aatgagcgct gaggcatttt atctttgagt aagttattga    300
tggatcagaa aaatgtatca caaattgaaa caaagactca ctcatttaag agaagctact    360
atcatgaaat tttgttgttg tgataagcaa cttctaatac acgattttta gccattacat    420
cactcgtttt tagagtgatg tgtaagtgcg cattgcactc ttttttttacg aaacaagccg    480
accagcgttt gaaacttttt agttttcat cattctattt taaaacgttc taaaactcga    540
tttaagcgac tttaattcga aactgtctat ttgttcaaag ggagcattaa gaatgcttaa    600
acgagctttt aaggggtt aaattgattt tgaattgaat agcttgttgt aagttgtaaa    660
aaaaacaagt taaacaaagt atcagttttc catttaaggg ttgttagggc ttgccctgac    720
cgtctgtaag acgcttgatt gcatgatatg agtatttagc tagtcaaaca gttaaaacag    780
cttatatgag caattagagg gaatccaata aattcctaaa agcggttttg atcttttctt    840
ttagcgagtg aacgctgcaa gtaaaatgtg agcgttcact cgctcactcc ttttttttgat    900
gactttgacc tttggtttta aattttttgaa aaaaataaaa aataggcgaa gcctattata    960
tatttatctt atatatttta atctttatt cttttgcgtc aaaaaaaaat caatatttc    1020
aaggctttat agaattatat accaacaaaa aactgtgtat ataccaacaa aaaactgtgc    1080
atacaccaac aaaaaactgt gcatatacca acttctttgt ttgtttcgtt ggtatataat    1140
gatataataa aagcatgaag aatctctcta cgaaaagtgt ttcttcatgc ttatctaaac    1200
tcactcacaa aggagcagtt ttctatgtct agtatatcaa aaaatgaacc taatcaaaag    1260
caggtgcaaa ccttgaacga attgtcaaaa cgaaaagtag tggaacataa ttctttaatt    1320
accagtattg cgaaaatgga taaaacgcca ctgaaaatgt ttgaattagc cgtgtcttgt    1380
attaataccg aagaaccacc caaagatcat acggtttatc tctcaaaaga agaattgttt    1440
gccttttttta aggtatctga taatgacaaa catagtcgtt ttaaacaagc agtagagaat    1500
atgcaaaaac aagcctttt tcaaattaaa gaagaagtag gtaaaggatt taaatttagg    1560
agtattgttc ccattccata tgtcgagtgg acagattatc atgatgacgt aaaaaattgaa    1620
tttcatcgtg aaatcatgcc ctacttaatt aatctaaaac aaaatttcac gcaacatgct    1680
ttgtctgata ttgcagagct gaatagcaaa tactctatta tcttgtaccg ttggttatcc    1740
atgaattata accaatacga gcattatagt tataagggcg gacggagaga agaacaagtg    1800
gaagcctacc gcaatcctac catttcaatg cgagaattac gagaaatgac ggatacagtt    1860
gatgaatacc cccgctttga tagattagaa catagagttt taaagaacc aatagaagaa    1920
attaacgaaa acacctcttt taacgtgacg tatgacaaga taaaaaaagg acgaagcatt    1980
gattctattg tctttcatat cacgaaaaaa cgtcgagcag atgataacag ctacaagtta    2040
gaagataaag attatcaatc cgacaaagag gaaaaatcaa gaatgaagc tgacttatta    2100
aaacaggcaa tggaaagcaa gtacacacga ttattgattg aaaacttct cttatcccct    2160
cttgaaatga cggacacggc acttatggca ggtttgcaaa agaacgtcta tccgttgtat    2220
gacgagttaa aggaattaag aggattgaat ggggtcaaag accacttgtc ttatatatct    2280
agcaaaaaag aagcctattc taaacgcaat gtagcgaagt atctgaaaaa agcaatcgag    2340
caatatctac ctacggttaa aaggcaggac ttaaaccatg agtgagaact t              2391
```

<210> SEQ ID NO 8
<211> LENGTH: 2596
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 8

```
tggcgattct gagacctctg agaggctctc agagctatct aaagctgagg gatatataaa      60
taccttagaa aattattcga agagcttaga agcgaaaata gagcgtttag agcgcgaggg     120
gctgaaatta gaaaaactaa aaacacaaat agctgaccta aaaatcatgt ctgagaaaga     180
actagcggct attacccta aaaaaggcgt gttcggtaaa gaatatgtgg aattgactaa      240
agagcagttt gaagaattta aagggctgat ataccgaagc agaaaccttg ttcatcaaaa     300
agagctagag aatgagcaat taaggcggat agtgcctctg agacgctcta aacggtttga     360
agcgagttgg aacgagctaa agaaaaaagt aagggagaga gcatagagcg tcttaggaac     420
gaaaatagag cgcttagaag tgaaaactca gttttgagac agcaaaatga caaaatgcta     480
ggaaaactga aagagtttat gccagataaa gccttaaaaa attttatatc agagttaaga     540
gctattcagc caatcgtaag ggtagttaaa cgagtgattg aaaaagggct aggcctttga     600
gcgatttatg ccgtgaaagc taattgacaa taagcaaggg caaagtacgc taggacgtga     660
cgagccgaaa ggctttagcg tttcgagccg acacggacaa aggacgtccg cccttggtta     720
cttgttgtca attagaccat ggaataaagt aagcggacat ggtataatag ctaggtcgca     780
acgttctttc gctaagttac gaacttagat tggaggtgag cgctgtgaag actttcctag     840
aacttgtttt gatacctttt gtggttggcg ttgctgcaga ggtaagtgct gattggttga     900
ttcggtatgt tcgaaacaaa cgcgacaaaa attaacctga gttcttttg aggacaaaaa       960
agaaagacag tagttccagc tactgttttt tttgcgttgt gctattcgtt tcctagaact    1020
tctagcgtta aaattattat accacgtttg gatttagaaa gtcaaaattt gaggttttag    1080
gggtgaattt ttcgtgaaac gaaaagagg gctgaaaagc ccttaaaaac ccaattgcgt    1140
agcaaggggtt ttttcttatc ttgatacata tagaaataat gagttttttt attttcttgt    1200
tttaaagcac ctcaaacct tgatattgct gggttttag gtaacaaaaa agcccttgca      1260
atttaataaa ataagtttta taatttaagt gtccaattta aaataataaa cttaggagaa    1320
ttgcaggaac ttttttatat actcaaaaaa attttttgc aagaaaatta taacatgaca      1380
ggtactgaaa atcaagtctt taaggactat tctaagaatg gcaaagatag aaagtggcga    1440
gaacgcaagt taaaaatat tgagcttgct ggtcgtttag agcgtttagg atatcgttcg     1500
tttgaacggg tctatcaatg tgccgaagtg ttgaagttta tcgaacaaca agacggcacg    1560
aaaaaactct atcagtctta ttttgcaaa aataagctct gcccaatttg taactggaga     1620
cggtcaatga agtatgctta tcaagctgaa ttagtggtaa atgaagcaat gaaacgctat     1680
ccaaaaggtc gctttctctt tttgaccttg acgattaaga acattagtgg tgaaaaatta    1740
aataaatcaa tttcagaaat agggcgagct tttaatcgtc ttatgaaata caagaaagtc    1800
gataaaaatg ttattggcta tttgcgagcc actgaggtaa cttattcaac tgagcatgag    1860
aattatcacc ctcatttgca tgtattgtta tttgtgaaat ctagctatt tactggaaat     1920
aatacaaatt acattagcca agaagaatgg acgaaactat gggctaaggc gatgaaattg    1980
gattatacac ctgtagttga tattcgaacc gtcaaagctc ataaacgtaa aaacttgaag    2040
tcagctatta tcgaaacagc taaatatcct gttaagcctt ttgatgtaga tacagaagat    2100
gtgacattat tctctgaaat ggtcaaagaa cggataacag aagatttaac gaatggtttg    2160
caccgaaaaa ggcagattgg ttttggaaag ttgttcaaga aaatcaaggc ggagttagct    2220
```

```
cttgatgatg tcgaagaagg gaatcttgtt cagaccggag cagaagaatc tgcagaaagt    2280
actggtcgtg aaattgttgc cttttggaat tgggatagaa agaattattt tgtgaggtag    2340
ctgatgagta aaacagtatc agaattagct caagaattgg gagttagtag gcagtatctt    2400
aatcggattt tatcgcaaaa taatctcggt cgaaaaaaag ggaataaaaa agtagtttcc    2460
gatatggacg agaaagttat gcaagggttt attgttttct aaaatctgat taccaattag    2520
aatgaatatt tcccaaatat taaataataa aacaaaaaaa ttgaaaaaag tgtttccacc    2580 atttttcaa tttttt    2596

<210> SEQ ID NO 9
<211> LENGTH: 155
<212> TYPE: DNA
<213> ORGANISM: Unknown
<220> FEATURE:
<223> OTHER INFORMATION: Description of Unknown: Nisin promoter
      sequence

<400> SEQUENCE: 9
aaacagtctt aattctatct tgagaaagta ttggtaataa tattattgtc gataacgcga     60
gcataataaa cggctctgat taaattctga agtttgttag atacaatgat ttcgttcgaa    120
ggaactacaa ataaaattat aaggaggcac tcaaa                               155

<210> SEQ ID NO 10
<211> LENGTH: 1307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
acgatcacaa gaagaatttt gctcgcctgg cgcgagatgg tggttacacc atcgcacagt     60
atgccgccga gtttaatctt aaccctaata ccgcacgtcg ttatctccgt gccttcaaag    120
aagacaccag gactacggac agccgcaagc caaataagcc agtcaggaag ccggaattgc    180
cagctggggc gccctctggt aaggttggga agccctgcaa agtaaactgg atggcttttct   240 cgccgccaag gatctgatgg cgcaggggat caagctctga tcaagagaca ggatgaggat    300
cgtttcgcat gattgaacaa gatggattgc acgcaggttc tccggccgct tgggtggaga    360
ggctattcgg ctatgactgg gcacaacaga caatcggctg ctctgatgcc gccgtgttcc    420
ggctgtcagc gcaggggcgc ccggttcttt ttgtcaagac cgacctgtcc ggtgccctga    480
atgaactgca agacgaggca gcgcggctat cgtggctggc cacgacgggc gttccttgcg    540
cagctgtgct cgacgttgtc actgaagcgg gaagggactg gctgctattg ggcgaagtgc    600
cggggcagga tctcctgtca tctcaccttg ctcctgccga gaaagtatcc atcatggctg    660
atgcaatgcg gcggctgcat acgcttgatc cggctacctg cccattcgac caccaagcga    720
aacatcgcat cgagcgagca cgtactcgga tggaagccgg tcttgtcgat caggatgatc    780
tggacgaaga gcatcagggg ctcgcgccag ccgaactgtt cgccaggctc aaggcgagca    840
tgcccgacgg cgaggatctc gtcgtgaccc atggcgatgc ctgcttgccg aatatcatgg    900
tggaaaatgg ccgcttttct ggattcatcg actgtggccg gctgggtgtg gcggaccgct    960
atcaggacat agcgttggct acccgtgata ttgctgaaga gcttggcggc gaatgggctg   1020
accgcttcct cgtgctttac ggtatcgccg ctcccgattc gcagcgcatc gccttctatc   1080
gccttcttga cgagttcttc tgagcccacc ggaccttacg tgatcgcctg aacgcgaca    1140
```

```
ccctggatga tgatggtgaa cgctttgaat tcgaagttgg cgattacctg atagataacg      1200
ttgaagcgcg gaaggccgcg cgcgctatgt tgcgtcggtc cggggccgat gttctggaaa      1260
ccactcttct ggaaaagtct ctttctcatc tccttatgct ggagaac                    1307

<210> SEQ ID NO 11
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
cgtcaggtgg cacttttcgg gaaatgtgcg cggaacccct atttgtttat tttctaaata       60
cattcaaata tgtatccgct catgagacaa taaccctgat aaatgcttca ataatattga      120
aaaggaagag t                                                           131

<210> SEQ ID NO 12
<211> LENGTH: 6145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2860)..(2860)
<223> OTHER INFORMATION: a, c, t, g, unknown or other

<400> SEQUENCE: 12
atgtgacttt cgttaccctc gcgtcaaaaa gagtttttac gaaaggaagc ataagtgacc       60
tgggacgatc acaagaagaa ttttgctcgc ctggcgcgag atggtggtta caccatcgca      120
cagtatgccg ccgagtttaa tcttaaccct aataccgcac gtcgttatct ccgtgccttc      180
aaagaagaca ccaggactac ggacagccgc aagccaaata agccagtcag gaagaagaga      240
aagcaggtag cttgcagtgg gcttacatgg cgatagctag actgggcggt tttatggaca      300
gcaagcgaac cggaattgcc agctggggcg ccctctggta aggttgggaa gccctgcaaa      360
gtaaactgga tggcttttctt gccgccaagg atctgatggc gcaggggatc aagatctgat      420
caagagacag gatgaggatc gtttcgcatg attgaacaag atggattgca cgcaggttct      480
ccggccgctt gggtggagag gctattcggc tatgactggg cacaacagac aatcggctgc      540
tctgatgccg ccgtgttccg gctgtcagcg caggggcgcc cggttctttt tgtcaagacc      600
gacctgtccg gtgccctgaa tgaactgcag gacgaggcag cgcggctatc gtggctggcc      660
acgacgggcg ttccttgcgc agctgtgctc gacgttgtca ctgaagcggg aagggactgg      720
ctgctattgg gcgaagtgcc ggggcaggat ctcctgtcat cccaccttgc tcctgccgag      780
aaagtatcca tcatggctga tgcaatgcgg cggctgcata cgcttgatcc ggctacctgc      840
ccattcgacc accaagcgaa acatcgcatc gagcgagcac gtactcggat ggaagccggt      900
cttgtcgatc aggatgatct ggacgaagag catcaggggc tcgcgccagc cgaactgttc      960
gccaggctca aggcgcgcat gcccgacggc gaggatctcg tcgtgaccca tggcgatgcc     1020
tgcttgccga atatcatggt ggaaaatggc cgcttttctg gattcatcga ctgtggccgg     1080
ctgggtgtgg cggaccgcta tcaggacata gcgttggcta cccgtgatat tgctgaagag     1140
cttggcggcg aatgggctga ccgcttcctc gtgctttacg gtatcgccgc tcccgattcg     1200
```

```
cagcgcatcg ccttctatcg ccttcttgac gagttcttct gaattgaaaa aggaagagta    1260
tgagtattca acatttccgt gtcgcccttta ttccctttt tgcggcattt tgccttcctg    1320
tttttgctca cccagaaacg ctggtgaaag taaaagatgc tgaagatcag ttgggtgcac    1380
gagtgggtta catcgaactg gatctcaaca gcggtaagat ccttgagagt tttcgccccg    1440
aagaacgttt tccaatgatg agcactttta aagttctgct atgtggcgcg gtattatccc    1500
gtattgacgc cgggcaagag caactcggtc gccgcataca ctattctcag aatgacttgg    1560
ttgagtactc gtcaggtggc acttttcggg gaaatgtgcg cggaacccct atttgtttat    1620
ttttctaaat acattcaaat atgtatccgc tcatgagaca ataaccctga taaatgcttc    1680
aataatattg aaaaaggaag agtatgaagt ttggaaatat ttgttttcg tatcaaccac    1740 caggtgaaac tcataagcaa gtaatggatc gctttgttcg gcttggtatc gcctcagaag    1800
aggtagggtt tgatacatat tggaccttag aacatcattt tacagagttt ggtcttacgg    1860
gaaatttatt tgttgctgcg gctaacctgt taggaagaac taaaacatta aatgttggca    1920 ctatggggt tgttattccg acagcacacc cagttcgaca gttagaagac gttttattat    1980
tagatcaaat gtcgaaaggt cgttttaatt ttggaaccgt tcgagggcta taccataaag    2040
attttcgagt atttggtgtt gatatggaag agtctcgagc aattactcaa aatttctacc    2100
agatgataat ggaaagctta cagacaggaa ccattagctc tgatagtgat tacattcaat    2160
ttcctaaggt tgatgtatat cccaaagtgt actcaaaaaa tgtaccaacc tgtatgactg    2220
ctgagtccgc aagtacgaca gaatggctag caatacaagg gctaccaatg gttcttagtt    2280
ggattattgg tactaatgaa aaaaagcac agatggaact ctataatgaa attgcgacag    2340
aatatggtca tgatatatct aaaatagatc attgtatgac ttatatttgt tctgttgatg    2400
atgatgcaca aaaggcgcaa gatgtttgtc gggagtttct gaaaaattgg tatgactcat    2460
atgtaaatgc gaccaatatc tttaatgata gcaatcaaac tcgtggttat gattatcata    2520
aaggtcaatg gcgtgatttt gttttacaag gacatacaaa caccaatcga cgtgttgatt    2580
atagcaatgg tattaaccct gtaggcactc ctgagcagtg tattgaaatc attcaacgtg    2640
atattgatgc aacgggtatt acaaacatta catgcggatt tgaagctaat ggaactgaag    2700
atgaaataat tgcttccatg cgacgcttta tgacacaagt cgctcctttc ttaaaagaac    2760
ctaaataaat tacttatttg atactagaga taataaggaa caagttatga aatttggatt    2820
attttttcta aactttcaga aagatggaat aacatctgan gaaacgttgg ataatatggt    2880
aaagactgtc acgttaattg attcaactaa atatcattt aatactgcct tgttaatga    2940 acatcacttt tcaaaaaatg gtattgttgg agcacctatt accgcagctg gtttttattt    3000
agggttaaca aataaattac atattggttc attaaatcaa gtaattacca cccatcaccc    3060
tgtacgtgta gcagaagaag ccagtttatt agatcaaatg tcagagggac gcttcattct    3120
tggttttagt gactgcgaaa gtgatttcga atggaattt tttagacgtc atatctcatc    3180
aaggcaacaa caatttgaag catgctatga ataattaat gacgcattaa ctacaggtta    3240
ttgtcatccc caaaacgact tttatgattt tccaaaggtt tcaattaatc cacactgtta    3300
cagtgagaat ggacctaagc aatatgtatc cgctacatca aaagaagtcg tcatgtgggc    3360
agcgaaaaag gcactgcctt taacatttaa gtgggaggat aatttagaaa ccaaagaacg    3420
ctatgcaatt ctatataata aaacagcaca acaatatggt attgatattt cggatgttga    3480
tcatcaatta actgtaattg cgaacttaaa tgctgataga agtacggctc aagaagaagt    3540
gagagaatac ttaaaagact atatcactga aacttaccct caaatggaca gagatgaaaa    3600
```

```
aattaactgc attattgaag agaatgcagt tgggtctcat gatgactatt atgaatcgac    3660
aaaattagca gtggaaaaaa cagggtctaa aaatatttta ttatcctttg aatcaatgtc    3720
cgatattaaa gatgtaaaag atattattga tatgttgaac caaaaaatcg aaatgaattt    3780
accataaagt actcaccagt cacagaaaag catcttacgg atgggcccac cggaccttac    3840
gtgatcgcct ggaacgcgac accctggatg atgatggtga acgctttgaa ttcgaagttg    3900
gcgattacct gatagataac gttgaagcgc ggaaggccgc gcgcgctatg ttgcgtcggt    3960
ccggggccga tgttctggaa accactcttc tggaaaagtc tctttctcat ctccttatgc    4020
tggagaacgc cagggatacg tgtattcgcc tggtgcagga atgcgcgat cagcaaaaag     4080 acgatgatga aggtactccg cctgaatacc gtatcgcgag catgctaaac agctgttccg    4140
cgcagataag cagcctgatc aacaccattt acagcatccg gaataactat cgaaaagaaa    4200
gccgggaggc ggaaaagcac gctttatcta tggggcaagc tggcattgtt aagctggcat    4260
acgaacgaaa gcgtgaaaat aactggtcag tgctggaagc ggctgaattc atcgaggcgc    4320
atggaggaaa agtgccgccc ctgatgctgg agcaaatcaa agccgatctg cgtgctccta    4380
agaccaatac cgatgatgag gaaaaccaaa cagcatctgg cgctccatca cttgaagatc    4440
tggataaaat cgcgcgagaa cgggccgcca gccgccgcgc tgatgccgca ttgtggattg    4500
agcatcgtag agaagaaatt gccgatatcg tcgatacagg tggttatggt gatgtcgatg    4560
cggaaggcat atcaaacgaa gcatggcttg aacaggatct ggacgaagac gaggaggaag    4620
acgaagaagt tacccgcaaa ctgtacgggg atgatgatta atggccagaa gttgcgtaac    4680
ggacccacgt tggcgcgagc ttgtggcgct atatcgttat gactggattg cggccgctga    4740
tgtgttgttt gggaagacac caacctggca gcaggatgag atcattgagt ccacgcagca    4800
ggacggcagt tggacaagtg tgacctccgg ccatggtact ggtaaatcgg atatgacgag    4860
tatcattgca atactcttca tcatgttttt ccccggcgct cgcgtcattc tggtcgctaa    4920
caaaagacag caagtccttg atggtatttt caaatacata aagagcaatt gggctactgc    4980
tgttagcaga ttcccgtggt tgtcgaagta tttcattctt acagaaacgt ctttttttga    5040
ggtgactggc aagggtgttt ggacaatatt gataaagtcc tgtcgtcccg gaatgaggag    5100
ggcgttggct ggtgaacacg ccgatcatct cttgtatatc atcgacgaag cgtcgggtgt    5160
gagtgataaa gcattcagtg tgataacagg tgcgctgacc ggtaaggata accgtattct    5220
gcttctttcc cagcctacgc gaccttcagg ctatttctac gattcacacc acagactagc    5280
tattcgcccg ggaaatcctg atggattgtt tactgcgata atactgaata gtgaagaatc    5340
tccgcttgta gatgcaaaat ttatacgagc aaaacttgcg gagtatggcg gtcgtgataa    5400
ccccatgtac atgatcaaag tacgtggtga atttcccaaa tctcaagatg ctttcttct    5460 tggtcgtgat gaggttgagc gggcgacgcg gcgaaaggtc aagattgcca aaggatgggg    5520
ctgggttgca tgtgttgacg ttgctggtgg cacaggacga gataagtccg ttattaatat    5580
catgatggtg tccggccagc gaaataaacg ccgtgtaatc aactatcgta tgctggaata    5640
cacagacgtt acagaaacgc agttagccgc caagattttc gcagaatgta acccagaacg    5700
gttcccgaac ataaccatag ctattgatgg cgatggcttg gggaaatcga cggctgatct    5760
aatgtacgaa cgctatggca ttaccgtcca gcgtatccgc tggggtaaaa agatgcacag    5820
ccgtgaagat aaaagccttt atttcgatat gcgcgctttc gcgaatattc aggcggcaga    5880
agctgtaaaa tcagggcgta tgaggcttga taaggggggct gcgactatag aggaagcatc    5940
```

```
aaagataccg gtagggataa attccgcagg tcaatggaag gtgatgtcaa aggaagatat    6000
gaagaaaaaa ctcaacctgc actcaccgga ccattgggat acatattgtt tcgctatgtt    6060
ggcgaactat gttccccaag atgaagtgct tagcgtcgaa gacgaagcgc aggttgatga    6120
agctctggca tggcttaatg aataa                                          6145

<210> SEQ ID NO 13
<211> LENGTH: 61
<212> TYPE: RNA
<213> ORGANISM: Artificial Sequence
<220> FEATURE:
<223> OTHER INFORMATION: Description of Artificial Sequence: cis-
      repressor

<400> SEQUENCE: 13
aaaggcauga aaaacuugg uaucuucacc aacaccuagc uuuuugaagg aauugaguau     60
g                                                                    61
```